United States Patent [19]

Broughton et al.

[11] 3,987,160

[45] Oct. 19, 1976

[54] PHARMACEUTICAL COMPOSITIONS COMPRISING AZAPURINONES USEFUL IN TREATING ALLERGIC RESPIRATORY DISORDERS

[75] Inventors: Barbara Joyce Broughton, Croydon; Bryan John Large, Upminster; Stuart Malcolm Marshall, Stanford-Le-Hope; David Lord Pain, Upminster; Kenneth Robert Harry Wooldridge, Brentwood, all of England

[73] Assignee: May & Baker Limited, Essex, England

[22] Filed: May 29, 1973

[21] Appl. No.: 364,425

Related U.S. Application Data

[62] Division of Ser. No. 207,986, Dec. 14, 1971, Pat. No. 3,819,631.

[30] Foreign Application Priority Data

Dec. 15, 1970 United Kingdom............... 59552/70
Dec. 15, 1970 United Kingdom............... 59556/70
Oct. 26, 1971 United Kingdom............... 49756/71
Nov. 17, 1971 United Kingdom............... 53457/71

[52] U.S. Cl. .................................. 424/45; 424/251
[51] Int. Cl.$^2$ .................. A61K 31/505; A61L 9/04
[58] Field of Search ............... 207/986; 424/45, 251

[56] References Cited

OTHER PUBLICATIONS

Chem. Abstr. vol. 54, 22115g (1960).
Handbook of Non-Prescription Drugs, 1973 Edition, Griffenhagen et al., p. 28.

*Primary Examiner*—Frederick E. Waddell
*Attorney, Agent, or Firm*—Stevens, Davis, Miller & Mosher

[57] ABSTRACT

8-Azapurin-6-ones substituted in the 2-position by an unsubstituted or substituted phenyl or naphthyl group, or by an alkenyl or alkynyl group, a cycloalkyl group, an alkyl group contaning 2 to 10 carbon atoms, or an alkyl group containing 1 to 10 carbon atoms carrying one or more substitutents selected from halogen atoms and hydroxy, cycloalkyl, alkoxy, phenyl and substituted phenyl groups, and pharmaceutically acceptable salts thereof, possess pharmacological properties useful, for example, in the treatment of allergic bronchial asthma.

17 Claims, No Drawings

PHARMACEUTICAL COMPOSITIONS COMPRISING AZAPURINONES USEFUL IN TREATING ALLERGIC RESPIRATORY DISORDERS

This is a division of application Ser. No. 207,986, filed Dec. 14, 1971, and now U.S. Pat. No. 3,819,631.

THIS INVENTION relates to new therapeutically useful 8-azapurin-6-one derivatives, to processes for their preparation and to pharmaceutical compositions containing them.

As a result of research and experimentation, it has been found that the new 8-azapurin-6-one derivatives represented by the general formula:

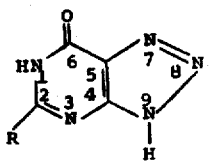

I

[wherein R represents a phenyl or naphthyl group, which may optionally carry one or more (preferably at most three) substituents selected from halogen (preferably fluorine, chlorine or bromine) atoms and hydroxy, alkyl, phenylalkyl, alkoxy, alkenyloxy, alkynyloxy, alkoxyalkoxy, phenoxy, aralkoxy (e.g. phenylalkoxy), alkylthio, hydroxyalkyl, nitro, alkanesulphonyl, alkanoyl, alkoxycarbonyl, amino, trifluoromethyl and methylenedioxy groups and amino groups substituted by one or two groups selected from alkyl, phenyl, alkanoyl, alkanesulphonyl and arenesulphonyl (e.g. benzenesulphonyl) groups, or R represents a straight — or branched — chain alkenyl or alkynyl group containing from 2 to 6 carbon atoms, a cycloalkyl group containing from 3 to 8 carbon atoms (e.g. cyclohexyl), a straight — or branched — chain alkyl group containing from 2 to 10 carbon atoms (preferably isopropyl, butyl or isobutyl), or a straight — or branched — chain alkyl group containing from 1 to 10 carbon atoms (preferably methyl or ethyl) carrying one or more (preferably at most two) substituents selected from halogen atoms, hydroxy groups, cycloalkyl groups containing from 3 to 8 carbon atoms (preferably cyclohexyl), straight — or branched — chain alkoxy groups containing from 1 to 6 carbon atoms, and phenyl groups optionally carrying one or more (preferably at most two) substituents selected from halogen atoms and straight — or branched — chain alkyl andalkoxy groups containing from 1 to 6 carbon atoms, hydroxy groups, and phenylalkoxy (e.g. benzyloxy) groups in which the alkoxy moiety contains 1 to 6 carbon atoms] and pharmaceutically acceptable salts thereof, possess valuable pharmacological properties.

In this specification, when R represents a substituted phenyl or subtituted naphthyl group, alkyl groups and alkyl portions of phenylalkyl, alkylthio, aralkoxy, alkanoyl, alkanesulphonyl, hydroxalkyl and alkoxycarbonyl substituents contain from 1 to 6 carbon atoms; each alkyl portion of an alkoxyalkyl substituent contains from 1 to 6 carbon atom; alkoxy substituents contain from 1 to 10 carbon atoms; alkenyloxy and alkynyloxy substituents contain 2 to 10 carbon atoms and alkyl and alkanoyl groups on amino substituents, and alkane portions of alkanesulphonyl groups on amino substituents, contain from 1 to 6 carbon atoms; phenoxy substituents, and phenyl groups on amino substituents, may carry one or more substituents selected from halogen (e.g. fluorine, chlorine or bromine) atoms, and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, alkyl and alkoxy groups containing from 1 to 6 carbon atoms and nitro groups; and arene (e.g. benzene) portions of arenesulphonyl groups on amino substituents may carry one or more alkyl groups containing from 1 to 6 carbon atoms (e.g. methyl). The carbon atoms in the alkyl, alkoxy, alkanoyl, alkane, alkenyloxy and alkynyloxy groups or moieties may be in a straight — or branched — chain.

It will be understood by those skilled in the art that the compounds of formula I exhibit tautomerism such that each of the hydrogen atoms depicted as residing on the nitrogen atoms in the 1- and 9-positions may reside on any of the nitrogen atoms in the 1-, 3-, 7-, 8- and 9-positions or on the oxygen atom connected to the carbon atom in the 6-position, and that all the forms thus described may be present to a greater or lesser degree and are in a state of dynamic equilibrium with each other. Furthermore, in certain cases the substituent R contributes to optical and/or stereoisomerism. All such forms are embraced by the present invention.

The present invention includes pharmaceutically acceptable salts of compounds of formula I with pharmaceutically acceptable bases. By the term "pharmaceutically acceptable salts" is meant salts the cations of which are relative innocuous to the animal organism when used in therapeutic doses so that the beneficial pharmacological properties of the parent compounds of general formula I are not vitiated by side effects ascribable to those cations. Suitable salts include the alkali metal, e.g. sodium and potassium, and ammonium salts and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

Pharmaceutically acceptable salts may be prepared by the reaction together of stoichiometric quantities of a compound of formula I and the appropriate base, that is to say, a base as described immediately hereinbefore, for example at an elevated temperature, with or without an appropriate solvent, preferably followed by recrystallisation from an appropriate solvent, for example a hydroxylic solvent, e.g. water, of the salt so formed.

According to a feature of the present invention, compounds of formula I are prepared from compounds of the general formula:-

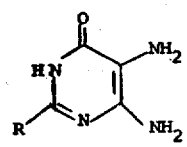

II (wherein R is as hereinbefore defined) by the action of a source of nitrous acid, for example a nitrite of an alkali metal, e.g. sodium nitrite or potassium nitrite, together with an acid, for example dilute aqueous hydrochloric acid, preferably as the reaction medium. at a temperature near or below the ambient temperature, for example between 0° and 30° C.

Compounds of formula II may be prepared, for example, by the reduction of compounds of the general formula:

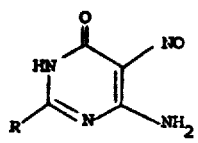

(wherein R is as hereinbefore defined) with suitable reducing agents, for example sodium dithionite in water or an aqueous lower alkanol, e.g. aqueous ethanol, optionally in the presence of a base, e.g. triethylamine.

Compounds of formula II may also be prepared by the reduction of compounds of the general formula:

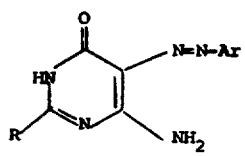

(wherein R is as hereinbefore defined, and Ar represents an aryl group, for example a phenyl group, which may carry one or more substituents selected from, for example, halogen atoms, alkyl and alkoxy groups containing from 1 to 6 carbon atoms, and nitro groups) with a suitable reducing agent, for example sodium dithionite in water or an aqueous lower alkanol, e.g. aqueous ethanol.

Compounds of formula III may be prepared, for example, by the reaction of compounds of the general formula:

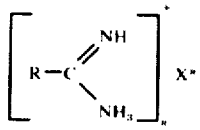

(wherein R is as hereinbefore defined, $X^{n-}$ represents the anion of a suitable acid, for example an inorganic acid, (e.g. hydrochloric acid), or a strong organic acid (e.g. methanesulphonic or toluene-p-sulphonic acid), and $n$ is the basicity of that acid) with an alkyl α-oximinocyanoacetate, for example ethyl α-oximinocyanoacetate, in the presence of a lower alkoxide of an alkali metal in a lower alkanol, for example sodium ethoxide in ethanol, preferably at an elevated temperature, advantageously at the reflux temperature of the reaction mixture.

Compounds of formula III may also be prepared by the nitrosation of compounds of the general formula:

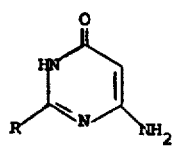

(wherein R is as hereinbefore defined) with a source of nitrous acid, for example a nitrite of an alkali metal, e.g. sodium nitrite or potassium nitrite, together with an acid, for example dilute aqueous hydrochloric acid, preferably as the reaction medium.

Compounds of formula IV may be prepared, for example, by the reaction of compounds of formula V with compounds of the general formula:

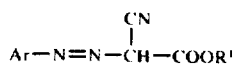

(wherein Ar is as hereinbefore defined, and $R^1$ represents an alkyl group containing from 1 to 6 carbon atoms, preferably methyl or ethyl) in the presence of a lower alkoxide of an alkali metal in a lower alkanol, for example sodium ethoxide in ethanol, preferably at an elevated temperature, advantageously at the reflux temperature of the reaction mixture.

Compounds of formula IV may alternatively be prepared by the reaction of alkaline aqueous solutions of compounds of formula VI with solutions of compounds of the general formula:

(wherein Ar, X and n are as hereinbefore defined) in water or a dilute acid of the formula $H_nX$ (wherein X and n are as hereinbefore defined), preferably at below room temperature, for example at 0°–10° C.

Compounds of formula V may be prepared by the action of acids of the general formula $H_nX$ (wherein X and n are as hereinbefore defined) on compounds of the general formula:

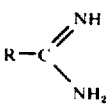

(wherein R is as hereinbefore defined), which may themselves be prepared, for example, by the catalytic hydrogenation of compounds of the general formula:

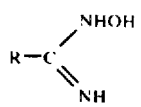

(wherein R is as hereinbefore defined), preferably using Raney nickel as catalyst.

Compounds of formula X may be prepared by the reaction of hydroxylamine hydrochloride with compounds of the general formula:

RCN     XI (wherein R is as hereinbefore defined) with a basic catalyst in a suitable solvent, for example sodium carbonate in aqueous ethanol, sodium hydride in ethyl cellosolve, or triethylamine, which may also act as solvent.

Compounds of formula IX may also be prepared by the reaction of alcoholic ammonia with compounds of the general formula:

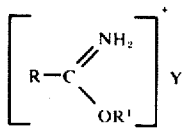

(wherein R and R¹ are as hereinbefore defined and Y⁻ represents a suitable anion, for example a chloride, borofluoride or fluorosulphonate ion) at temperatures between, for example, 0° and 60° C.

Compounds of formula IX, wherein R is other than a substituted or unsubstituted phenyl or naphthyl group, may also be prepared by the reaction of a compound M⁺NH₂⁻ where M represents a sodium or potassium atom, with compounds of formula XI according to the method described by J. Newbery and W. Webster, J. Chem. Soc., 1947, 738.

Compounds of formula XII, wherein R and R¹ are as hereinbefore defined (but preferably not a phenyl group with a substituent in the 2- or 6-position, nor a naphth-1-yl group, nor a naphth-2-yl group with a substituent in the 1- or 3-position) and Y⁻ is a chloride ion, may be prepared by the action of an anhydrous solution of hydrogen chloride in the corresponding alkanol of formula R¹OH on compounds of formula XI (wherein R is as hereinbefore defined).

Compounds of formula XII, wherein R and R¹ are as hereinbefore defined and Y⁻ is a borofluoride or a fluorosulphonate ion, may be prepared by the reaction of the appropriate trialkyloxonium borofluoride and alkyl fluorosulphonate respectively [wherein the alkyl groups(s) are groups R¹] with compounds of the general formula:

RCONH₂    XIII (wherein R is as hereinbefore defined) in a suitable solvent, for example anhydrous methylene chloride, preferably at or near the ambient temperature.

Compounds of formula VI may be prepared, for example, by the reaction of compounds of formula V with an alkyl cyanoacetate, for example ethyl cyanoacetate, in the presence of a lower alkoxide of an alkali metal in a lower alkanol, for example sodium ethoxide in ethanol, preferably at an elevated temperature, advantageously at the reflux temperature of the reaction mixture.

According to a further feature of the present invention, compounds of formula I are prepared by the reaction of compounds of the general formula:

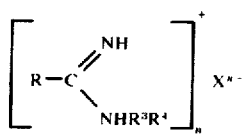

(wherein R, X and n are as hereinbefore defined, and R³ and R⁴ each represent a hydrogen atom or an alkyl group containing from 1 to 6 carbon atoms, preferably methyl) with compounds of the general formula:

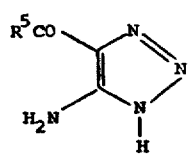

(wherein R⁵ represents a hydroxy, alkoxy, amino, alkylamino or dialkylamino group, the alkoxy group and the alkyl groups in the said alkylamino and dialkylamino groups each containing from 1 to 6 carbon atoms) at elevated temperatures, preferably at 150° C. to 250° C, in the presence of a base, preferably sodium acetate, and advantageously in the presence of a suitable solvent, for example polyethylene glycol 200, in a manner similar to that described by B. R. Baker and J. A. Kozma, J. Med. Chem., 1968, 11, 656.

Compounds of formula XIV may be prepared by the action of the compounds of general formula H_nX (wherein X and n are as hereinbefore defined) on compounds of the general formula:

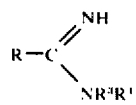

(wherein R, R³ and R¹ are as hereinbefore defined), which may themselves be prepared by the reaction of compounds of the general formula:

NHR³R¹    XVII (wherein R³ and R¹ are as hereinbefore defined) with compounds of formula XII at tempertures between, for example, 0° and 60° C. and advantageously in the presence of a suitable organic solvent, preferably a lower alkanol, e.g. ethanol.

The compounds of formula XV wherein R⁵ represents an amino group (i.e. 5-amino-4-carbamoyl-1H-1,2,3-triazole), or a hydroxy or alkoxy group, may be prepared by the methods described by J. R. E. Hoover and A. R. Day. J. Amer. Chem. Soc., 1956, 78, 5832, and A. Albert, J. Chem. Soc., 1969(C), 2076, respectively.

The compounds of formula XV wherein R⁵ represents an alkylamino or dialkylamino group may be prepared, for example, from compounds of formula XV, wherein R⁵ represents an alkoxy group, by reaction with the appropriate amine, preferably in the presence of a base, e.g. sodium ethoxide in ethanol, or alternatively by debenzylation of compounds of formula XXI depicted hereafter (wherein R⁵ represents an alkylamino or dialkylamino group and R⁷ represents a benzyl group), for example by means of sodium in liquid ammonia.

According to a further feature of the present invention, compounds of formula I, wherein that carbon atom of the group R by which the said group R is attached to the 2-position of the azapurinone ring bears no hydrogen atoms, such a group R being represented by the symbol R⁶, are prepared by the reaction of compounds of the general formula:

R⁶-CZ₃    XVIII (wherein R⁶ is as hereinbefore defined and Z is a halogen atom, preferably a chlorine atom) with 5-amino-4-carbamoyl-1H-1,2,3-triazole at elevated temperatures, preferably between 50° and 150° C. and in the presence of a base, for example potassium tert-butoxide, and a suitable solvent, for example anhydrous tert-butanol.

According to yet a further feature of the present invention, compounds of formula I are prepared by the reaction of compounds of formula XV with compounds of formula XII at elevated temperatures, preferably between 50° and 200° C, in a suitable solvent, for example anhydrous ethanol or anhydrous dimethylformamide, optionally in the presence of a suitable base, for example sodium ethoxide.

According to another feature of the present invention, compounds of formula I (wherein R is a group R⁶ as hereinbefore defined) are prepared by the reaction of compounds of the general formula:

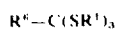   XIX (wherein R¹ and R⁶ are as hereinbefore defined) with 5-amino-4-carbamoyl-1H-1,2,3-triazole at an elevated temperature, preferably at 100° C. to 200° C, in an anhydrous inert organic solvent, for example an aromatic hydrocarbon (e.g. xylene) and in the presence of an acid (e.g. toluene-p-sulphonic acid) or a Lewis acid (e.g. boron trifluoride).

Compounds of formula XIX may be prepared by the method described by L. C. Rinzema, J. Stoffelsma and J. F. Arens, Rec. Trav. Chim., 1959, 78, 354.

According to a further feature of the present invention, compounds of formula I are prepared from compounds of the general formula:

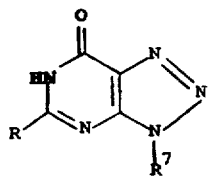   XX (wherein R is as hereinbefore defined, and R⁷ is a group heretofore used or described in the literature for the protection of nitrogen atom constituents of heterocyclic rings, for example a benzyl, toluene-p-sulphonyl or phenacylsulphonyl group, or such a group substituted by, for example, one or more alkyl groups containing from 1 to 6 carbon atoms) by known methods for the replacement of such protecting groups R⁷ by a hydrogen atom. Preferably R⁷ represents a benzyl group, which is replaced by a hydrogen atom, thus preparing compounds of formula I from the corresponding compounds of formula XX, for example by means of concentrated aqueous hydrobromic acid at elevated temperatures, by means of sodium in liquid ammonia, or otherwise by hydrogenation in the presence of a hydrogenation catalyst, for example palladium on charcoal, and in the presence of a strong acid, for example trifluoromethanesulphonic acid.

Compounds of formula XX may be prepared, for example, by the reaction of compounds of the general formula:

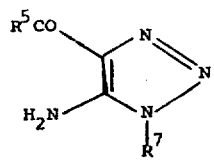   XXI (herein R⁵ and R⁷ are as hereinbefore defined) with compounds of formula XIV under similar conditions to those hereinbefore described for the preparation of compounds of formula I by the reaction of compounds of formula XV with compounds of formula XIV.

Compounds of formula XXI may be prepared by the methods described by J. R. E. Hoover and A. R. Day, J. Amer. Chem. Soc., 1956, 78, 5832, and A. Albert, J. Chem. Soc., 1969(C), 2379.

Compounds of formula XX, wherein R represents a group R⁶ as hereinbefore defined, may also be prepared by the reaction of compounds of the general formula:

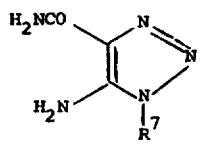   XXII (wherein R⁷ is as hereinbefore defined) with compounds of formula XIX under similar conditions to those hereinbefore described for the preparation of compounds of formula I by the reaction of 5-amino-4-carbamoyl-1H-1,2,3-triazole with compounds of formula XIX.

Compounds of formula XXII may be prepared by methods similar to those described by J. R. E. Hoover and A. R. Day (op.cit.).

Compounds of formula XX (wherein R⁷ is as hereinbefore defined) and R represents a group R⁶ as hereinbefore defined) may also be made of the reaction of compounds of formula XXII with compounds of formula XVIII at elevated temperatures, preferably between 50° and 150° C, and in the presence of a base, for example potassium tert-butoxide, and a suitable solvent, for example anhydrous tert-butanol.

Compounds of formula XX may also be prepared by the reaction of compounds of the general formula:

  RCOZ   XXIII (wherein R and Z are as hereinbefore defined) with (a) compounds of formula XXII, preferably at 10°–30° C, in the presence of a suitable catalyst, for example concentrated sulphuric acid or anhydrous pyridine; or (b) with compounds of the general formula:

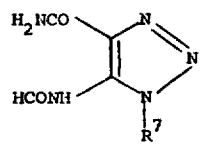   XXIV (wherein R⁷ is as hereinbefore defined), preferably at 0°–30° C, in the presence of a base, for example sodium hydroxide, and in a suitable solvent, for example water, followed by cyclisation of the resulting acylated product by heating to a temperature preferably between 50° and 150° C, in the presence of an acid or preferably in the presence of a base, for example the hydroxide, carbonate or bicarbonate of sodium or potassium, in a suitable solvent, for example aqueous ethanol of water, or an alkoxide (preferably the methoxide or ethoxide) of sodium or potassium in a dry alkanol (preferably methanol or ethanol).

Compounds of formula XXIV may be prepared by the method described by A. Albert, J. Chem. Soc., 1969(c), 152.

Compounds of formula XX may also be prepared by the reaction of compounds of formula XXI with compounds of general formula XII at elevated temperatures, preferably between 50° and 200° C, in a suitable solvent, for example anhydrous ethanol, optionally in the presence of a suitable base, for example sodium ethoxide.

According to a further feature of the present invention, compounds of formula I are prepared by the reaction of 5-amino-4-carbamoyl-1H-1,2,3-triazole with compounds of formula XXIII, preferably at 10°–30+ C in the presence of a suitable catalyst, for example concentrated sulphuric acid or anhydrous pyridine, followed by cyclisation of the resulting acylated product, preferably by heating to a temperature between 50° and 150° C. in the presence of an acid or preferably in the presence of a base for example sodium carbonate or potassium carbonate) in a suitable solvent, for example aqueous ethanol or water.

According to a further feature of the present invention, compounds of formula I are prepared from compounds of the general formula:

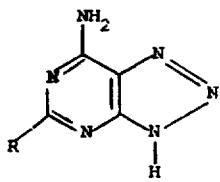

XXV (wherein R is as hereinbefore defined) by the action of a source of nitrous acid, for example a nitrite of an alkali metal, e.g. sodium nitrite or potassium nitrite, together with an acid, for example dilute aqueous hydrochloric acid, preferably as the reaction medium, at an elevated temperature, preferably between 60° and 100° C.

Compounds of formula XXV may be prepared, for example, from compounds of the general formula:

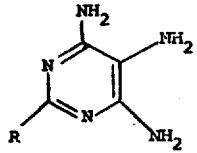

XXVI (wherein R is as hereinbefore defined) by the action of a source of nitrous acid, for example a nitrite of an alkali metal, e.g. sodium nitrite or potassium nitrite, together with an acid, for example dilute aqueous hydrochloric acid, preferably as the reaction medium, at a temperature near or below the ambient temperature, for example between 0° and 30° C.

Compounds of formula XXVI may be prepared by the application or adaptation of known methods, for example by the method of J. Weinstock, R. Y. Dunoff and J. G. Williams, J. Medicin. Chem., 1968, 11, 542.

It will be readily appreciated by those skilled in the art that interconversions between different compounds of formula I are possible, for example:

a. compounds of formula I wherein R represents a substituted or unsubstituted phenyl or naphthyl group may be converted to corresponding nitrophenyl or nitronaphthyl compounds of formula I by the application of methods known per se for the nitration of phenyl and naphthyl moieties, b. nitro-compounds of formula I as formed in (a) may be converted to the corresponding amino compounds by reduction, for example by catalytic hydrogenation using, for example, a platinum oxide-charcoal catalyst, or c. compounds of formula I wherein R represents a substituted or unsubstituted benzyloxyphenyl group may be converted to the corresponding hydroxy-phenyl compounds of formula I by reduction, for example by catalytic hydrogenation using, for example, a palladium-charcoal catalyst.

By the terms "known methods" and "methods known per se" as used in this Specification is meant methods heretofore employed or described in the literature.

The 8-azapurin-6-ones of the present invention possess valuable pharmacological properties, in particular properties of value in the treatment of respiratory disorders manifested by the interaction of tissue-fixed antibodies with specific antigens, such as allergic bronchial asthma.

In pharmacological tests the new compounds suppress the passive cutaneous anaphylactic (PCA) reaction resulting from combination of tissue-fixed fixed reaginic antibodies with the appropriate antigenic material (termed reagin-allergen combination) and carried out in an essentially similar manner to that described by Ogilvie [Nature (Lond.), (1964), 204, 91–92; Immunology, (1967), 12, 112–131]. In the method used to test these compounds sera were obtained from rats which had been infected with larvae of the nematode parasite *Nippostrongylus brasiliensis*; as a result of the parasitic infestation reaginic antibodies are elaborated in the host mammal and are found in sera removed from such animals. Other, non-infected, rats received intradermal injections of appropriate dilutions of such sera and were then given the allergenic material along with Evans' blue dye intravenously forty-eight hours later.

The allergenic material consisted of supernatant fluid after centrifugation of homogenates of adult *Nippostrongylus brasiliensis* worms which had been macerated in Tyrode's solution. The sites of PCA reactions were visualised by the effusion of Evans' blue dye from the circulation into those areas as a result of increased capillary permeability caused by the release of biologically-active substances from cells where reagin-allergen combination had occurred. The new compounds when given intravenously to the rats just before injection of allergen, at doses of, for example, 0.01–20 mg/kg, or administered orally fifteen or forty-five minutes before intravenous injection of allergen at doses of, for example, 0.5–200 mg/kg were able to prevent the development of the reaction.

In biochemical tests the new compounds inhibit the hydrolysis of adenosine cyclic 3',5'-monophosphate (cyclic AMP) to adenosine 5'-monophosphate by human lung microsomal cyclic nucleotide phosphodiesterase. In a test carried out in an essentially similar manner to the described by G. Brooker, L. J. Thomas and M. M. Appleman, Biochemistry, 1968, 7 (12), 4177, the $^3$H-adenosine 5'-monophosphate obtained, by the action of microsomes of human lung tissue, from $^3$H-cyclic AMP was converted to $^3$H-adenosine and phosphate by means of 5'-nucleotidase. Dowex 2-X8 anion exchange resin was used to adsorb unchanged ³H-cyclic AMP, thus terminating the enzyme reaction, and the ³H-adenosine in solution was measured by means of radioactive scintillation counting.

In the method used, a mixture (0.20 ml) consisting of microsomes prepared from macroscopically normal human lung tissue obtained from surgical operations, ³H-cyclic AMP (10⁻⁷M), magnesium sulphate (5mM), 5'-nucleotidase (0.1 mg) and a new compound of the present invention, contained in a trishydroxymethylmethylammonium hydrochloride buffer (0.1 M, pH 7.5), was incubated for 15 minutes at 37° C. The enzyme reaction was then terminated, by the addition of Dowex 2-X8 anion exchange resin (0.5 g) and scintillation fluid (10 ml of a 0.5% solution of 2,5-diphenyloxazole in a 1:2 mixture of Triton X-100 and toluene) was added and the ³H-adenosine measured by counting the scintillation produced by the tritium (³H). The estimation was repeated, using various concentrations of the new compounds of formula I, and compared with the result obtained in the absence of the new compounds.

The new compounds caused 50% inhibition of the hydrolysis caused by the phosphodiesterase at concentrations of, for example, $5 \times 10^{-6}$ to $5 \times 10^{-3}$M.

Preferred compounds of the present invention are those 8-azapurin-6-one derivatives of general formula I wherein R represents a phenyl or naphthyl group which may optionally carry one, two or three substituents selected from halogen atoms, and hydroxy, alkyl, phenylalkyl, alkoxy, alkenyloxy, alkoxyalkoxy, phenoxy, phenoxy substituted by an alkoxy group, aralkoxy, alkylthio, nitro, alkanesulphonyl, amino, trifluoromethyl, methylenedioxy, and dialkylamino groups, or R represents a cycloalkyl group containing 3 to 8 carbon atoms, a straight- or branched-chain alkyl group containing from 2 to 10 carbon atoms, or a straight- or branched-chain alkyl group containing 1 to 10 carbon atoms carrying one or two substituents selected from halogen atoms, hydroxy, alkoxy groups containing from 1 to 6 carbon atoms, cycloalkyl groups containing 3 to 8 carbon atoms and phenyl groups. Of such compounds those of outstanding importance are the 8-azapurin-6-one derivatives represented by the general formula:-

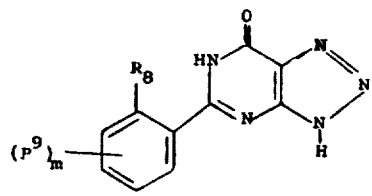

wherein $R^8$ represents a hydroxy group, a straight- or branched-chain alkoxy group containing from 1 to 6 carbon atoms, a straight- or branched-chain alkenyloxy group containing from 2 to 6 carbon atoms or an aralkoxy (e.g. phenylalkoxy) group in which the alkoxy portion contains from 1 to 6 carbon atoms and may be straight- or branched-chain, for example a benzyloxy group, $R^9$ represents a fluorine, chlorine or bromine atom, a trifluoromethyl group, a hydroxy group, a nitro group, a straight- or branched- chain alkyl or alkoxy group containing from 1 to 6 carbon atoms, or an aralkoxy (e.g. phenylalkoxy) group in which the alkoxy portion contains from 1 to 6 carbon atoms and may be straight- or branched- chain, for example a benzyloxy group, and m represents 0, 1 or 2, the atoms or groups represented by the symbol $R^9$ being the same or different when m represents 2, and their pharmaceutically acceptable salts.

The most important compounds of general formula XXVII are 8-aza-2-(2-hydroxyphenyl)purin-6-one, 8-aza-2-(2-ethoxyphenyl)purin-6-one, 8-aza-2-(2-isopropoxyphenyl)purin-6-one, 8-aza-2-(2-n-butoxyphenyl)purin-6-one, 8-aza-2-(2-sec-butoxyphenyl)purin-6-one, 8-aza-2-(2-isobutoxyphenyl)purin-6-one, 8-aza-2(2-n-pentyloxyphenyl)purin-6-one, 8-aza-2-(2-isopentyloxyphenyl)purin-6-one, 8-aza-2-(5-tert-butyl-2-methoxyphenyl)purin-6-one, 8-aza-2-(2-n-hexyloxyphenyl)purin-6-one, 8-aza-2-(2-benzyloxyphenyl)purin-6-one, 8-aza-2-(5-hydroxy-2-methoxyphenyl)purin-6-one, 8-aza-2-(2,4-dimethoxyphenyl)purin-6-one, 8-aza-2-(2,5-dimethoxyphenyl)purin-6-one, 8-aza-2-(2,5-dibenzyloxyphenyl)purin-6-one, 8-aza-2-(5-benzyloxy-2-methoxyphenyl)purin-6-one, 8-aza-2-(2,5-dihydroxyphenyl)purin-6-one, 8-aza-2-(2-methoxy-5-methylphenyl)purin-6-one, 8-aza-2-(2-methoxy-5-nitrophenyl)purin-6-one, 8-aza-2-(2-methoxy-3,5-dinitrophenyl)purin-6-one, 8-aza-2-(2-methoxy-5-trifluoromethylphenyl)purin-6-one, 8-aza-2-(2-methoxy-3,5-dimethylphenyl)purin-6-one, 8-aza-2-(2-allyloxyphenyl)purin-6-one, and especially 8-aza-2-(2-methoxyphenyl)purin-6-one and 8-aza-2-(2-propoxyphenyl)-purin-6-one, and their pharmaceutically acceptable salts.

Other important compounds according to the present invention are 8-aza-2-phenylpurin-6-one, 8-aza-2-(3-n-hexyloxyphenyl)purin-6-one, 8-aza-2-(3-trifluoromethylphenyl)purin-6-one, 8-aza-2-(3-methylphenyl)purin-6-one, and their pharmaceutically acceptable salts.

The following Examples illustrate the preparation of the 8-azapurin-6-one derivatives of the present invention.

EXAMPLE 1

A solution of concentrated hydrochloric acid (50 ml.) in water (50 ml.) was stirred and maintained at 0° C. and treated with sodium nitrite (1.5 g.). The resultant solution was stirred and maintained at 0° C. and treated with 4,5-diamino-2-(2-methoxyphenyl)-pyrimid-6-one (2.54 g.) during 30 minutes, followed by a further quantity of sodium nitrite (1.5 g.). The stirred mixture was then allowed to warm to room temperature, when the solid was filtered off, washed with water and dissolved in a dilute aqueous solution of ammonia. The solution was filtered and brought to pH6 by the addition of glacial acetic acid. The resultant solid was filtered off, washed well with water, sucked dry, and recrystallised from methanol to give 8-aza-2-(2-methoxyphenyl)purin-6-one (1.9 g.), m.p. 239° C. (with decomposition).

Further purification was effected by recrystallisation of an aliquot from pyridine, followed by washing with dilute hydrochloric acid and with water, to give 8-aza-2-(2-methoxyphenyl)purin-6-one, m.p. 254°–255° C. (with decomposition).

By proceeding in a similar manner, but substituting 4,5-diamino-2-(3-methoxyphenyl)pyrimid-6-one, 4,5-diamino-2-(4-methoxyphenyl)pyrimid-6-one, 4,5-diamino-2-phenylpyrimid-6-one, 4,5-diamino-2-(2-tolyl)pyrimid-6-one, 4,5-diamino-2-(3-tolyl)pyrimid-6-one, 4,5-diamino-2-(4-tolyl)pyrimid-6-one, 4,5-diamino-2-(2-chlorophenyl)pyrimid-6-one, 4,5- diamino-2-(4-chlorophenyl)pyrimid-6-one, 4,5-diamino-2-(2-bromophenyl)pyramid-6-one, 4,5-diamino-2-(2-fluorophenyl)pyrimid-6-one, 4,5-diamino-2-(4-hydroxyphenyl)pyrimid-6-one, crude 4,5-diamino-2-(2-ethoxyphenyl)pyrimid-6-one, crude 4,5-diamino-2-(2-propoxyphenyl)pyrimid-6-one, crude 4,5-diamino-2-(2-isopropoxyphenyl)pyrimid-6-one, crude 4,5-diamino-2-(2-butoxyphenyl)pyrimid-6-one, 4,5-diamino-2-(2isobutoxyphenyl)pyrimid-6-one, crude 4,5-diamino-2-(2-sec-butoxyphenyl)pyrimid-6-one, 4,5-diamino-2-(2-pentyloxyphenyl)pyrimid-6-one, 4,5-diamino-2-(2-isopentyloxyphenyl)pyrimid-6-one, 4,5-diamino-2-(2-hexyloxyphenyl)pyrimid-6-one, 4,5-diamino-2-(3-hexyloxyphenyl)pyrimid-6-one, 4,5-diamino-2-(4-hexyloxyphenyl)pyrimid-6-one, crude 4,5-diamino-2-[2-(2-ethoxyethoxy)phenyl]pyrimid-6-one, crude 4,5-diamino-2-(2-methylmercaptophenyl)pyrimid-6-one, 4,5-diamino-2-(3-methylmercaptophenyl)pyrimid-6-one, 4,5-diamino-2-(2-phenoxyphenyl)pyrimid-6-one, 4,5-diamino-2-[2-(4-methoxyphenoxy)phenyl]pyrimid-6-one, 4,5-diamino-2-(2-benzyloxyphenyl)pyrimid-6-one, 4,5-diamino-2-(2-methanesulphonylphenyl)pyrimid-6-one, 4,5-diamino-2-(4-methanesulphenylphenyl)pyrimid-6-one, 4,5-diamino-2-(2-butanesulphonylphenyl)pyrimid-6-one, 4,5-diamino-2-(3-trifluoromethylphenyl)pyrimid-6-one, crude 4,5-diamino-2-(2-dimethylaminophenyl)pyrimid-6-one, 4,5-diamino-2-(3-dimethylaminophenyl)pyrimid-6-one, 4,5-diamino-2-(2,3-dimethoxyphenyl)pyrimid-6-one, 4,5-diamino-2-(2,4-dimethoxyphenyl)pyrimid-6-one, 4,5-diamino-2-(2,5-dimethoxyphenyl)pyrimid-6-one, 4,5-diamino-2-(2,6-dimethoxyphenyl)pyrimid-6-one, 4,5-diamino-2-(3,4-dimethoxyphenyl)pyrimid-6-one, 4,5-diamino-2-(3,5-dimethoxyphenyl)pyrimid-6-one, crude 4,5-diamino-2-(4-benzyloxy-2-methoxyphenyl)pyrimid-6-one, 4,5-diamino-2-(5-benzyloxy-2-methoxyphenyl)pyrimid-6-one, 4,5-diamino-2-(2,5-dibenzyloxyphenyl)pyrimid-6-one, crude 4,5-diamino-2-(2-methoxy-5-trifluoromethylphenyl)pyrimid-6-one, crude 4,5-diamino-2-(2,3-methylenedioxyphenyl)pyrimid-6-one, 4,5-diamino-2-(1-naphthyl)pyrimid-6-one and 4,5-diamino-2-(2-naphthyl)pyrimid-6-one for the 4,5-diamino-2-(2-methoxyphenyl)pyrimid-6-one used as a starting material in the above preparation, there were prepared 8-aza-2-(3-methoxyphenyl)purin-6-one, m.p. 272°–273° C. (with decomposition), 8-aza-2-(4-methoxyphenyl)purin-6-one, m.p. 272° C. (with decomposition), 8-aza-2-phenylpurin-6-one, m.p. 280°C. (with decomposition), 8-aza-2-(2-tolyl)purin-6-one, m.p. 263°–265° C., 8-aza-2-(3-tolyl)purin-6-one (which contained 0.25 moles of water of crystallisation), m.p. 280°–281° C., 8-aza-2-(4-tolyl)purin-6-one, m.p. 285°–287° C., 8-aza-2-(2-chlorophenyl)purin-6-one, m.p. 268°–270° C., 8-aza-2-(4-chlorophenyl)purin-6-one, m.p. 294° C. (with decomposition), 8-aza-2-(2-bromophenyl)purin-6-one, m.p. 247°–250° C., 8-aza-2-(2-fluorophenyl)purin-6-one, m.p. 251.5°–252.5° C., 8-aza-2-(4-hydroxyphenyl)purin-6-one (which contained 0.2 moles of acetic acid of crystallisation), m.p. 330° C. (with decomposition), 8-aza-2-(2-ethoxyphenyl)purin-6-one, m.p. 216°–218° C. (with decomposition), 8-aza-2-(2-propoxyphenyl)purin-6-one, m.p. 238°–240° C., 8-aza-2-(2-isopropoxyphenyl)purin-6-one, m.p. 218°–219° C. (with decomposition), 8-aza-2-(2-butoxyphenyl)purin-6-one, m.p. 188°–190° C., 8-aza-2-(2-iso-butoxyphenyl)purin-6-one, m.p. 226°–227° C. (with decomposition), 8-aza-2-(2-sec-butoxyphenyl)purin-6-one, m.p. 205°–208° C. (with decomposition), 8-aza-2-(2-pentyloxyphenyl)purin-6-one, m.p. 175°–176° C., 8-aza-2-(2-isopentyloxyphenyl)purin-6-one, m.p. 186°–188° C. (with decomposition), 8-aza-2-(2-hexyloxyphenyl)purin-6-one, m.p. 130°–132° C., 8-aza-2-(3-hexyloxyphenyl)purin-6-one, m.p. 220°–221° C., 8-aza-2-(4-hexyloxyphenyl)purin-6-one, m.p. 225° C. (with decomposition), 8-aza-2-[2-(2-ethoxyethoxy)phenyl]purin-6-one, m.p. 162°–164° C., 8-aza-2-(2-methylmercaptophenyl)purin-6-one monohydrate, m.p. 223°–226° C., 8-aza-2-(3-methylmercaptophenyl)purin-6-one (which contained 0.75 moles of water of crystallisation), m.p. 278.5°–280° C., 8-aza-2-(2-phenoxyphenyl)purin-6-one, m.p. 224°–227° C., 8-aza-2-[2-(4-methoxyphenoxy)phenyl]purin-6-one monohydrate, m.p. 249°–250° C., 8-aza-2-(2-benzyloxyphenyl)purin-6-one, m.p. 240°–242° C. (with decomposition), 8-aza-2-(2-methanesulphonylphenyl)purin-6-one, m.p. 274°–275° C. (with decomposition), 8-aza-2-(4-methanesulphonylphenyl)purin-6-one, m.p. 310°–315° C. (with decomposition), 8-aza-2-(2-butanesulphonylphenyl)purin-6-one, m.p. 282° C. (with decomposition), 8-aza-2-(3-trifluoromethylphenyl)purin-6-one, m.p. 268° C. (with decomposition), 8-aza-2-(2-dimethylaminophenyl)purin-6-one, m.p. 250°–251° C. (with decomposition), 8-aza-2-(3-dimethylaminophenyl)purin-6-one, m.p. 273°–275° C., 8-aza-2-(2,3-dimethoxyphenyl)purin-6-one, m.p. 252°–254° C. (with decomposition), 8-aza-2-(2,4-dimethoxyphenyl)purin-6-one, m.p. 257°–258° C. (with decomposition), 8-aza-2-(2,5-dimethoxyphenyl)purin-6-one, m.p. 252°–255° C. (with decomposition), 8-aza-2-(2,6-dimethoxyphenyl)purin-6-one, m.p. 274°–276° C. (with decomposition), 8-aza-2-(3,4-dimethoxyphenyl)purin-6-one, m.p. 299°–300° C. (with decomposition), 8-aza-2-(3,5-dimethoxyphenyl)purin-6-one, m.p. 270°–272° C. (with decomposition), 8-aza-2-(4-benzyloxy-2-methoxyphenyl)purin-6-one, m.p. 242°–244° C., 8-aza-2-(5-benzyloxy-2-methoxyphenyl)purin-6-one, m.p. 258°–260° C., 8-aza-2-(2,5-dibenzyloxyphenyl)purin-6-one, m.p. 212°–214° C., 8-aza-2-(2-methoxy-5-trifluoromethylphenyl)purin-6-one, m.p. 221°–223° C., 8-aza-2-(2,3-methylenedioxyphenyl)purin-6-one, m.p. 269°–271° C. (with decomposition), 8-aza-2-(1-naphthyl)purin-6-one hemihydrate, m.p. 272°–274° C., and 8-aza-2-(2-naphthyl)purin-6-one monohydrate, m.p. 300° C. (with decomposition), respectively.

The 4,5-diamino-2-(2-methoxyphenyl)pyrimid-6-one, used as a starting material in the above preparation, was prepared as follows:

Sodium dithionite (8.7 g.) was added slowly to a stirred mixture of 4-amino-2-(2-methoxyphenyl)-5-nitrosopyrimid-6-one (6.15 g.) and water (90 ml.) at 70°–80° C., and stirring at that temperature was continued for a further 50 minutes. The mixture was then cooled, the yellow solid was filtered off, washed with water and dried to give 4,5-diamino-2-(2-methoxyphenyl)pyrimid-6-one (2.54 g.), m.p. 222°–223° C. (with decomposition), pure enough for use as a starting material in the next stage of the synthesis. Recrystallisation of a sample from ethanol gave analytically pure 4,5-diamino-2-(2-methoxyphenyl)pyrimid-6-one, m.p. 223°–224° C. (with decomposition).

By proceeding in a similar manner, but substituting 4-amino-2-(3-methoxyphenyl)-5-nitrosopyrimid-6-one, 4-amino-2-(4-methoxyphenyl)-5-nitrosopyrimid-6-one, 4-amino-5-nitroso-2-phenylpyrimid-6-one, 4-amino-5-nitroso-2-(2-tolyl)pyrimid-6-one, 4-amino-5-nitroso-2-(3-tolyl)pyrimid 6-one, crude 4-amino-5-nitroso-2-(4-tolyl)pyrimid-6-one, crude 4-amino-2-(2-chlorophenyl)-5-nitrosopyrimid-6-one, 4-amino-2-(4-chlorophenyl)-5-nitrosopyrimid-6-one, 4-amino-2-(2-bromophenyl)-5-nitrosopyrimid-6-one, 4-amino-2-(2-fluorophenyl)-5-nitrosopyrimid-6-one, 4-amino-2-(4-hydroxyphenyl)-5-nitrosopyrimid-6-one, 4-amino-2-(2-ethoxyphenyl)-5-nitrosopyrimid-6-one, 4-amino-5-nitroso-2-(2-propoxyphenyl)pyrimid-6-one, 4-amino-2-(2-isopropoxyphenyl)-5-nitrosopyrimid-6-one, crude 4-amino-2-(2-butoxyphenyl)-5-nitrosopyrimid-6-one, 4-amino-2-(2-isobutoxyphenyl)-5-nitrosopyrimid-6-one, 4-amino-2-(2-sec-butoxyphenyl)-5-nitrosopyrimid-6-one, 4-amino-5-nitroso-2-(2-pentyloxyphenyl)pyrimid-6-one, 4-amino-2-(2-isopentyloxyphenyl)-5-nitrosopyrimid-6-one, 4-amino-2-(2-hexyloxyphenyl)-5-nitrosopyrimid-6-one, 4-amino-2-(3-hexyloxyphenyl)-5-nitrosopyrimid-6-one, 4-amino-2-(4-hexyloxyphenyl)-5-nitrosopyrimid-6-one, 4-amino-2-[2-(2-ethoxyethoxy)phenyl]-5-nitrosopyrimid-6-one, 4-amino-2-(2-methylmercaptophenyl)-5-nitrosopyrimid-6-one, 4-amino-2-(3-methylmercaptophenyl)-5-nitrosopyrimid-6-one, 4-amino-5-nitroso-2-(2-phenoxyphenyl)pyrimid-6-one, crude 4-amino-2-[2-(4-methoxyphenoxy)phenyl]-5-nitrosopyrimid-6-one, 4-amino-2-(2-benzyloxyphenyl)-5-nitrosopyrimid-6-one, 4-amino-2-(2-methanesulphonylphenyl)-5-nitrosopyrimid-6-one, 4-amino-2-(4-methanesulphonylphenyl)-5-nitrosopyrimid-6-one, 4-amino-2-(2-butanesulphonylphenyl)-5-nitrosopyrimid-6-one, 4-amino-5-nitroso-2-(3-trifluoromethylphenyl)pyrimid-6-one, 4-amino-2-(2-dimethylaminophenyl)-5-nitrosopyrimid-6-one, 4-amino-2-(3-dimethylaminophenyl)-5-nitrosopyrimid-6-one, crude 4-amino-2-(2,3-dimethoxyphenyl)-5-nitrosopyrimid-6-one, 4-amino-2-(2,4-dimethoxyphenyl)-5-nitrosopyrimid-6-one, 4-amino-2-(2,5-dimethoxyphenyl)-5-nitrosopyrimid-6-one, 4-amino-2-(2,6-dimethoxyphenyl)-5-nitrosopyrimid-6-one, 4-amino-2-(3,4-dimethoxyphenyl)-5-nitrosopyrimid-6-one, crude 4-amino-2-(3,5-dimethoxyphenyl)-5-nitrosopyrimid-6-one, crude 4-amino-2-(4-benzyloxy-2-methoxyphenyl)-5-nitrosopyrimid-6-one, 4-amino-2-(5-benzyloxy-2-methoxyphenyl)-5-nitrosopyrimid-6-one, 4-amino-2-(2,5-dibenzyloxyphenyl)-5-nitrosopyrimid-6-one, crude 4-amino-2-(2-methoxy-5-trifluoromethylphenyl)-5-nitrosopyrimid-6-one, 4-amino-2-(2,3-methylenedioxyphenyl)-5-nitrosopyrimid-6-one, 4-amino-2-(1-naphthyl)-5-nitrosopyrimid-6-one, and 4-amino-2-(2-naphthyl)-5-nitrosopyrimid-6-one, for the 4-amino-2-(2-methoxyphenyl)-5-nitrosopyrimid-6-one used as a starting material in the above preparation, there were prepared:

4,5-diamino-2-(3-methoxyphenyl)pyrimid-6-one, m.p. 223°–225° C. (with decomposition), 4,5-diamino-2-(4-methoxyphenyl)pyrimid-6-one, m.p. 255° C. (with decomposition), 4,5-diamino-2-phenylpyrimid-6-one, m.p. 236° C. (with decomposition), 4,5-diamino-2-(2-tolyl)pyrimid-6-one hemihydrate, m.p. 133°–135° C., 4,5-diamino-2-(3-tolyl)pyrimid-6-one, m.p. 273°–275° C., 4,5-diamino-2-(4-tolyl)pyrimid-6-one, m.p. 224°–230° C., 4,5-diamino-2-(2-chlorophenyl)pyrimid-6-one (which contained 0.25 moles of water of crystallisation), m.p. 126°–130° C., 4,5-diamino-2-(4-chlorophenyl)pyrimid-6-one, m.p. 279°–283° C. (with decomposition), 4,5-diamino-2-(2-bromophenyl)pyrimid-6-one, m.p. 137°–140° C., 4,5-diamino-2-(2-fluorophenyl)pyrimid-6-one, m.p. 240°–242° C., 4,5-diamino-2-(4-hydroxyphenyl)pyrimid-6-one, m.p. above 300° C., crude 4,5-diamino-2-(2-ethoxyphenyl)-pyrimid-6-one [characterised as the monohydrochloride dihydrate, m.p. 139°–143° C. (with decomposition)], crude 4,5-diamino-2-(2-propoxyphenyl)pyrimid-6-one, crude 4,5-diamino-2-(2-isopropoxyphenyl)-pyrimid-6-one [characterised as the picrate containing 0.5 moles of acetic acid of crystallisation, m.p. 192°–193° C. (with decomposition)], crude 4,5-diamino-2-(2-butoxyphenyl)pyrimid-6-one, 4,5-diamino-2-(2-isobutoxyphenyl)pyrimid-6-one, m.p. 164°–166° C. (with decomposition), crude 4,5-diamino-2-(2-sec-butoxyphenyl)pyrimid-6-one, 4,5-diamino-2-(2-pentyloxyphenyl)pyrimid-6-one, m.p. 144°–145° C., 4,5-diamino-2-(2-isopentyloxyphenyl)-pyrimid-6-one, m.p. 172°–174° C., 4,5-diamino-2-(2-hexyloxyphenyl)pyrimid-6-one, m.p. 150°–152° C. (with decomposition), 4,5-diamino-2-(3-hexyloxyphenyl)pyrimid-6-one, m.p. 156°–157° C., 4,5-diamino-2-(4-hexyloxyphenyl)pyrimid-6-one, m.p. 175°–176° C., crude 4,5-diamino-2-[2-(2-ethoxyethoxy)phenyl]pyrimid-6-one, 4,5-diamino-2-(2-methylmercaptophenyl)pyrimid-6-one, m.p. 227°–229° C., 4,5-diamino-2-(3-methylmercaptophenyl)pyrimid-6-one, m.p. 246°–250° C. (with decomposition), 4,5-diamino-2-(2-phenoxyphenyl)-pyrimid-6-one, m.p. 101°–104° C., 4,5-diamino-2-[2-(4-methoxyphenoxy)phenyl]-pyrimid-6-one, m.p. 195°–200° C., 4,5-diamino-2-(2-benzyloxyphenyl)pyrimid-6-one, m.p. 165°–167° C. (with decomposition), 4,5-diamino-2-(2-methanesulphonylphenyl)pyrimid-6-one, m.p. 262°–265° C., 4,5-diamino-2-(4-methanesulphonylphenyl)pyrimid-6-one, m.p. 282°–285° C. (with decomposition), 4,5-diamino-2-(2-butanesulphonylphenyl)pyrimid-6-one, m.p. 236°–237° C., 4,5-diamino-2-(3-trifluoromethylphenyl)pyrimid-6-one, m.p. 235°–238° C., crude 4,5-diamino-2-(2-dimethylaminophenyl)pyrimid-6-one, 4,5-diamino-2-(3-dimethylaminophenyl)pyrimid-6-one hemihydrate, m.p. 127°–130° C., 4,5-diamino-2-(2,3-dimethoxyphenyl)pyrimid-6-one, m.p. 74°–76° C., 4,5-diamino-2-(2,4-dimethoxyphenyl)pyrimid-6-one, m.p. 193° C. (with decomposition), 4,5-diamino-2-(2,5-dimethoxyphenyl)pyrimid-6-one, m.p. 198°–200° C., 4,5-diamino-2-(2,6-dimethoxyphenyl)pyrimid-6-one, m.p. 214°–216° C., 4,5-diamino-2-(3,4-dimethoxyphenyl)pyrimid-6-one, m.p. 245°–249° C. (with decomposition), 4,5-diamino-2-(3,5-dimethoxyphenyl)-pyrimid-6-one, m.p. 235°–240° C. (with decomposition), crude 4,5-diamino-2-(4-benzyloxy-2-methoxyphenyl)pyrimid-6-one, 4,5-diamino-2-(5-benzyloxy-2-methoxyphenyl)pyrimid-6-one, m.p. 204°–208° C., 4,5-diamino-2-(2,5-dibenzyloxyphenyl)pyrimid-6-one, m.p. 128°–132° C., crude 4,5-diamino-2-(2-methoxy-5-trifluoromethylphenyl)-pyrimid-6-one, crude 4,5-diamino-2-(2,3-methylenedioxyphenyl)pyrimid-6-one, 4,5-diamino-2-(1-naphthyl)pyrimid-6-one, m.p. 246°–248° C., and 4,5-diamino-2-(2-naphthyl)pyrimid-6-one, m.p. 257°–258° C., respectively.

The 4,5-diamino-2-(2-methoxyphenyl)pyrimid-6-one, used as a starting material in the above preparation, was alternatively prepared as follows:

4-Amino-2-(2-methoxyphenyl)-5-nitrosopyrimid-6-one (56 g.) was suspended in water (2000 ml.). Triethylamine (50 ml.) was added, and the mixture was stirred at room temperature for 30 minutes. Undissolved starting material (4 g.) was removed by filtration, the filtrate was cooled in ice-water and sodium dithionite (75 g.) was added in portions during 20 minutes with stirring, keeping the temperature of the mixture below 10° C. After stirring for a further 90 minutes at 0°–10° C., the 4,5-diamino-2-(2-methoxyphenyl)-pyrimid-6-one (47 g.), m.p. 208°–210° C. (with decomposition), was filtered off, washed with water, and dried in vacuo. This material was pure enough for use as a starting material in the next stage of the synthesis.

The 4-amino-2-(2-methoxyphenyl)-5-nitrosopyrimid-6-one, used as a starting material in the above preparations was prepared as follows:

A stirred solution of sodium methoxide in dry methanol [prepared from sodium (10.7 g.) and dry methanol (150 ml.)] maintained at 0° C. was treated with 2-methoxybenzamidine hydrochloride (21.6 g.) followed by ethyl α-oximinocyanoacetate (16.5 g.). The mixture was then heated to reflux with stirring for 4.5 hours, and then poured into water (1000 ml.) and brought to pH6 by the addition of glacial acetic acid. The resultant green solid was filtered off and recrystallised from aqueous acetic acid to give 4-amino-2-(2-methoxyphenyl)-5-nitrosopyrimid-6-one (19.2 g.), m.p. 210°–211° C. (with decomposition). A further quantity of less pure 4-amino-2-(2-methoxyphenyl)-5-nitrosopyrimid-6-one (2.9 g.) was obtained by concentration of the mother liquors of the recrystallisation.

By proceeding in a similar manner, but substituting 3-methoxybenzamidine, 4-methoxybenzamidine hydrochloride, benzamidine hydrochloride (prepared as described by P. E. Fanta & E. A. Hedman, J.Amer.-Chem.Soc., 1956, 78, 1434), 2-toluamidine (prepared as described by J. Weinstock, R. Y. Dunoff & J. G. Williams, J. Medicin. Chem., 1968, 11, 542), 3-toluamidine hydrochloride (prepared as described by J. B. Ekeley, D. V. Tieszen & A. Ronzio, J. Amer. Chem. Soc., 1935, 57, 381), 4-toluamidine hydrochloride (prepared as described by A. V. Kirsanov & T. M. Polyakova, Bull.Soc.Chim. France, 1936, (5) 3, 1600), 2-chlorobenzamidine hydrochloride (prepared as described by L. Weintraub, S. R. Oles and N. Kalish, J.Org.Chem., 1968, 33, 1679), 4-chlorobenzamidine hydrochloride (prepared as described by P. E. Fanta & E. A. Hedman, J.Amer.Chem.Soc., 1956, 78, 1434), 2-bromobenzamidine hydrochloride, 2-fluorobenzamidine hydrochloride, 4-hydroxybenzamidine hydrochloride (prepared as described by M. W. Partridge & W. F. Short, J.Chem.Soc., 1947, 390), 2-ethoxybenzamidine (prepared as described by L. Weintraub, S. R. Oles & N. kalish, J.Org.Chem., 1968, 33, 1679), 2-propoxybenzamidine hydrochloride, crude 2-isopropoxybenzamidine, crude 2-butoxybenzamidine fluorosulphonate, crude 2-isobutoxybenzamidine, crude 2-sec-butoxybenzamidine, crude 2-pentyloxybenzamidine, 2-iso-pentyloxybenzamidine hydrochloride, 2-hexyloxybenzamidine hydrochloride, crude 3-hexyloxybenzamidine, 4-hexyloxybenzamidine hydrochloride (which contained 0.25 moles of water of crystallisation), 2-(2-ethoxyethoxy)benzamidine hydrochloride, 2-methylmercaptobenzamidine hydrochloride, 3-methylmercaptobenzamidine hydrochloride, crude 2-phenoxybenzamidine, crude 2-(4-methoxyphenoxy)benzamidine, crude 2-benzyloxybenzamidine, 2-methanesulphonylbenzamidine, 4-methanesulphonylbenzamidine hydrochloride (prepared as described by P. Oxley, M. W. Partridge, T. D. Robson & W. F. Short, J.Chem.Soc., 1946, 763), 2-butanesulphonylbenzamidine hydrochloride, crude 3-trifluoromethylbenzamidine, crude 2-dimethylaminobenzamidine, all 3-dimethylaminobenzamide hydrochloride, 2,3-dimethoxybenzamidine fluorosulphonate, 2,4-dimethoxybenzamidine fluorosulphonate, 2,5-dimethoxybenzamidine, 2,6-dimethoxybenzamidine, 3,4-dimethoxybenzamidine hydrochloride (prepared as described by A. P. T. Easson & F. L. Pyman, J.Chem.-Soc., 1931, 2991), 3,5-dimethoxybenzamidine fluorosulphonate, crude 4-benzyloxy-2-methoxybenzamidine, crude 5-benzyloxy-2-methoxybenzamidine, 2,5-dibenzyloxybenzamidine, crude 2-methoxy-5-trifluoromethylbenzamidine, crude 2,3-methylenedioxybenzamidine, 1-naphthamidine hydrochloride (prepared as described by P. Oxley & W. F. Short, J.Chem.-Soc., 1946, 147) and 2-naphthamidine hydrochloride (prepared as described by A. Pinner, F. Klein & P. Lohmann, Ber. 1873, 11, 1475) for the 2-methoxybenzamidine hydrochloride used as a starting material in the above preparation, there were prepared:

4-amino-2-(3-methoxyphenyl)-5-nitrosopyrimid-6-one, m.p. 259° C. (with decomposition), 4-amino-2-(4-methoxyphenyl)-5-nitrosopyrimid-6-one, m.p. 275°–278° C. (with decomposition), 4-amino-5-nitroso-2-phenylpyrimid-6-one, m.p. 261°–262° C. (with decomposition), 4-amino-5-nitroso-2-(2-tolyl)-pyrimid-6-one, m.p. 243°–247° C., 4-amino-5-nitroso-2-(3-tolyl)pyrimid-6-one, m.p. 280°–281° C., crude 4-amino-5-nitroso-2-(4-tolyl)pyrimid-6-one, crude 4-amino-2-(2-chlorophenyl)-5-nitrosopyrimid-6-one, 4-amino-2-(4-chlorophenyl)-5-nitrosopyrimid-6-one, m.p. 269°–270° C. (with decomposition), 4-amino-2-(2-bromophenyl)-5-nitrosopyrimid-6-one, m.p. 165°–170° C., 4-amino-2-(2-fluorophenyl)-5-nitrosopyrimid-6-one, m.p. 257.5°–258.5° C., 4-amino-2-(4-hydroxyphenyl)-5-nitrosopyrimid-6-one, m.p. above 300° C., 4-amino-2-(2-ethoxyphenyl)-5-nitrosopyrimid-6-one, m.p. 221°–222° C., 4-amino-5-nitroso-2-(2-propoxyphenyl)pyrimid-6-one, m.p. 206°–207° C., 4-amino-2-(2-isopropoxyphenyl)-5-nitrosopyrimid-6-one, m.p. 208°–209° C. (with decomposition), crude 4-amino-2-(2-butoxyphenyl)-5-nitrosopyrimid-6-one, 4-amino-2-(2-isobutoxyphenyl)-5-nitrosopyrimid-6-one, m.p. 233°–235° C. (with decomposition), 4-amino-2-(2-sec-butoxyphenyl)-5-nitrosopyrimid-6-one, m.p. 186°–187° C., 4-amino-5-nitroso-2-(2-pentyloxyphenyl)pyrimid-6-one, m.p. 223°–224° C., 4-amino-2-(2-isopentyloxyphenyl)-5-nitrosopyrimid-6-one, m.p. 212°–214° C. (with decomposition), 4-amino-2-(2-hexyloxyphenyl)-5-nitrosopyrimid-6-one, m.p. 184°–185° C., 4-amino-2-(3-hexyloxyphenyl)-5-nitrosopyrimid-6-one, m.p. 225° C. (with decomposition), 4-amino-2-(4-hexyloxyphenyl)-5-nitrosopyrimid-6-one, m.p. 249°–250° C. (with decomposition), 4-amino-2-[2-(2-ethoxyethoxy)phenyl]-5-nitrosopyrimid-6-one, m.p. 194°–195° C., 4-amino-2-(2-methylmercaptophenyl)-5-nitrosopyrimid-6-one, m.p. 232.5°–233.5° C., 4-amino-2-(3-methylmercaptophenyl)-5-nitrosopyrimid-6-one, m.p. 238° C. (with decomposition), 4-amino-5-nitroso-2-(2-phenoxyphenyl)-pyrimid-6-one, m.p. 230° C. (with decomposition), crude 4-amino-2-[2-(4-methoxyphenoxy)-phenyl]-5-nitrosopyrimid-6-one, 4-amino-2-(2-benzyloxyphenyl)-5-nitrosopyrimid-6-one, 225°–226° C. (with decomposition), 4-amino-2-(2-methanesulphonylphenyl)-5-nitrosopyrimid-6-one, m.p. 264°–265° C. (with decomposition), 4-amino-2-(4-methanesulphonylphenyl)-5-nitrosopyrimid-6-one, m.p. 295°–296.5° C. (with decomposition), 4-amino-2-

(2-butanesulphonylphenyl)-5-nitrosopyrimid-6-one, m.p. 254° C. (with decomposition), 4-amino-5-nitroso-2-(3-trifluoromethylphenyl)pyrimid-6-one, m.p. 263° C. (with decomposition), 4-amino-2-(2-dimethylaminophenyl)-5-nitrosopyrimid-6-one, m.p. 212°–213° C. (with decomposition), 4-amino-2-(3-dimethylaminophenyl)-5-nitrosopyrimid-6-one, m.p. 215°–219° C., crude 4-amino-2-(2,3-dimethoxyphenyl)-5-nitrosopyrimid-6-one, 4-amino-2-(2,4-dimethoxyphenyl)-5-nitrosopyrimid-6-one, m.p. 225° C., 4-amino-2-(2,5-dimethoxyphenyl)-5-nitrosopyrimid-6-one, m.p. 250° C. (with decomposition), 4-amino-2-(2,6-dimethoxyphenyl)-5-nitrosopyrimid-6-one, m.p. 260° C. (with decomposition), 4-amino-2-(3,4-dimethoxyphenyl)-5-nitrosopyrimid-6-one, m.p. 278°–280° C. (with decomposition), crude 4-amino-2-(3,5-dimethoxyphenyl)-5-nitrosopyrimid-6-one, crude 4-amino-2-(4-benzyloxy-2-methoxyphenyl)-5-nitrosopyrimid-6-one, 4-amino-2-(5-benzyloxy-2-methoxyphenyl)-5-nitrosopyrimid-6-one, m.p. 228.5° C. (with decomposition), 4-amino-2-(2,5-dibenzyloxyphenyl)-5-nitrosopyrimid-6-one, m.p. 169°–170° C., crude 4-amino-2-(2-methoxy-5-trifluoromethylphenyl)-5-nitrosopyrimid-6-one, 4-amino-2-(2,3-methylenedioxyphenyl)-5-nitrosopyrimid-6-one, m.p. 210° C. (with decomposition), 4-amino-2-(1-naphthyl)-5-nitrosopyrimid-6-one, m.p. 256°–257° C., and 4-amino-2-(2-naphthyl)-5-nitrosopyrimid-6-one, m.p. 282° C. (with decomposition), respectively.

The 2-methoxybenzamidine hydrochloride used as starting material in the above preparation was prepared as follows:

To a solution of hydroxylamine hydrochloride (245 g.) and sodium carbonate (170 g.) in water (2.6 l.) was added a solution of 2-methoxybenzonitrile (127.5 g.) in ethanol (1.25 l.), and the mixture refluxed with stirring for 1.5 hours. The solution was concentrated in vacuo to low bulk and the resultant oil crystallised on standing. The solid was filtered off, washed with water to remove inorganic salts, dried at 60° C., and recrystallised from benzene to give 2-methoxybenzamidoxime (49.2 g.), m.p. 117°–119° C. Further material (21.2 g., m.p. 119°–120° C.) was obtained by concentration of the recrystallisation mother liquor.

A solution of 2-methoxybenzamidoxime (70.4 g.) in ethanol (500 ml.) was catalytically reduced at 70 p.s.i. pressure using Raney nickel catalyst (14 g). The solution was concentrated in vacuo to approximately 80 ml., diluted with dry diethyl ether (300 ml.), and a saturated solution of hydrogen chloride in diethyl ether (300 ml.) added with ice-cooling. The resultant precipitate was filtered off, washed well with dry diethyl ether, and dried in vacuo over silica gel to give 2-methoxybenzamidine hydrochloride (64.5 g.), m.p. 156°–159° C.

The 2-methoxybenzonitrile may be prepared as described by F. Ahrens, Ber., 1887, 20, 2955.

By proceeding in a similar manner, but substituting 2-propoxybenzamidoxime (prepared as described by A. A. Aroyan and S. P. Kocharyan, Izv. Akad. Nauk. Arm. S.S.R., Khim. Kauki, 1964, 17, 543), for the 2-methoxybenzamidoxime used as an intermediate in the above reaction, there was prepared 2-propoxybenzamidine hydrochloride, m.p. 169°–171° C.

By again proceeding in a similar manner, but substituting 3-methoxybenzonitrile (prepared as described by O. L. Mndzhoyan and G. M. Pogosyan, Izv.Akad.-Nauk.Arm.S.S.R., Khim.Hauki, 1963, 16, 263), 4-hexyloxybenzonitrile (prepared as described by M. W. Partridge, J.Chem.Soc., 1949, 3043), 2-(2-ethoxyethoxy)benzonitrile [prepared as described by Karl Thomae G.m.b.H. Chimisch pharmazeutische Fabrik, B.P. 774,635 (1957)], 2-methylmercaptobenzonitrile (prepared as described by T. Zincke & G. Siebert, Ber., 1915, 48, 1242), 2-methanesulphonylbenzonitrile, 2-butane-sulphonylbenzonitrile, 2-dimethylaminobenzonitrile (prepared as described by P. Grammaticakis, Bull.Soc.Chim France, 1953, 207), 2,5-dimethoxybenzonitrile (prepared as described by H. Kauffmann & A Grombach, Liebig's Annalen der Chemie, 1906, 344, 71) and 2-methoxy-5-trifluoromethylbenzonitrile for the 2-methoxybenzonitrile used as a starting material in the above preparation, there were prepared respectively: 3-methoxybenzamidoxime, m.p. 101°–103° C., 3-methoxybenzamidine, m.p. 161°–163° C., 4-hexyloxybenzamidoxime, m.p. 88°–90° C., 4-hexyloxybenzamidine hydrochloride (which contained 0.25 moles of water of crystallisation), m.p. 103°–104° C., crude 2-(2-ethoxyethoxy)benzamidoxime, 2-(2-ethoxyethoxy)benzamidine hydrochloride, m.p. 124°–125° C., 2-methylmercaptobenzamidoxime, m.p. 170°–172° C., 2-methylmercaptobenzamidine hydrochloride, m.p. 157°–161° C., 2-methanesulphonylbenzamidoxime, m.p. 225°–226° C., 2-methanesulphonylbenzamidine, m.p. 173° C. (with decomposition), 2-butanesulphonylbenzamidoxime, m.p. 134°–136° C., 2-butanesulphonylbenzamidine hydrochloride, m.p. 225° C., 2-dimethylaminobenzamidoxime, m.p. 134°–136° C., crude 2-dimethylaminobenzamidine, 2,5-dimethoxybenzamidoxime, m.p. 173° C., 2,5-dimethoxybenzamidine, m.p. 105° C., 2-methoxy-5-trifluoromethylbenzamidoxime, m.p. 119°–120° C. and crude 2-methoxy-5-trifluoromethylbenzamidine.

The 2-hexyloxybenzamidine hydrochloride used as a starting material in the above preparation was prepared as follows:

To a solution of 2-hexyloxybenzamide (64 g; prepared as described by E. M. Bavin, F. J. Macrae, D. E. Seymour and P. D. Waterhouse, J.Pharm.Pharmacol., 1952, 4, 872) in anhydrous methylene chloride (830 ml.) was added, dropwise during 10 minutes with stirring, a solution of triethyloxonium borofluoride (55.2 g.) in anhydrous methylene chloride (170 ml.). The solution was stirred for a further 105 minutes, and allowed to stand at room temperature for 2 days. The solution was concentrated to 350 ml., and anhydrous diethyl ether (1750 ml.) was added. The precipitated solid was filtered off and washed with anhydrous diethyl ether to give ethyl 2-hexyloxybenzimidate borofluoride (62 g.), m.p. 68°–70° C., which was pure enough to use for the next stage of the synthesis. A pure sample, m.p. 73°–74° C., was obtained by recrystallisation of an aliquot from a mixture of anhydrous methylene chloride and anhydrous diethyl ether.

A mixture of ethyl 2-hexyloxybenzimidate borofluoride (61 g.) and anhydrous ethanolic ammonia (90 ml.; prepared by saturation of anhydrous ethanol with anhydrous ammonia at 0° C.) was left to stand for 4 days. The solid which separated was filtered off and washed with anhydrous ethanol. The combined filtrate and washings were evaporated to dryness and the solid residue was treated with water (60 ml.) and 5N sodium hydroxide solution (120 ml.). The oil which separated was extracted with diethyl ether, the extracted dried over anhydrous potassium carbonate, and evaporated. The oily residue was dissolved in anhydrous diethyl ether (250 ml.) and an anhydrous ethanolic solution of hydrogen chloride (100 ml.; prepared by saturation at 0° C.) was added. The precipitated solid was filtered off, washed with anhydrous diethyl ether, and dried at 60° C. to give 2-hexyloxybenzamidine hydrochloride (44 g.), m.p. 155°–158° C. This compound may be further purified by recrystallisation from 2N hydrochloric acid.

By proceeding in a similar manner, but substituting 2-isopropoxybenzamide (prepared as described by E. M. Bavin, F. J. Macrae, D. E. Seymour and P. D. Waterhouse, J.Pharm.Pharmacol, 1952, 4, 872), 2-isobutoxybenzamide, 2-sec-butoxybenzamide (prepared as described by L. V. Coates, D. J. Drain, J. A. Kerridge, F. J. Macrae and K. Tattersall, J.Pharm.Pharmacol, 1957, 9, 855), 2-isopentyloxybenzamide (prepared as described by J. A. Faust, L. H. Jules and M. Sahyun, J.Amer.Pharm.Assoc., 1956, 45, 514), 3-hexyloxybenzamide (prepared as described by L. V. Coates, D. J. Drain, F. J. Macrae and K. Tattersall, J.Pharm.Pharmacol, 1959, 11, Suppl. 240T), 2-bromobenzamide (prepared as described by C. Schotten, Ber., 1888, 21, 2235), 2-fluorobenzamide prepared as described by H. Meyer & A. Hub, Monatsh., 1910, 31, 936), 2-benzyloxybenzamide (prepared as described by J. A. Faust, L. H. Jules and M. Sahyun, J.Amer.Pharm.Assoc., 1956, 45, 514) and 2,5-dibenzyloxybenzamide for the 2-hexyloxybenzamide used as a starting material in the above preparation, there were prepared respectively: ethyl 2-isopropoxybenzimidate borofluoride, m.p. 130°–132° C., crude 2-isopropoxybenzamidine (characterised as its picrate, m.p. 188°–189° C.), ethyl 2-isobutoxybenzimidate borofluoride, m.p. 108°–111° C., crude 2-isobutoxybenzamidine (characterised as its picrate, m.p. 187°–188° C.), ethyl 2-sec-butoxybenzimidate borofluoride, m.p. 73°–74° C., crude 2-secbutoxybenzamidine (characterised as its picrate, m.p. 159°–161° C.), ethyl 2-isopentyloxybenzimidate borofluoride, m.p. 120.5°–123° C., 2-isopentyloxybenzamidine hydrochloride, m.p. 156°–157° C., crude ethyl 3-hexyloxybenzimidate borofluoride, crude 3-hexyloxybenzamidine, crude ethyl 2-bromobenzimidate borofluoride, 2-bromobenzamidine hydrochloride, m.p. 303°–305° C., crude ethyl 2-fluorobenzimidate borofluoride, 2-fluorobenzamidine hydrochloride, m.p. 168°–171° C., ethyl 2-benzyloxybenzimidate borofluoride, m.p. 117°–118° C., crude 2-benzyloxybenzamidine (characterised in the form of the picrate, m.p. 184°–185° C.), crude ethyl 2,5-dibenzyloxybenzimidate borofluoride and 2,5-dibenzyloxybenzamidine, m.p. 102°–108° C.

The 2-isobutoxybenzamide used as a starting material in the above preparation was prepared as follows:

Salicylamide (68.5 g.; prepared as described by R. Bogoczek, Farm. Polska, 1960, 16, 26) was added to a solution of sodium (11.5 g.) in anhydrous ethanol (400 ml.). Isobutyl bromide (60 ml.) was then added, and the mixture was stirred and heated to reflux overnight. The ethanol was evaporated, and sufficient water was added to the residue to dissolve the sodium bromide. The oil which did not dissolve was extracted with chloroform, the extract was washed twice with 2N sodium hydroxide solution and once with water, dried over magnesium sulphate, filtered and evaporated. The residue was triturated with light petroleum (b.p. 40°–60° C.) to give 2-isobutoxybenzamide, which was pure enough for use in the next stage of the synthesis. A pure sample, m.p. 125°–128° C., was obtained by recrystallisation of an aliquot from cyclohexane.

The 2,6-dimethoxybenzamidine used as a starting material in the above preparation was prepared as follows:

A mixture of 2,6-dimethoxybenzamide (68 g.; prepared as described by P. Grammaticakis, Compt. rend., 1968, 267C,152), methyl fluorosulphonate (45 g.) and anhydrous methylene dichloride (1 l.) was stirred at room temperature for 3 hours. The solution was evaporated in vacuo, and the residue treated with anhydrous diethyl ether to give crude methyl 2,6-dimethoxybenzimidate fluorosulphonate as a white solid, m.p. 115°–137° C. This was dissolved in anhydrous ethanol (1 l.) and the solution was cooled to 0° C. Anhydrous ethanolic ammonia (350 ml.; prepared by saturation of anhydrous ethanol with anhydrous ammonia at 0° C.) was added, and the mixture kept at room temperature for 4 days. The solution was filtered, the filtrate was evaporated in vacuo, the residue was treated with an excess of 2N sodium hydroxide solution, and the precipitated solid was filtered off, washed with water and recrystallised from isopropanol to give 2,6-dimethoxybenzamidine (15 g.), m.p. 170°–174° C.

By proceeding in a similar manner but substituting: 2-butoxybenzamide (prepared as described by E. M. Bavin, F. J. Macrae, D. E. Seymour and P. D. Waterhouse, J.Pharm.Pharmacol, 1952, 4, 872), 2-pentyloxybenzamide (prepared as described by E. M. Bavin, F. J. Macrae, D. E. Seymour and P. D. Waterhouse, J.Pharm.Pharmacol, 1952, 4, 872), 2-phenoxybenzamide (prepared as described by G. Lock and F. H. Kempter, Monatsh., 1935, 67, 24), 2-(4-methoxyphenoxy)benzamide, 2,3-dimethoxybenzamide (prepared as described by F. Mauthner, J.Prakt.Chem., 1926, [2], 112, 64), 2,4-dimethoxybenzamide (prepared as described by P. Grammaticakis, Bull.Soc.Chim. France, 1965, 848), 3,5-dimethoxybenzamide (prepared as described by F. Mauthner, J.Prakt.Chem., 1913, [2], 87, 405), 4-benzyloxy-2-methoxybenzamide, 5-benzyloxy-2-methoxybenzamide and 2,3-methylenedioxybenzamide for the 2,6-dimethoxybenzamide used as a starting material in the above preparation, there were prepared: crude 2-butoxybenzamidine fluorosulphonate, crude 2-pentyloxybenzamidine, crude 2-phenoxybenzamidine, crude 2-(4-methoxyphenoxy)benzamidine, 2,3-dimethoxybenzamidine fluorosulphonate, m.p. 75°–80° C., 2,4-dimethoxybenzamidine fluorosulphonate, m.p. 193° C., 3,5-dimethoxybenzamidine fluorosulphonate, m.p. 115°–125° C., crude 4-benzyloxy-2-methoxybenzamidine, crude 5-benzyloxy-2-methoxybenzamidine and crude 2,3-methylenedioxybenzamidine respectively.

The 3-methylmercaptobenzamidine hydrochloride used as a starting material in the above preparation was prepared as follows:

A solution of 3-methylmercaptobenzonitrile (26.2 g.; prepared as described by T. Zincke and J. Muller, Ber., 1913, 46, 775) and anhydrous ethanol (28.4 ml.) in anhydrous chloroform (47.3 ml.) was cooled to 0° C., saturated with anhydrous hydrogen chloride, and the mixture kept at 0° C. for 5 days. The solution was evaporated in vacuo, the residue mixed with anhydrous 10% ethanolic ammonia (200 ml.) and kept at 37° C. for 5 days. The solid was filtered off, combined with that obtained by evaporation of the filtrate and suspended in water (300 ml.), brought to pH 11 with concentrated sodium hydroxide solution, and extracted with chloroform. The chloroform extract was washed with water, dried over sodium sulphate, and evaporated. The residue was dissolved in anhydrous ethanol and saturated ethanolic hydrogen chloride was added, followed by an excess of anhydrous diethyl ether. The solid which separated was filtered off. This 3-methylmercaptobenzamidine hydrochloride (23 g.) was pure enough to use in the next stage of the synthesis. An aliquot was purified by dissolving in anhydrous ethanol, boiling with charcoal, filtering and precipitating with ether, to give pure 3-methylmercaptobenzamidine hydrochloride, m.p. 157°–161° C.

By proceeding in a similar manner but substituting 3-dimethylaminobenzonitrile (prepared as described by P. Grammaticakis, Bull.Soc.Chim. France, 1953, 207) and 3-trifluoromethylbenzonitrile (prepared as described by F. Swarts, Chem. Zent., 1898, II, 26) for the 3-methylmercaptobenzonitrile used as a starting material in the above preparation, there were prepared 3-dimethylaminobenzamidine hydrochloride, m.p. 195°–198° C. and crude 3-trifluoromethylbenzamidine, respectively.

The 2-methanesulphonylbenzonitrile used as a starting material in the above preparation was prepared as follows:

2-Methanesulphonylbenzamide (34 g.) was added to phosphorus oxychloride (100 ml.) and the mixture was refluxed for 90 minutes. The excess of phosphorus oxychloride was evaporated in vacuo, and the oily residue was treated with water (200 ml.), with ice cooling. The solid which separated was filtered off, washed with water and recrystallised from ethanol to give 2-methanesulphonylbenzonitrile (27 g.), m.p. 105°–106° C.

2-Butanesulphonylbenzonitrile, b.p. 225°–227° C./10 mm.Hg, was prepared similarly, from 2-butanesulphonylbenzamide.

The 2-methanesulphonylbenzamide, used as a starting material in the above preparation, was prepared as follows:

2-Methanesulphonylbenzoic acid (64 g.; prepared as described by P. Oxley, M. W. Partridge, T. D. Robson and W. F. Short, J.Chem.Soc., 1946, 763) and thionyl chloride (200 ml.) were refluxed together for 3 hours. The excess of thionyl chloride was evaporated in vacuo, and the residue was added slowly, in portions, to concentrated aqueous ammonia solution (400 ml.) with shaking and cooling. After standing at 0° C., the solid was filtered off and recrystallised from ethanol to give 2-methanesulphonylbenzamide (36 g.), m.p. 149° C.

Prepared by proceeding in a similar manner were 2-butanesulphonylbenzamide, m.p. 102°–103° C., 4-benzyloxy-2-methoxybenzamide, m.p. 120°–122° C., 5-benzyloxy-2-methoxybenzamide, m.p. 144°–146° C., 2,5-dibenzyloxybenzamide, m.p. 153°–155° C., 2-(4-methoxyphenoxy)benzamide, m.p. 154°–155° C., and 2,3-methylenedioxybenzamide, m.p. 174°–176° C., from 2-butanesulphonylbenzoic acid, 4-benzyloxy-2-methoxybenzoic acid (prepared as described by K. G. Dave, S. A. Telang and K. Vonkataraman, J.Sci.Ind.Res. (India), 1960, 19B, 470), 5-benzyloxy-2-methoxybenzoic acid, 2,5-dibenzyloxybenzoyl chloride (prepared as described by A. Zane and S. H. Wender, J.Org.Chem., 1964, 29, 2078), 2-(4-methoxyphenoxy)benzoic acid (prepared as described by F. Ullmann and M. Zlokasoff, Ber., 1905, 38, 2117) and 2,3-methylenedioxybenzoic acid (prepared as described by W. H. Perkin and V. M. Trikojus, J.Chem.Soc., 1926, 2925), respectively.

The 2-butanesulphonylbenzoic acid, used as a starting material in the above preparation, was prepared as follows:

A solution of 2-butylmercaptobenzoic acid (10.5 g.; prepared as described by S. E. Livingstone, J.Chem.Soc., 1956, 437) in glacial acetic acid (100 ml.) was heated at 100° C. for 1 hour with hydrogen peroxide (100 vols.; 50 ml.). The solution was evaporated in vacuo almost to dryness, and water was added to the residue. The mixture was extracted with dichloromethane, the extract was dried over anhydrous sodium sulphate and filtered, and the filtrate was evaporated. The residue was treated with light petroleum (b.p. 40°–60° C.) and cooled to about −70° C. The solid was filtered off and recrystallised from toluene, cooling to about −70° C. and filtering cold, to give 2-butanesulphonylbenzoic acid (11.0 g.), m.p. 72.5°–73.5° C.

The 5-benzyloxy-2-methoxybenzoic acid, used as a starting material in the above preparation, was prepared as follows:

Anhydrous potassium carbonate (60 g.) was added slowly with stirring to a refluxing mixture of 5-benzyloxysalicylic acid (13 g.; prepared as described by H. Bogeny and R. Krattner, Arch.Pharm; 1960, 293, 393) and anhydrous ethanol (250 ml.). Dimethyl sulphate (36 ml.) was then added, and the mixture stirred under reflux for 24 hours. The solid was filtered off, and the filtrate evaporated in vacuo to give more solid. The combined solids were suspended in water (250 ml.), and sodium hydroxide (20 g.) was added. The mixture was stirred under reflux for 2 hours, and then concentrated hydrochloric acid was added through the condenser, at such a rate that the contents of the flask continued to reflux gently, until pH 1 was attained. After being cooled, the solid which separated was filtered off, and recrystallised from 50% aqueous ethanol, and then from ethanol, to give 5-benzyloxy-2-methoxybenzoic acid (8 g.), m.p. 114°–116° C.

The 2-methoxy-5-trifluoromethylbenzonitrile used as a starting material in the above preparation was prepared as follows:

2-Bromo-5-trifluoromethylbenzonitrile (2.5 g.; prepared as described by M. Gordon, I. J. Pachter and J. W. Wilson, Arzneimittel-Forsch., 1963, 13, 802) and a solution of sodium methoxide (prepared from 0.5 g. sodium and 20 ml. anhydrous methanol) were stirred and refluxed together for 4 hours, and allowed to stand at room temperature overnight. The methanol was evaporated and the residue was acidified with 2N hydrochloric acid, with cooling. The mixture was extracted with diethyl ether, and the extract was dried over anhydrous sodium sulphate, filtered and the filtrate was evaporated, and the residue was recrystallised from pentane to give 2-methoxy-5-trifluoromethylbenzonitrile (1.0g.), m.p. 31°–33° C.

EXAMPLE 2

8-Aza-2-phenylpurin-6-one (3 g, prepared as described in Example 1) was added in portions to a stirred mixture of concentrated nitric acid (density 1.42, 5 ml) and concentrated sulphuric acid (6 ml), maintaining the temperature at 20°–30° C. Stirring was continued for a further 1 hour. The mixture was left to stand overnight and then poured into ice-water (50 ml.). The precipitated solid was filtered off and recrystallised from aqueous dimethylformamide to give 8-aza-2-(3- nitrophenyl)purin-6-one monohydrate (0.8 g.), in the form of a pale yellow solid, m.p. 160°–165° C.

By proceeding in a similar manner, but substituting 8-aza-2-(2-methoxyphenyl)purin-6-one (prepared as described in Example 1) and 8-aza-2-(2-hydroxyphenyl)purin-6-one (prepared as described in Example 3) for the 8-aza-2-phenylpurin-6-one used as a starting material in the above preparation, there were prepared 8-aza-2-(2-methoxy-5-nitrophenyl)purin-6-one, m.p. 260°–261° C. (with decomposition) and 8-aza-2-(2-hydroxy-3,5-dinitrophenyl)purin-6-one, characterised in the form of its ammonium salt which decomposed without melting at 315° C.

EXAMPLE 3

A solution of 8-aza-2-(2-benzyloxyphenyl)purin-6-one (1.0 g; prepared as described in Example 1) in methanol (100 ml.) containing 5% palladium-charcoal (0.2 g.) was hydrogenated at atmospheric pressure and room temperature. The theoretical volume (71 ml.) of hydrogen was taken up during 75 minutes. The solid was filtered off and the filtrate was evaporated to give crude product (0.25 g.). The catalyst which was filtered off was extracted with 2N sodium hydroxide solution and the extract was filtered and acidified with 2N hydrochloric acid to give a further quantity (0.4 g.) of crude product. The combined crude products were recrystallised from aqueous ethanol to give 8-aza-2-(2-hydroxyphenyl)purin-6-one (0.4 g.), m.p. 283°–284° C. (with decomposition).

By proceeding in a similar manner but substituting 8-aza-2-(5-benzyloxy-2-methoxyphenyl)purin-6-one and 8-aza-2-(2,5-dibenzyloxyphenyl)purin-6-one for the 8-aza-2-(2-benzyloxyphenyl)purin-6-one used as a starting material in the above preparation, there were prepared 8-aza-2-(5-hydroxy-2-methoxyphenyl)purin-6-one, m.p. 288.5°–290° C. (with decomposition) and 8-aza-2-[2(or 5)-benzyloxy-5(or 2)-hydroxyphenyl]-purin-6-one, m.p. 268°–272° C. (with decomposition), respectively.

EXAMPLE 4

8-Aza-2-(2-methoxyphenyl)purin-6-one (200 mg; prepared as described in Example 1) was dissolved in a 2N aqueous solution of sodium hydroxide (4 ml.), and the stirred solution treated dropwise with glacial acetic acid. While the pH was still above 11, a cream-coloured solid was precipitated. This was filtered off, recrystallised from a mixture of ethanol and diethyl ether, and left to dry in air overnight to give the sodium salt of 8-aza-2-(2-methoxyphenyl)purin-6-one as a crystalline hydrate (100 mg.), each mole of the salt being associated with 2.4 moles of water, melting with decomposition over the range 50°–250° C.

EXAMPLE 5

A solution of 85% potassium hydroxide pellets (0.33 g.) in dry methanol (13 ml.) was added to a hot solution of choline chloride (0.7 g.) in isopropanol (36 ml.). The mixture was cooled to 0° C, and the potassium chloride filtered off and rinsed with isopropanol (2 × 3 ml). 8-Aza-2-(2-methoxyphenyl)purin-6-one (1.13 g; prepared as described in Example 1) was added to the combined filtrate and washings and the mixture warmed for 4 minutes on the steam-bath. The warm mixture was filtered and diluted with dry diethyl ether (100 ml.). The gum which separated out crystallised on standing at 0° C. overnight, and the crystals so formed were filtered off, rinsed with dry diethyl ether, recrystallised from a mixture of dry ethanol and diethyl ether, and dried to give the choline salt of 8-aza-2-(2-methoxyphenyl)purin-6-one in the form of its hemihydrate (1.2 g.), m.p. 158°–160° C.

EXAMPLE 6

8-Aza-2-(2-methoxyphenyl)purin-6-one (2.4 g.) was refluxed for 5 minutes with a solution of sodium (0.23 g.) in anhydrous ethanol (25 ml.), and cooled. Anhydrous diethyl ether (75 ml.) was added, and the solid was filtered off, and recrystallised from a mixture of anhydrous ethanol and anhydrous diethyl ether to give the sodium salt of 8-aza-2-(2-methoxyphenyl)purin-6-one hemihydrate (0.75 g.), m.p. ca 310° C. (with decomposition).

EXAMPLE 7

A mixture of 8-aza-2-(2-methoxyphenyl)purin-6-one (237 g.), triethanolamine (400 ml.) and anhydrous ethanol (3 liters) was refluxed for 1 hour. The solution was filtered and left to stand at 0° C. for 2 hours. The solid which separated was filtered off and recrystallised from anhydrous ethanol to give the triethanolamine salt of 8-aza-2-(2-methoxyphenyl)purin-6-one, m.p. 138°–139° C., (216 g.).

By proceeding in a similar manner, but substituting diethylamine and triethylamine for the triethanolamine used as a starting material in the above preparation, there were prepared the diethylamine salt of 8-aza-2-(2-methoxyphenyl)purin-6-one (which contained 0.4 moles of water of crystallisation), m.p. 138°–142° C, and the triethylamine salt of 8-aza-2-(2-methoxyphenyl)purin-6-one, m.p. 184°–197° C, respectively.

EXAMPLE 8

A mixture of 8-aza-2-(2-methoxyphenyl)purin-6-one (4.0 g.), diethanolamine (4 ml.) and anhydrous ethanol (40 ml.) was refluxed for 5 minutes, concentrated to half its volume and diluted with anhydrous diethyl ether (60 ml.). The solid which separated was recrystallised from anhydrous ethanol (55 ml.) to give the diethanolamine salt of 8-aza-2-(2-methoxyphenyl)purin-6-one, m.p. 142°–143° C, (3.4 g.).

By proceeding in a similar manner, but substituting ethylenediamine and octadecylamine for the diethanolamine used as a starting material in the above preparation, there were prepared the ethylenediamine salt of 8-aza-2-(2-methoxyphenyl)purin-6-one (which contained 0.25 moles of water of crystallisation), m.p. 208°–209° C. (with decomposition), and the octadecylamine salt of 8-aza-2-(2-methoxyphenyl)purin-6-one, m.p. 97°–98° C, respectively.

EXAMPLE 9

1-(3,4-isopropylaminoethanol 2-isopropylaminoethanol sulphate (1.15 g.) was refluxed for 5 minutes with a solution of sodium (0.1 g.) in anhydrous ethanol (10 ml.). The sodium sulphate was filtered off, and 8-aza-2-(2-methoxyphenyl)purin-6-one (1.0 g.) was added to the filtrate, and the mixture was refluxed for 5 minutes. The mixture was filtered, and the filtrate was diluted with anhydrous diethyl ether, and the solid which separated was filtered off and recrystallised from isopropanol to give the 1-(3,4-dihydroxyphenyl)-2-isopropylaminoethanol salt of 8-aza-2-(2-methoxyphenyl)purin-6-one (which contained 0.33 moles of water of crystallisation), m.p. 155° C. (with decomposition) after softening at ca 105° C. (0.35 g.).

EXAMPLE 10

Toluene-p-sulphonic acid monohydrate (1.04 g.) was heated in refluxing xylene (80 ml.) for 3.5 hours, using a Dean and Stark apparatus, in order to remove water. 5-Amino-4-carbamoyl-1H-1,2,3-triazole (1.52 g.) was then added, followed by triethyl trithioorthobenzoate (3 ml.). Refluxing was continued for a further 5.5 hours. The cooled reaction mixture was extracted with 2N aqueous sodium hydroxide solution, and the aqueous layer separated and acidified with aqueous hydrochloric acid. A dark brown solid (0.9 g.) separated, which was filtered off and extracted with boiling isopropanol. Upon cooling the isopropanol extract, light brown crystals were obtained, which upon a further recrystallisation from isopropanol with the use of adsorbent charcoal, gave 8-aza-2-phenylpurin-6-one (0.12 g.) as buff-coloured crystals, m.p. 278° C. (with decomposition).

The 5-amino-4-carbamoyl-1H-1,2,3-triazole, used as a starting material in the above preparation, may be prepared according to the method described by J. R. E. Hoover and A. R. Day, J. Amer. Chem. Soc., 1956, 78, 5832.

Triethyl trithioorthobenzoate may be prepared according to the method described by L. C. Rinzema, J. Stoffelsma, and J. F. Arens, Rec. Trav. Chim., 1959, 78, 354.

EXAMPLE 11

5-Amino-4-carbamoyl-1H-1,2,3-triazole (0.7 g.), triethyl trithioorthobenzoate (1.5 ml.) and boron trifluoride etherate (0.38 ml.) were heated together overnight in refluxing anhydrous xylene (25 ml.). The cooled reaction mixture was extracted with 2N aqueous sodium hydroxide solution. The aqueous layer was separated, treated with adsorbent charcoal, and warmed. The charcoal was then filtered off, and the filtrate acidified with aqueous hydrochloric acid, whereupon 8-aza-2-phenylpurin-6-one (0.2 g.), m.p. 273° C. (with decomposition), was precipitated.

EXAMPLE 12

5-Amino-4-carbamoyl-1H-1,2,3-triazole (0.8 g.), benzamidine hydrochloride (1.0 g.) and anhydrous sodium acetate (1.2 g.) were heated together at 190° C. for 24 hours. The cooled reaction mixture was treated with 2N aqueous lithium hydroxide solution (20 ml.), and the undissolved solid was filtered off. The filtrate was adjusted to pH4 with concentrated hydrochloric acid, and was then left to stand at 0° C. for 2 hours. The precipitated solid (0.46 g.) was filtered off, washed with water, and recrystallised from ethanol to give 8-aza-2-phenylpurin-6-one (0.17 g.), m.p. 283° C. (with decomposition).

EXAMPLE 13

Sodium nitrite (3 g.) was added slowly with stirring to a solution of concentrated hydrochloric acid (100 ml.) in water (100 ml.) maintained at between −5° and 0° C. by means of an ice/salt bath. 2-(2-Allyloxyphenyl)-4,5-diaminopyrimid-6-one (5.1 g.) was then added in portions during 30 minutes with stirring at between −5° and 0° C. The cooling bath was removed, and the mixture stirred at room temperature overnight. The solid which separated was filtered off and dissolved in a solution of concentrated ammonium hydroxide (10 ml.) in water (100 ml.). The solution was heated with charcoal, filtered, and the filtrate acidified with glacial acetic acid. The solid which separated was filtered off and recrystallised from methanol to give 2-(2-allyloxyphenyl)-8-azapurin-6-one (1.7 g.), m.p. 173°–175° C.

By proceeding in a similar manner, but substituting 4,5-diamino-2-(2-methoxy-3-methylphenyl)pyrimid-6-one, crude 4,5-diamino-2-(2-methoxy-5-methylphenyl)pyrimid-6-one, 4,5-diamino-2-(2-methoxy-3,5-dimethylphenyl)pyrimid-6-one, crude 4,5-diamino-2-(5-tert-butyl-2-methoxyphenyl)pyrimid-6-one -methylphenyl)purin--dimethylphenyl)purin--benzylphenyl) and 4,5-diamino-2-(4-benzylphenyl)-pyrimid-6-one for the 2-(2-allyloxyphenyl)-4,5-diaminopyrimid-6-one used as a starting material in the above preparation, there were prepared 8-aza-2-(2-methoxy-3-methylphenyl)purin-6-one, m.p. 248°–249° C. (with decomposition), 8-aza-2-(2-methoxy-5-methylphenyl)purin6-one, m.p. 230°–232° C. (with decomposition), 8-aza-2-(2-methoxy-3,5-dimethylphenyl)purin-6-one, m.p. 223°–224° C. (with decomposition), 8-aza-2-(5-tert-butyl-2-methoxyphenyl)purin-6-one, m.p. 260°–262° C. (with decomposition) and 8-aza-2-(4-benzylphenyl)purin-6-one, m.p. 272°–274° C. (with decomposition), respectively.

The 2-(2-allyloxyphenyl)-4,5-diaminopyrimid-6-one, used as a starting material in the above preparation, was prepared as follows:

2-(2-Allyloxyphenyl)-4-amino-5-nitrosopyrimid-6-one (6.3 g.) was suspended in a solution of triethylamine (15 ml.) in water (250 ml.). Sodium dithionite (12 g.) was added in portions with stirring at room temperature. The temperature of the mixture was then raised to 60° C., and it was stirred at this temperature for a further 20 minutes. The pH of the mixture was adjusted to 7 by the addition of glacial acetic acid, and the mixture cooled in ice/water. The solid was filtered off and washed with water to give 2-(2-allyloxyphenyl)-4,5-diaminopyrimid-6-one (5.1 g.), m.p. 127°–130° C.

By proceeding in a similar manner, but substituting 4-amino-2-(2-methoxy-3-methylphenyl)-5-nitrosopyrimid-6-one, 4-amino-2-(2-methoxy-5-methylphenyl)-5-nitrosopyrimid-6-one, 4-amino-2-(2-methoxy-3,5-dimethylphenyl)-5-nitrosopyrimid-6-one, 4-amino-2-(5-tert-butyl-2-methoxyphenyl)-5-nitrosopyrimid-6-one and 4-amino-2-(4-benzylphenyl)-5-nitrosopyrimid-6-one for the 2-(2-allyloxyphenyl)-4-amino-5-nitrosopyrimid-6-one used as a starting material in the above preparation, there were prepared 4,5-diamino-2-(2-methoxy-3-methylphenyl)-pyrimid-6-one, m.p. 248°–249° C. (with decomposition), crude 4,5-diamino-2-(2-methoxy-5-methylphenyl)pyrimid-6-one [characterised as its hydrochloride, m.p. 260°–262° C. (with decomposition), which contained 0.1 moles of water of crystallisation per mole], 4,5-diamino-2-(2-methoxy-3,5-dimethylphenyl)pyrimid-6-one, m.p. 163°–170° C., crude 4,5-diamino-2-(5-tert-butyl-2-methoxyphenyl)pyrimid-6-one, m.p. 85°–91° C., and 4,5-diamino-2-(4-benzylphenyl)pyrimid-6-one, m.p. 205°–208° C., respectively.

The 2-(2-allyloxyphenyl)-4-amino-5-nitrosopyrimid-6-one, used as a starting material in the above preparation, was prepared as follows:

2-Allyloxybenzamidine hydrochloride (10.2 g.) was added to a solution of sodium (4.6 g.) in anhydrous methanol (200 ml.) with stirring, followed by ethyl α-oximinocyanoacetate (7.6 g.), and the mixture was stirred under reflux for 6 hours. The hot mixture was poured into water (500 ml.) and acidified with glacial acetic acid. The blue solid was filtered off, washed with water and recrystallised from 50% aqueous acetic acid to give 2-(2-allyloxyphenyl)-4-amino-5-nitrosopyrimid-6-one (7.3 g.), m.p. 217°–220° C.

By proceeding in a similar manner, but substituting 2-methoxy-3-methylbenzamidine hydrochloride, 2-methoxy-5-methylbenzamidine hydrochloride, crude 2-methoxy-3,5-dimethylbenzamidine, 5-tert-butyl-2-methoxybenzamidine hydrochloride and 4-benzylbenzamidine hydrochloride for the 2-allyloxybenzamidine hydrochloride used as starting material in the above preparation, there were prepared 4-amino-2-(2-methoxy-3-methylphenyl)-5-nitrosopyrimid-6-one, m.p. 206° C. (with decomposition), 4-amino-2-(2-methoxy-5-methylphenyl)-5-nitrosopyrimid-6-one, m.p. 224° C. (with decomposition), 4-amino-2-(2-methoxy-3,5-dimethylphenyl)-5-nitrosopyrimid-6-one, m.p. 212° C. (with decomposition), 4-amino-2-(5-tert-butyl-2-methoxyphenyl)-5-nitrosopyrimid-6-one, m.p. 215°–218° C. (with decomposition), and 4-amino-2-(4-benzylphenyl)-5-nitrosopyrimid-6-one, m.p. 237°–239° C. (with decomposition), respectively.

The 2-allyloxybenzamidine hydrochloride, used as a starting material in the above preparation, was prepared as follows:

2-Allyloxybenzamide (20 g; prepared as described by J. A. Faust, L. H. Jules and M. Sahyun, J. Amer. Pharm. Assoc., 1956, 45, 514) was dissolved in anhydrous methylene chloride (250 ml.). Methyl fluorosulphonate (16 g.) was added and the mixture was stirred at room temperature for 2 hours, and then left to stand overnight. The solvent was evaporated in vacuo and the residue was mixed with ethanolic ammonia solution (200 ml; prepared by saturation of anhydrous ethanol with ammonia gas at 0° C.) and the mixture was stirred for 1 day and left to stand at room temperature for a further 1 day. The mixture was evaporated to dryness, and the residue was mixed with chloroform (300 ml.) and water (200 ml.). The mixture was cooled to about 8° C. and stirred vigorously while 50% aqueous sodium hydroxide solution was added dropwise until pH 11 was attained. The chloroform layer was separated, washed once with ice-cold water, and dried over sodium sulphate. The dried chloroform solution was evaporated in vacuo, and the residue was dissolved in anhydrous diethyl ether, and the solution treated with an excess of an anhydrous solution of hydrogen chloride in diethyl ether. The solid which separated was filtered off to give 2-allyloxybenzamidine hydrochloride (19.08 g.), m.p. 166°–175° C.

The 2-methoxy-3-methylbenzamidine hydrochloride, used as a starting material in the above preparation, was prepared as follows:

A solution of triethyloxonium borofluoride (23 g.) in anhydrous methylene chloride (60 ml.) was added to a solution of 2-methoxy-3-methylbenzamide [19.7 g; prepared as described in French Patent M.21] in anhydrous methylene chloride (200 ml.). The mixture was kept at room temperature for 3 days, concentrated to about 120 ml. and diluted with anhydrous diethyl ether (300 ml.). The solid which separated was filtered off and washed with anhydrous diethyl ether to give ethyl 2-methoxy-3-methylbenzimidate borofluoride (28.7 g.), m.p. 93°–96° C., which was pure enough for use in the next stage of the synthesis. An aliquot was recrystallised from a mixture of anhydrous methylene chloride and anhydrous diethyl ether to give pure ethyl 2-methoxy-3-methylbenzimidate borofluoride, m.p. 102°–104° C.

Ethyl 2-methoxy-3-methylbenzimidate borofluoride (28 g.) was mixed with a saturated anhydrous solution of ammonia in ethanol (46 ml.), the mixture was kept at room temperature in a stoppered vessel for 3 days and then evaporated to dryness in vacuo. The residue was dissolved in water (25 ml.) and treated with 5N sodium hydroxide solution (50 ml.). The solution was saturated with sodium chloride and extracted with diethyl ether. The extract was dried over potassium hydroxide and evaporated to give crude 2-methoxy-3-methylbenzamidine, m.p. 72°–74° C. This was dissolved in anhydrous ethanol (40 ml.) and the solution treated with a saturated anhydrous solution of hydrogen chloride in diethyl ether (100 ml.), and diluted with anhydrous diethyl ether (100 ml.). The solid which separated was filtered off and washed with anhydrous diethyl ether to give 2-methoxy-3-methylbenzamidine hydrochloride (17.8 g.), m.p. 208°–209° C. (with decomposition).

By proceeding in a similar manner, but substituting 2-methoxy-5-methylbenzamide (prepared as described by L. Gattermann, Liebig's Annalen der Chemie, 1888, 244, 66) and 2-methoxy-3,5-dimethylbenzamide for the 2-methoxy-3-methylbenzamide used as a starting material in the above preparation, there were prepared ethyl 2-methoxy-5-methylbenzimidate borofluoride, m.p. 202°–204° C. (with decomposition), 2-methoxy-5-methylbenzamidine hydrochloride, m.p. 226°–227° C. (with decomposition), crude ethyl 2-methoxy-3,5-dimethylbenzimidate borofluoride and crude 2-methoxy-3,5-dimethylbenzamidine.

The 2-methoxy-3,5-dimethylbenzamide, used as a starting material in the above preparation, was prepared as follows:

2-Methoxy-3,5-dimethylbenzoic acid (52.7 g.) and thionyl chloride (200 ml.) were refluxed together for 1 hour. The excess of thionyl chloride was evaporated in vacuo and the residue dissolved in anhydrous diethyl ether (100 ml.) The solution was added dropwise to stirred, ice-cooled, concentrated aqueous ammonia solution (350 ml.) during 50 minutes, and the mixture was stirred for a further 3 hours and left at room temperature overnight. The solid obtained was filtered off, washed with diethyl ether and recrystallised from ethanol (with the use of charcoal) to give 2-methoxy-3,5-dimethylbenzamide (27.8 g.), m.p. 109°–113° C., which was pure enough for use in the next stage of the synthesis. An aliquot was further recrystallised from ethanol to give 2-methoxy-3,5-dimethylbenzamide, m.p. 114°–116° C.

The 2-methoxy-3,5-dimethylbenzoic acid, used as a starting material in the above preparation, was prepared as follows:

The disodium salt of 2-hydroxy-3,5-dimethylbenzoic acid (21 g.) and dimethyl sulphate (92 ml.) were stirred together at 140°–150° C. for 2.5 hours. After standing overnight, the mixture was added to a solution of sodium hydroxide (40 g.) in water (250 ml.), and the mixture stirred and heated on the steam-bath for 1 hour. Charcoal was added, the mixture was filtered and the filtrate was cooled, acidified with concentrated hydrochloric acid, and maintained at 0° C. The solid which separated was filtered off and recrystallised from aqueous ethanol to give 2-methoxy-3,5-dimethylbenzoic acid (14.7 g.), m.p. 97°–98° C.

The disodium salt of 2-hydroxy-3,5-dimethylbenzoic acid, used as a starting material in the above preparation, was prepared as follows:

2-Hydroxy-3,5-dimethylbenzoic acid (20 g; prepared as described by W. R. Nummy and D. S. Tarbell, J. Amer. Chem. Soc., 1951, 73, 1500) was added to a solution of sodium (5.5 g.) in anhydrous methanol (200 ml.). Anhydrous toluene (200 ml.) was added and most of the excess of methanol was distilled off. The solid which separated was filtered off and washed with anhydrous diethyl ether to give the disodium salt of 2-hydroxy-3,5-dimethylbenzoic acid (22.8 g.).

The 5-tert-butyl-2-methoxybenzamidine hydrochloride, used as a starting material in the above preparation, was prepared as follows:

5-tert-Butyl-2-methoxybenzamidoxime (22.2 g.) was dissolved in ethanol (250 ml.) and hydrogenated at 5.6 kg/cm$^2$ pressure in the presence of Raney nickel (4.5 g.) until the theoretical quantity of hydrogen had been adsorbed (16.25 hours). The catalyst was filtered off and the filtrate evaporated to dryness in vacuo. The residue was dissolved in the minimum quantity of anhydrous ethanol, an excess of an anhydrous solution of hydrogen chloride in diethyl ether was added and the mixture was chilled. The solid which separated was filtered off and washed with anhydrous diethyl ether to give 5-tert-butyl-2-methoxybenzamidine hydrochloride (22.9 g.), m.p. 180°–182° C.

The 5-tert-butyl-2-methoxybenzamidoxime, used as a starting material in the above preparation, was prepared as follows:

Sodium carbonate (57 g.) was added with stirring to a mixture of hydroxylamine hydrochloride (75 g.), 5-tert-butyl-2-methoxybenzonitrile (50 g.) and water (400 ml.) Ethanol (400 ml.) was added, and the mixture was stirred at room temperature for 45 minutes and then heated under reflux for 18 hours. The ethanol was evaporated in vacuo, and the cooled aqueous suspension was extracted three times with diethyl ether. The combined extracts were dried over magnesium sulphate, filtered, and evaporated. The residual glass was triturated with warm diethyl ether, and the solid obtained was filtered off, washed with diethyl ether, and recrystallised from benzene to give 5-tert-butyl-2-methoxybenzamidoxime (48 g.), m.p. 132°–133° C.

The 5-tert-butyl-2-methoxybenzonitrile, used as a starting material in the above preparation, was prepared as follows:

5-tert-Butyl-2-hydroxybenzonitrile (50 g; prepared as described by F. B. Dains and I. R. Rothrock, J. Amer. Chem., 1894 16, 635) was added to a solution of sodium (7.43 g.) in anhydrous ethanol (150 ml.), followed by methyl iodide (50 ml.). The mixture was refluxed for 3 hours, during which time a further quantity of methyl iodide (20 ml.) was added in portions. The mixture was evaporated in vacuo, and the residue treated with water (500 ml.). The oil obtained was extracted with diethyl ether, and the aqueous layer further extracted twice with diethyl ether. The combined extracts were dried and evaporated, and the residual oil was distilled in vacuo to give 5-tert-butyl-2-methoxybenzonitrile (50.3 g.), b.p. 138°–140° C./0.2 mm.Hg.

The 4-benzylbenzamidine hydrochloride, used as a starting material in the above preparation, was prepared as follows:

4-Benzylbenzonitrile (8.7 g; prepared as described by N. Moses, Ber., 1900, 33, 2623) was dissolved in anhydrous chloroform (50 ml.) and anhydrous ethanol (10 ml.), and the solution was saturated at 0° C. with anhydrous hydrogen chloride, and then kept at 0° C. for 3 days. The solvent was removed in vacuo and the residue was triturated with anhydrous diethyl ether. The solid (7 g.) was filtered off and dissolved in saturated anhydrous ethanolic ammonia solution (33 ml.). The solution was kept at 0° C. for 3 days, and evaporated to dryness. The residue was recrystallised from water to give 4-benzylbenzamidine hydrochloride (1.4 g.), m.p. 215°–217° C.

EXAMPLE 14

A solution of 2-(2-methoxy-5-nitrophenyl)-8-azapurin-6-one (1.87 g.) (prepared as described in Example 2) in 2-ethoxyethanol (50 ml.) was shaken at room temperature with a platinum oxide catalyst (0.12 g.) under hydrogen (5 kg/cm$^2$). After the uptake of hydrogen was complete, the filtered solution was concentrated to dryness and the brown residual solid was recrystallised from aqueous N,N-dimethylformamide. A portion of this material was further purified by dissolution in 2N ammonium hydroxide solution followed by acidification of the filtered solution with 2N acetic acid. The brown precipitate was filtered, washed well with water and dried to give 2-(5-amino-2-methoxyphenyl)-8-azapurin-6-one hemihydrate (0.2 g.) in the form of a brown solid, m.p. 204°–206° C. (with decomposition, sintering at about 175° C.).

EXAMPLE 15

Sodium nitrite (1.8 g.) was added to a solution of concentrated hydrochloric acid (15.5 ml) in water (15.5 ml.) at 0° C. The solution was stirred at 0° C. while 4,5-diamino-2-benzylpyrimid-6-one (2.8 g.) was added in portions during 30 minutes. The cooling bath was removed, and the mixture was stirred at room temperature for a further 2 hours, and then allowed to stand for 3 hours. The solid was filtered off, washed with water, and suspended in water (25 ml.). Concentrated aqueous ammonia was added dropwise until most of the solid dissolved. A trace of insoluble solid was removed by filtration, and the filtrate was acidified with glacial acetic acid. The precipitated solid was filtered off and washed with water to give 8-aza-2-benzylpurin-6-one hydrate (2.35 g.) in the form of an off-white solid (melting at 130° C., solidifying and remelting at 220° C. with decomposition). Recrystallisation from water followed by heating the solid in vacuo at 140° C. gave anhydrous 8-aza-2-benzylpurin-6-one (0.55 g.), m.p. 236° C. (with decomposition).

The 4,5-diamino-2-benzylpyrimid-6-one, used as a starting material, was prepared by either of the following procedures:

a. A solution of sodium dithionite (62 g.) in water (300 ml.) was added dropwise during 30 minutes to a solution of 4-amino-2-benzyl-5-phenylazopyrimid-6-one (27 g.) in dimethylformamide (1000 ml.) at 75° C. The mixture was cooled, and the insoluble solid was filtered off. The filtrate was evaporated in vacuo, the residue was stirred with water, and the solid filtered off. This solid was extracted with boiling water (250 ml.), the extract was filtered hot and then cooled. The solid which separated was recrystallised from water to give 4,5-diamino-2-benzylpyrimid-6-one (12.4 g.) in the form of off-white needles, m.p. 243° C. (with decomposition).

b. Sodium dithionite (30 g.) was added in portions to an agitated suspension of 4-amino-2-benzyl-5-phenylazo-pyrimid-6-one (14 g.) in a mixture of ethanol (200 ml.) and 2N aqueous sodium hydroxide solution (200 ml.) maintained at a temperature near to the reflux temperature. The mixture was then heated under reflux for 20 minutes, treated with a further quantity of sodium dithionite (20 g.) and the mixture heated under reflux for a further 30 minutes. The mixture was then evaporated to dryness, the residue was dissolved in water (200 ml.), acidified to pH 6 by means of concentrated hydrochloric acid, cooled to 0° C, and filtered. The solid thus obtained was recrystallised from water to give 4,5-diamino-2-benzyl-pyrimid-6-one (4.4 g.), m.p. 243°–246° C.

The 4-amino-2-benzyl-5-phenylazopyrimid-6-one, used as a starting material in the above preparations, was prepared as follows:

A cold solution of benzenediazonium chloride (prepared by the method well known in the art, from 2 g. aniline) was added dropwise with stirring to a solution of 4-amino-2-benzylpyrimid-6-one (4 g.) and sodium hydroxide (1.6 g.) in water (50 ml.) at 5° C. After stirring for a further 1 hour, the solid was filtered off and recrystallised from a mixture of dimethylformamide and water (4:1 v/v) to give 4-amino-2-benzyl-5-phenylazopyrimid-6-one (3.8 g.) in the form of orange needles, which decomposed at 256°–257° C.

The 4-amino-2-benzylpyrimid-6-one was prepared according to the method described by J. Brock. Z. Chem., 1968, 8, 143.

EXAMPLE 16

Sodium nitrite (0.95 g.) was added slowly with stirring to a solution of concentrated hydrochloric acid (20 ml.) in water (20 ml.) maintained at 5° C. 4,5-Diamino-2-(2-phenylethyl)pyrimid-6-one (1.58 g.) was then added during 5 minutes, maintaining the mixture at 5° C., and stirring at 5° C. was continued for a further 15 minutes. A further portion of sodium nitrite (0.95 g.) was then added, stirring at 5° C. was continued for a further 20 minutes, and the mixture was then maintained at room temperature overnight. The solid which separated was filtered off, washed with a small volume of water, and dissolved in dilute aqueous ammonia. The solution was filtered and acidified to pH 4 46 with glacial acetic acid. The solid obtained (1.36 g.), m.p. 267°–269° C. (with decomposition) was recrystallised from aqueous dimethylformamide and dried at 100° C./0.2 mm.Hg pressure over silica gel to give 8-aza-2-(2-phenylethyl)purin-6-one (0.82 g.), m.p. 275°–277° C. (with decomposition).

By proceeding in a similar manner, but substituting 4,5-diamino-2-(3-phenylpropyl)pyrimid-6-one for the 4,5-diamino-2-(2-phenylethyl)pyrimid-6-one used as a starting material in the above preparation, there was prepared 8-aza-2-(3-phenylpropyl)purin-6-one, m.p. 197°–199° C. (with decomposition) (containing 0.1 mole of ethanol of crystallisation).

The 4,5-diamino-2-(2-phenylethyl)pyrimid-6-one, used as a starting material in the above preparation, was prepared as follows:

Crude sodium salt of 4-amino-5-nitroso-2-(2-phenylethyl)pyrimid-6-one (3.8 g.) was dissolved in water (5.5 ml.). A trace of insoluble material was filtered off, and sodium dithionite (4.08 g.) was added slowly to the filtrate with stirring. The solid which separated was filtered off, washed with water, and recrystallised from ethanol to give 4,5-diamino-2-(2-phenylethyl)pyrimid-6-one (0.75 g.), m.p. 204°–206° C. (with decomposition).

By proceeding in a similar manner, but substituting a solution of 4-amino-5-nitroso-2-(3-phenylpropyl)-pyrimid-6-one in aqueous sodium hydroxide for the aqueous solution of the crude sodium salt of 4-amino-5-nitroso-2-(2-phenylethyl)pyrimid-6-one used in the above preparation, there was prepared crude 4,5-diamino-2-(3-phenylpropyl)pyrimid-6-one.

The sodium salt of 4-amino-5-nitroso-2-(2-phenylethyl)pyrimid-6-one, used as a starting material in the above preparation, was prepared as follows:

3-Phenylpropionamidine hydrochloride (4.33 g; prepared as described by P. W. Neber and A. Uber, Leibig's Annalen der Chemie, 1928, 467, 52) was added to a solution of sodium methoxide (prepared from 2.17 g. sodium and 37 ml. anhydrous methanol). Ethyl α-oximinocyanoacetate (3.34 g.) was added, and the mixture was refluxed with stirring for 5.25 hours and left to stand overnight. The mauve solid was filtered off and washed with a small quantity of anhydrous methanol to give the crude sodium salt of 4-amino-5-nitroso-2-(2-phenylethyl)pyrimid-6-one (3.9 g.). An aliquot was dissolved in water, and the solution was filtered and acidified to pH 4 with glacial acetic acid to give 4-amino-5-nitroso-2-(2-phenylethyl)pyrimid-6-one as a turquoise solid, m.p. 253° C. (with decomposition, sintering at 188° C.).

By proceeding in a similar manner, but substituting 4-phenylbutyramidine hydrochloride for the 3-phenylpropionamidine hydrochloride used as a starting material in the above preparation, there was prepared 4-amino-5-nitroso-2-(3-phenylpropyl)pyrimid-6-one, m.p. 166°–167° C. (with decomposition).

The 4-phenylbutyramidine hydrochloride, used as a starting material in the above preparation, was prepared as follows:

A solution of 4-phenylbutyronitrile (5 g; prepared as described by H. Rupe, Liebig's Annalen der Chemie, 1913, 395, 118) and anhydrous ethanol (5 ml.) in anhydrous chloroform (50 ml.) was cooled in an ice/salt bath and saturated with anhydrous hydrogen chloride. The mixture was allowed to stand at room temperature for 8 days and diluted with anhydrous diethyl ether (250 ml.). The ethyl 4-phenylbutyrimidate hydrochloride (6.44 g.), m.p. 88.5°–90° C. (with decomposition), which separated, was filtered off, and treated with anhydrous saturated ethanolic ammonia (65 ml.), and the mixture kept at room temperature for 2 days. The solution was concentrated to small volume and diluted with anhydrous diethyl ether (200 ml.). The solid obtained was filtered off, and recrystallised firstly from a mixture of ethanol and diethyl ether, and then from a mixture of isopropanol and diethyl ether to give 4-phenylbutyramidine hydrochloride (3.2 g.), m.p. 155°–157° C.

EXAMPLE 17

4,5-Diamino-2-isopropylpyrimid-6-one (2.4 g.) was dissolved with heating in a mixture of concentrated hydrochloric acid (50 ml.) and water (50 ml.), the solution was filtered hot and the filtrate evaporated to dryness. The residue was dissolved in warm water, the solution cooled below 10° C, and sodium nitrite (1.55 g.) added slowly in portions. The mixture was stirred for one hour at below 10° C, then left to stand at 0° C overnight. The solid product was filtered off and the liquors extracted with ethyl acetate to give further product. The combined products were crystallised from water to give 8-aza-2-isopropylpurin-6-one (0.79 g.), m.p. 250°–255° C. (with decomposition). A further quantity of 8-aza-2-isopropylpurin-6-one (0.43 g.),m.p. 255°–256° C. (with decomposition), was obtained from the aqueous recrystallisation liquors.

By proceeding in a similar manner, but substituting 4,5-diamino-2-isobutylpyrimid-6-one for the 4,5-diamino-2-isopropylpyrimid-6-one used as a starting material in the above preparation, there was prepared 8-aza-2-isobutylpurin-6-one, m.p. 225°–230° C.

The 4,5-diamino-2-isopropylpyrimid-6-one, used as a starting material in the above preparation, was prepared as follows:

Sodium dithionite (21 g.) was added in portions to an agitated suspension of 4-amino-2-isopropyl-5-phenylazopyrimid-6-one (8.3 g.) in a mixture of ethanol (140 ml.) and water (140 ml.) maintained at a temperature near to the reflux temperature. The mixture was then heated under reflux for 1 hour, left to stand at 0° C. overnight, and filtered to give crude 4,5-diamino-2-isopropylpyrimid-6-one (2.75 g.), m.p. 200°–220° C. The liquors were continuously extracted with methylene chloride for 48 hours, the extract dried over magnesium sulphate and evaporated to dryness to give a further quantity of the crude product (2.1 g.), m.p. 190°–195° C. The combined products were pure enough for use in the next stage.

An aliquot (0.5 g.) recrystallised from methanol gave pure 4,5-diamino-2-isopropylpyrimid-6-one, (0.23 g.), m.p. 220°–225° C.

By proceeding in a similar manner, but substituting 4-amino-2-isobutyl-5-phenylazopyrimid-6-one for the 4-amino-2-isopropyl-5-phenylazopyrimid-6-one used as a starting material in the above preparation, there was prepared 4,5-diamino-2-isobutylpyrimid-6-one, m.p. 198°–200° C. (recrystallised from water).

The 4-amino-2-isopropyl-5-phenylazopyrimid-6-one, used as a starting material in the above preparation, was prepared as follows:

A cold solution of benzenediazonium chloride [prepared, by the method well known in the art, from 13.3 g. aniline in a 1:1 v/v mixture of water and concentrated hydrochloric acid (120 ml)] was added dropwise with stirring to a solution of 4-amino-2-isopropylpyrimid-6-one (28 g.) and sodium hydroxide (14.8 g.) in water (450 ml.) at 5° C. After stirring for a further 1 hour, the mixture was filtered. The filtrate was adjusted to pH 6 by the addition of aqueous sodium hydroxide solution, and the resultant solid was isolated to give crude 4-amino-2-isopropyl-5-phenylazopyrimid-6-one (33.5 g.), m.p. 215°–219° C. Recrystallisation from ethanol gave pure 4-amino-2-isopropyl-5-phenylazopyrimid-6-one (8.3 g.), m.p. 235°–236° C. (with decomposition).

By proceeding in a similar manner, but substituting 4-amino-2-isobutylpyrimid-6-one for the 4-amino-2-isopropylpyrimid-6-one used as a starting material in the above preparation, there was prepared 4-amino-2-isobutyl-5-phenylazopyrimid-6-one, m.p. 261°–263° C. (with decomposition, recrystallised from isopropanol).

The 4-amino-2-isopropylpyrimid-6-one, used as a starting material in the above preparation, was prepared as follows:

To a stirred solution of sodium (1.15 g.) in dry ethanol (20 ml.) was added ethyl cyanoacetate (1.8 ml.) followed after 15 minutes by isobutyramidine sulphate (2.25 g.). The mixture was refluxed for 20 hours, evaporated to dryness, the residue triturated with water (30 ml.) and the pH adjusted to 6 by the addition of hydrochloric acid. After cooling to 0° C, 4-amino-2-isopropylpyrimid-6-one (1.7 g.), m.p. 248°–250° C, was filtered off and recrystallised from ethanol to give 4-amino-2-isopropylpyrimid-6-one (0.95 g.), m.p. 254° C.

By proceeding in a similar manner, but substituting isovaleramidine hydrochloride for the isobutyramidine sulphate used as a starting material in the above preparation, there was prepared 4-amino-2-isobutylpyrimid-6-one, m.p. 229°–230° C.

The isobutyramidine sulphate and isovaleramidine hydrochloride used as starting materials in the above preparations were prepared by a method similar to that described by N. Z. Drozdov and A. F. Bekhli, Zhur. Obshch. Khim, 1944, 14, 280.

EXAMPLE 18

Sodium nitrate (6.0 g.) was added to a solution of concentrated hydrochloric acid (24 ml.) in water (24 ml.) at 0° C. The solution was stirred at 0° C. while 4,5-diamino-2-cyclohexylpyrimid-6-one (6.0 g.) was added in portions during 30 minutes. The cooling bath was removed, and the mixture was stirred at room temperature for a further 2 hours, and then allowed to stand for 4 hours. The solid was filtered off, washed with water, and recrystallised from a mixture of ethanol and water to give 8-aza-2-cyclohexylpurin-6-one (3.2 g.), m.p. 239°–241° C.

By proceeding in a similar manner, but substituting 4,5-diamino-2-(1,1-diphenylethyl)pyrimid-6-one for the 4,5-diamino-2-cyclohexylpyrimid-6-one used as a starting material in the above preparation, there was prepared 8-aza-2-(1,1-diphenylethyl)purin-6-one, m.p. 267.5°–269° C. (recrystallised from a mixture of dimethylformamide and water).

The 4,5-diamino-2-cyclohexylpyrimid-6-one, used as a starting material in the above preparation, was prepared as follows:

To water (50 ml.), stirred at 70° C, were added in alternate portions 4-amino-2-cyclohexyl-5-nitrosopyrimid-6-one (25 g.) and sodium dithionite until the blue colour was discharged. The pale yellow solid was filtered off and washed with water to give 4,5-diamino-2-cyclohexylpyrimid-6-one (19 g.), m.p. 232–238° C. (with decomposition).

By proceeding in a similar manner, but substituting 4-amino-2-(1,1-diphenylethyl)-5nitrosopyrimid-6-one for the 4-amino-2-cyclohexyl-5-nitrosopyrimid-6-one used as a starting material in the above preparation, there was prepared 4,5-diamino-2-(1,1-diphenylethyl)-pyrimid-6-one, m.p. 218°–220° C. (recrystallised from a mixture of dimethylformamide and water).

The 4-amino-2-cyclohexyl-5-nitrosopyrimid-6-one, used as a starting material in the above preparation, was prepared as follows:

A mixture of 4-amino-2-cyclohexylpyrimid-6-one (18 g.) and water (150 ml.) was stirred and heated to 70° C, and treated slowly with sodium nitrite (8 g.), followed by an excess of glacial acetic acid. The mixture was stirred for a further 1 hour and the blue solid (25 g.) filtered off and used directly for the next stage. A sample recrystallised from glacial acetic acid gave pure 4-amino-2-cyclohexyl-5-nitrosopyrimid-6-one, m.p. 233°–234° C. (with decomposition).

The 4-amino-2-cyclohexylpyrimid-6-one, used as a starting material in the above preparation, was prepared as follows:

To a stirred solution of sodium (8.0 g.) in dry ethanol (150 ml.) was added ethyl cyanoacetate (12 ml.) followed after 15 minutes by crude cyclohexanecarboxamidine fluorosulphonate (10 g.). The mixture was heated under reflux for 20 hours, evaporated to half volume, water (100 ml.) was added and the pH adjusted to 6 by the addition of glacial acetic acid. After cooling to 0° C, the solid was filtered off and washed with water and acetone to give 4-amino-2-cyclohexylpyrimid-6-one (18 g.), m.p. 274°–276° C. (with decomposition).

The cyclohexanecarboxamidine fluorosulphonate, used as a starting material in the above preparation, was prepared as follows:

To a stirred solution of crude methyl cyclohexanecarboximidate fluorosulphonate (19 g.) in dry ethanol (100 ml.) was added dropwise a saturated solution of ammonia in ethanol (100 ml.) After stirring for a further hour at 0°–10° C, the mixture was left to stand at room temperature for 2 days. The mixture was then evaporated to dryness, triturated with ether, and the crude residual cyclohexanecarboxamidine fluorosulphonate (10 g.) used as such in the next stage of the procedure, the preparation of 4-amino-2-cyclohexylpyrimid-6-one.

The methyl cyclohexanecarboximidate fluorosulphonate, used as a starting material in the above preparation, was prepared as follows:

Methyl fluorosulphonate (9.5 g.) was added to a solution of cyclohexanecarboxamide (10 g; prepared as described by H. E. Baumgarten et al, J. Amer. Chem. Soc., 1957, 79, 3145) in dry dichloromethane (100 ml.). After standing at room temperature for 3 days the solution was evaporated to dryness in vacuo. The residue was triturated with dry diethyl ether and the residual gum (19 g.) used as such in the next stage of the procedure, the preparation of cyclohexanecarboxamidine fluorosulphonate.

The 4-amino-2-(1,1-diphenylethyl)-5-nitrosopyrimid-6-one, used as a starting material in the above preparation, was prepared as follows:

A mixture of 1,1-diphenylpropionamidine (0.7 g.), ethyl α-oximinocyanoacetate (0.44 g.) and sodium methoxide (from 0.29 g. sodium) in dry methanol (6 ml.) was heated under reflux, with stirring, for 6 hours. The mixture was then cooled to 20° C, diluted with water (10 ml.) and, with vigorous stirring, acidified to pH 6 by the addition of concentrated hydrochloric acid. The resultant solid was filtered off and recrystallised from aqueous acetic acid to give 4-amino-2-(1,1-diphenylethyl)-5-nitrosopyrimid-6-one (0.66 g.), m.p. 229° C. (with decomposition).

The 1,1-diphenylpropionamidine, used as a starting material in the above preparation, was prepared as follows:

A stirred suspension of methyl 1,1-diphenylpropionimidate fluorosulphonate (6.2 g.) in dry ethanol (50 ml.) maintained at 0° C. was treated dropwise with a saturated solution of ammonia in ethanol (15 ml.). After stirring for a further 1 hour at 0–10° C, the mixture was left to stand at room temperature for 3 days. The mixture was then evaporated to dryness and the residue mixed with water (25 ml.) and chloroform (20 ml.), cooled to 0° C, and treated dropwise with aqueous sodium hydroxide solution (5 ml; 50% w/w). The chloroform layer was separated and the aqueous layer extracted with chloroform (3 × 5 ml.). The combined chloroform solutions were dried over sodium sulphate and evaporated to dryness. The residue was triturated with petroleum ether (b.p. 40°–60° C.) and the solid (2.6 g.) filtered off and recrystallised several times from a mixture of chloroform and petroleum ether (b.p 40°–60° C.) to give 1,1-diphenylpropionamidine (1.2 g.), m.p. 154°–156.5° C.

The methyl 1,1-diphenylpropionimidate fluorosulphonate, used as a starting material in the above preparation, was prepared as follows:

Methyl fluorosulphonate (2.4 g.) was added to a solution of 1,1-diphenylpropionamide (4.5 g, prepared as described by C. R. Hauser and D. S. Hoffenberg, J. Org. Chem., 1955, 20, 1448) in dry dichloromethane (10 ml.). After standing at room temperature for 16 hours, the solid obtained was filtered off and washed with dry diethyl ether to give methyl 1,1-diphenylpropionimidate fluorosulphonate (6.55 g.), m.p. 158°–162° C.

EXAMPLE 19

2-n-Butyl-4,5-diaminopyrimid-6-one (3.0 g.) was dissolved in a hot mixture of concentrated hydrochloric acid (50 ml.) and water (50 ml.). The solution was filtered hot, and the filtrate evaporated to dryness to give a residue which was then dissolved in water (50 ml.). The solution was stirred and maintained at a temperature between 0° and 10° C. during the slow addition of sodium nitrite (1.86 g.) and for 1 hour thereafter. The mixture was then left to stand at 0° C. overnight and then concentrated and the resulting solid (2.95 g.) filtered off and recrystallised from water (decolourising by means of charcoal) to give the sodium salt of 2-n-butyl-8-azapurin-6-one (0.73 g.), which did not melt below 340° C.

The 2-n-butyl-4,5-diaminopyrimid-6-one, used as a starting material in the above preparation, was prepared as follows:

4-Amino-2-n-butyl-5-phenylazapyrimid-6-one (5.6 g.) was dissolved in a mixture of ethanol (90 ml.) and water (90 ml.) and the solution heated almost to boiling. Sodium dithionite (13.6 g.) was added portionwise at such a rate as to maintain reflux, and then the mixture was heated at reflux for a further 1 hour. The mixture was evaporated to dryness, the residue triturated with ice-water (90 ml.) and left to stand at 0° C. overnight. The resultant solid was filtered off and washed with ice-water to give 2-n-butyl-4,5-diaminopyrimid-6-one (3.0 g.), m.p. 160°–165° C, sufficiently pure for use in the next stage of the preparation.

An aliquot was recrystallised from water to give pure 2-n-butyl-4,5-diaminopyrimid-6-one, m.p. 169°–170° C.

The 4-amino-2-n-butyl-5-phenylazopyrimid-6-one, used as a starting material in the above preparation, was prepared as follows:

To a solution of 4-amino-2-butylpyrimid-6-one (7.65 g.) and sodium hydroxide (3.7 g.) in water (115 ml.) was added, at below 5° C, benzene diazonium chloride solution prepared (by the method well known in the art) from aniline (4.64 ml.), and the mixture was then heated to reflux for 1 hour. The pH was adjusted to 6 by the addition of aqueous sodium hydroxide solution, the product was filtered off, washed with water, dried and recrystallised from ethanol to give 4-amino-2-n- butyl-5-phenylazopyrimid-6-one (2.52 g.), m.p. 266°–270° C, pure enough for use in the next stage of the preparation.

An aliquot was recrystallised from ethanol to give pure 4-amino-2-n-butyl-5-phenylazopyrimid-6-one, m.p. 273°–274° C.

The liquors were combined and evaporated and the residue (7.2 g.) was again dissolved in a solution of sodium hydroxide (3.4 g.) in water (104 ml.) and treated with a further quantity of benzene diazonium chloride solution (prepared from 4.3 g. aniline). By continuing as above, there was produced a further quantity of 4-amino-2-n-butyl-5-phenylazopyrimid-6-one (5.6 g.), m.p. 265°–270° C.

The 4-amino-2-n-butylpyrimid-6-one, used as a starting material in the above preparation, was prepared as follows:

Ethyl cyanoacetate (14.7 ml.) was added to a solution of sodium (9.5 g.) in dry ethanol (135 ml.), the mixture was stirred for 1 hour, treated with n-valeramidine hydrochloride (18.8 g, prepared by the method of A. P. T. Easson and F. L. Pyman, J. Chem. Soc., 1931, 2991) and heated to reflux for 3 days. The mixture was evaporated to dryness, the residue triturated with water (100 ml.) and the solution heated to 60° C, treated with glacial acetic acid until pH 6 was attained, and left to stand at 0° C, overnight. The resultant solid was then filtered off and washed with water to give 4-amino-2-n-butylpyrimid-6-one (169 g.), m.p. 242°–245° C, pure enough for use in the next stage of the preparation.

An aliquot was recrystallised from ethanol to give pure 4-amino-2-n-butylpyrimid-6-one, m.p. 252°–253° C.

EXAMPLE 20

A solution of 6-amino-8-aza-2-phenylpurine (0.5 g.) in N hydrochloric acid (100 ml.) was treated with a solution of sodium nitrite (0.75 g.) in water (25 ml.) and heated on the steam bath for 3 hours. A further quantity of sodium nitrite (0.75 g.) was then added, and heating was continued for a further 12 hours. The resulting solid was filtered off and recrystallised from aqueous dimethylformamide to give 8-aza-2-phenylpurin-6-one (0.25 g.), m.p. 278°–280° C. (with decomposition).

The 6-amino-8-aza-2-phenylpurine, used as a starting material in the above preparation, was prepared as follows:

Sodium nitrite (6 g.) was dissolved in an ice-cold solution of concentrated hydrochloric acid (50 ml.) in water (50 ml.). 4,5,6-Triamino-2-phenylpyrimidine (8.8 g; prepared as described by J. Weinstock, R. Y. Dunoff and J. G. Williams, J. Med. Chem. 1968, 11, 542) was added in portions with stirring. A further quantity of sodium nitrite (6 g.) was added, and the mixture was stirred at room temperature for 3 hours. The solid obtained was filtered off, washed with water and dissolved in 15% aqueous ammonia. The solution was filtered and acidified to pH 6 with glacial acetic acid. The solid obtained was filtered off, washed with water, and recrystallised from aqueous dimethylformamide, to give 6-amino-8-aza-2-phenylpurine (4 g.), which did not melt below 300° C.

EXAMPLE 21

5-Amino-4-carbamoyl-1H-1,2,3-triazole (2.5 g.; prepared by the method of J. R. E. Hoover and A. R. Day, J. Amer. Chem. Soc., 1956, 78, 3832), N-methylbenzamidine hydrochloride (4.2 g.) and anhydrous sodium acetate (3.3 g.) were heated together at 200° C. for 3 hours. The mixture was cooled and dissolved in 15% aqueous ammonia (25 ml.). The solution was stirred with charcoal, filtered and acidified with concentrated hydrochloric acid. The solid which separated was filtered off, washed with water, boiled with ethanol and filtered hot to give 8-aza-2-phenylpurin-6-one (0.12 g.), m.p. 274°–276° C. (with decomposition).

EXAMPLE 22

Sodium nitrite (6.8 g.) was dissolved in water (150 ml.) and mixed with 2N aqueous sodium hydroxide solution (54 ml.) and the solution, simultaneously with a solution of crude 4,5-diamino-2-(3-benzylphenyl)-pyrimid-6-one (11.1 g.) in glacial acetic acid (54 ml.), was added with stirring to ice-cooled glacial acetic acid (33 ml.) in such a manner that the temperature remained below 15° C. Stirring was continued for a further 1 hour and the mixture was kept at 0° C. overnight. The solid obtained was filtered off, washed with water and recrystallised from ethanol to give 8-aza-2-(3-benzylphenyl)purin-6-one (2.1 g.), m.p. 249°–251° C. (with decomposition).

The crude 4,5-diamino-2-(3-benzylphenyl)pyrimid-6-one, used as a starting material in the above preparation, was prepared as follows:

4-Amino-2-(3-benzylphenyl)-5-nitrosopyrimid-6-one (11.95 g.) was suspended in water (250 ml.), and triethylamine (20 ml.) was added, giving a purple-red solution. Sodium dithionite (12 g.) was added in portions during 30 minutes with shaking and heating at 60° C. After cooling, the mixture was extracted three times with chloroform, and the combined extracts were dried over magnesium sulphate and evaporated to give crude 4,5-diamino-2-(3-benzylphenyl)pyrimid-6-one (11.1 g.), sufficiently pure to use in the above preparation of 8-aza-2-(3-benzylphenyl)purin-6-one.

The 4-amino-2-(3-benzylphenyl)-5-nitrosopyrimid-6-one, used as a starting material in the above preparation, was prepared as follows:

3-Benzylbenzamidine hydrochloride (12.3 g.) and ethyl α-oximinocyanoacetate (7.1 g.) were added to a solution of sodium (4.6 g.) in anhydrous ethanol (60 ml.). The mixture was heated under reflux with stirring for 5 hours and then allowed to stand at room temperature overnight. The mixture was poured into water (600 ml.), acidified to pH 5 with glacial acetic acid and chilled for 3 hours. The solid obtained was filtered off and washed with water to give 4-amino-2-(3-benzylphenyl)-5-nitrosopyrimid-6-one (11.95 g.), m.p. 145°–148° C. (with decomposition).

The 3-benzylbenzamidine hydrochloride, used as a starting material in the above preparation, was prepared as follows:

3-Benzylbenzonitrile (83.45 g.; prepared as described by C. R. Hauser, W. Q. Beard and F. N. Jones, J. Org. Chem., 1961, 26, 4790) was dissolved in a mixture of anhydrous ethanol (52 ml.) and anhydrous chloroform (390 ml.). The solution was saturated with anhydrous hydrogen chloride at 0° C. and kept at 0° C. for 3 days. The solvent was evaporated in vacuo and the residue triturated with anhydrous diethyl ether. The solid obtained (78 g.) was treated with saturated anhydrous ethanolic ammonia (600 ml.), and the mixture maintained at 0° C. for 3 days. A small amount of ammonium chloride was filtered off and the filtrate was evaporated in vacuo. The gummy residue was triturated with anhydrous diethyl ether to give a solid, which was filtered off and extracted with hot water. The extract was filtered and evaporated to dryness in vacuo. The resulting residue was recrystallised from a mixture of ethanol and diethyl ether (with the aid of charcoal) to give 3-benzylbenzamidine hydrochloride (30.1 g.), m.p. 170°–180° C.

EXAMPLE 23

8-Aza-9-benzyl-2-(2-methoxyethyl)purin-6-one (3.5 g.) was dissolved in redistilled liquid ammonia (70 ml.). Sodium (0.55 g.) was added in portions, with stirring, under reflux. Refluxing was continued for a further 30 minutes, the condenser was removed, an excess of ammonium chloride was added, and the ammonia allowed to evaporate. The residue was dissolved in water, adjusted to pH 5 with 2N hydrochloric acid and continuously extracted with ethyl acetate overnight. The extract was discarded. The aqueous layer was adjusted to pH 3 with 2N hydrochloric acid and again continuously extracted with ethyl acetate overnight. The extract was evaporated in vacuo, to give a residual oil which slowly crystallised. The solid obtained was recrystallised from a mixture of ethyl acetate and diethyl ether to give 8-aza-2-(2-methyoxyethyl)purin-6-one (0.6 g.), m.p. 128°–131° C.

The 8-aza-9-benzyl-2-(2-methoxyethyl)purin-6-one, used as a starting material in the above preparation, was prepared as follows:

5-Amino-1-benzyl-4-carbamoyl-1,2,3-triazole (2.17 g.) was suspended with stirring in 3-methoxypropionyl chloride (5 ml.), cooled in ice, and treated dropwise with concentrated sulphuric acid (0.7 ml.). The mixture was stirred overnight, allowing it to attain room temperature, and then poured into excess ice-water to give a gum. The product was extracted with methylene chloride, and the extract was dried over magnesium sulphate and evaporated to give a yellow gum (2.1 g.). This gum was dissolved in ethanol (21 ml.), and treated with 2N sodium carbonate (21 ml.). The mixture was heated under reflux for 20 hours, evaporated to dryness, treated with water (20 ml.), and some insoluble solid removed by filtration. The aqueous alkaline filtrate was acidified to pH 4 with concentrated hydrochloric acid, and the resulting solid (1.06 g.) filtered off and recrystallised from ethanol to give 8-aza-9-benzyl-2-(2-methoxyethyl)purin-6-one (0.71 g.), m.p. 181°–183° C.

EXAMPLE 24

A solution of 4,5-diamino-2-(2-ethoxyethyl)-pyramid-6-one (2.57 g.) in a mixture of N hydrochloric acid (12.4 ml.) and water (12.4 ml.) was cooled to 0° C. and treated with sodium nitrite (1.4 g.), slowly in portions, and then stirred at 0° C. overnight. The mixture was then filtered to give a solid (a) and a filtrate (b).

The solid (a) [crude 8-aza-2-(2-ethoxyethyl)-purin-6-one; 1.4 g.] was dissolved in dry methanol (15 ml.) and treated with ethylenediamine (2.0 ml.). The mixture was warmed for 5 minutes, treated with excess dry diethyl ether (100 ml.) at 0° C., and the resulting gum as triturated with dry diethyl ether to give a solid (1.5 g.). This solid was recrystallised from a mixture of dry ethanol (25 ml.) and ethyl acetate (35 ml.) to give the ethylenediamine salt of 8-aza-2-(2-ethoxyethyl)purin-6-one (0.66 g.), m.p. 191°–194° C. (with decomposition).

The filtrate (b) was brought to pH 5 by means of dilute hydrochloric acid, extracted with ethyl acetate, and the extract dried over magnesium sulphate and evaporated to dryness to give a further quantity of crude 8-aza-2-(2-ethoxyethyl)purin-6-one (1.4 g.).

The 4,5-diamino-2-ethoxyethyl)pyrimid-6-one, used as a starting material in the above preparation, was prepared as follows:

4-Amino-2-(2-ethoxyethyl)-3-phenylazopyrimid-6-one (7.7 g.) was dissolved in hot ethanol (125 ml.), and water (125 ml.) was added. The mixture was heated almost to boiling, then sodium dithionite (19.2 g.) was added at such a rate as to maintain gentle refluxing. The mixture was then heated under reflux for a further 30 minutes, treated with an additional quantity of sodium dithionite (5 g.), again heated under reflux for 30 minutes, and then evaporated to dryness. The residue was dissolved in water (150 ml.) and continuously extracted with ethyl acetate for 20 hours. The ethyl acetate extract was dried over magnesium sulphate, and evaporated to give crude 4,5-diamino-2-(2-ethoxyethyl)pyrimid-6-one (2.7 g.), sufficiently pure for use in the next stage.

The 4-amino-2-(2-ethoxyethyl)-5-phenylazopyrimid-6-one, used as a starting material in the above preparation, was prepared as follows:

4-Amino-2-(2-ethoxyethyl)pyrimid-6-one (1.68 g.) was dissolved in a stirred solution of sodium hydroxide (0.8 g.) in water (25 ml.), maintained at below 5° C., and treated dropwise with a solution of benzene diazonium chloride prepared (by the method well known in the art) from aniline (1.0 ml.) in a mixture of concentrated hydrochloric acid (2.75 ml.) and water (2.75 ml.).

The orange mixture was then stirred at 0°–2° C. for 3 hours, filtered, and the orange solid washed with ice-water, dried and recrystallised from aqueous ethanol to give 4-amino-2-(2-ethoxyethyl)-5-phenylazopyrimid-6-one (0.7 g.), m.p. 205° C. (with decomposition).

The 4-amino-2-(2-ethoxyethyl)pyrimid-6-one, used as starting material in the above preparation, was prepared as follows:

To a solution of sodium ethoxide in ethanol, prepared from sodium (47.5 g.) and dry ethanol (675 ml.), was added, slowly with cooling and stirring, ethyl cyanoacetate (74 ml.), followed by a solution of 3-methoxypropionamidine hydrochloride (96 g.) in dry ethanol (173ml.). The mixture was stirred and heated under reflux for 40 hours, evaporated to dryness in vacuo, the residue triturated with water (67.5 ml.), acidified to pH 6 with concentrated hydrochloric acid, left to stand at 0° C. overnight and filtered. The aqueous filtrate was extracted continuously with ethyl acetate for 3 days and the extract dried and evaporated to dryness to give crude 4-amino-2-(2-ethoxyethyl)pyrimid-6-one (11.38 g.), m.p. 167°–170° C., sufficiently pure for use in the next stage. A sample was purified by chromatography on silica gel, followed by recrystallisation from ethanol, to give pure 4-amino-2-(2-ethoxyethyl)pyrimid-6-one, m.p. 191°–194° C.

It is to be noted that exchange of the methoxy group for an ethoxy group with the ethanol solvent occurred in the presence of the sodium ethoxide.

The 3-methoxypropionamidine hydrochloride, used as a starting material in the above preparation, was prepared as follows:

3-Methoxypropionitrile (prepared as described by J. H. Mc Gregor and C. Pugh, J. Chem. Soc., 1945, 535)

(99g.) was dissolved in a mixture of dry methanol (40.5 ml.) and dry diethyl ether (50 ml.) and treated at 0° C. with hydrogen chloride gas until 39.3 g. was absorbed (1.25 hours). The flask was stoppered securely and left to stand at 0° C. for 4 days, the hygroscopic solid which separated was filtered off, washed with dry diethyl ether and dried in vacuo. The imino ether hydrochloride thus obtained was treated with an ice-cold saturated dry ethanolic ammonia solution (400 ml.) and left to stand at 0° C. for 4 days, and then stirred for 20 hours at room temperature. The mixture was evaporated to dryness, the residue heated under reflux with dry ethanol (200 ml.), filtered, and evaporated to give crude 3-methoxypropionamidine hydrochloride (109 g.), pure enough for use, without further preparation, in the next stage. The product was characterized by conversion to the picrate, m.p. 169°–171° C.

EXAMPLE 25

8-Aza-9-benzyl-2-phenylpurin-6-one (1.7 g.) was added to redistilled liquid ammonia (40 ml.) with stirring under reflux. Sodium (0.26 g.) was then added in portions, and the mixture stirred under reflux for 30 minutes. The condenser was removed, an excess of ammonium chloride was added cautiously and the ammonia was allowed to evaporate. The residue was extracted with cold water, and the extract was filtered and acidified with concentrated hydrochloric acid. The precipitated solid was filtered off to give 8-aza-2-phenylpurin-6-one (0.5 g.), m.p. 266° C. (with decomposition).

The 8-aza-9-benzyl-2-phenylpurin-6-one, used as a starting material in the above preparation, was prepared by any of the following methods:

a. 5-Benzamido-1-benzyl-4-carbamoyl-1,2,3-triazole (1.0 g.), saturated aqueous sodium bicarbonate solution (5 ml.) and ethanol (5 ml.) were refluxed together for 29 hours. The mixture was cooled in ice, acidified with 2N sulphuric acid and stirred at 0° C. for 20 minutes. The solid was filtered off, washed with water and boiled with ethanol to give 8-aza-9-benzyl-2-phenylpurin-6-one (0.45 g.), m.p. 270°–271° C.

The 5-benzamido-1-benzyl-4-carbamoyl-1,2,3-triazole, used as a starting material in the above preparation, was prepared as follows:

1-Benzyl-4-carbamoyl-5-formamido-1,2,3-triazole (40 g.; prepared as described by A. Albert, J.Chem.-Soc., 1969 (C), 152) was dissolved in 2N sodium hydroxide solution (156 ml.), and treated with alternate successive portions of benzoyl chloride (total 24 ml.) and 2N aqueous sodium hydroxide solution (total 140 ml.) with vigorous agitation, and cooling with ice, over a period of 2 hours. The solution was then acidified to pH 4 with concentrated hydrochloric acid, again cooling with ice, and the precipitated solid was filtered off, dissolved in 2N sodium hydroxide solution (208 ml.) and the solution stirred at 0° C. while portions of benzoyl chloride (total 57 ml.) and 2N sodium hydroxide solution (total 331 ml.) were added alternately over 45 minutes. The resultant mixture was stirred for a further 60 minutes at 0° C. before being acidified to pH 4 with concentrated hydrochloric acid, the temperature being maintained at 0° C. The solid was filtered off and washed successively with water, diethyl ether and water. The solid product was dried, and recrystallised from ethanol to give 5-benzamido-1-benzyl-4-carbamoyl-1,2,3-triazole (23.1 g.), m.p. 191°–192° C.

b. 5-Benzamido-4-benzoylcarbamoyl-1-benzyl-1,2,3-triazole (1 g.), 2N aqueous sodium carbonate solution (5 ml.) and ethanol (5 ml.) were refluxed together for 20 hours. The mixture was cooled in ice, acidified with 2N hydrochloric acid and stirred at 0° C. for 20 minutes. The solid was filtered off, washed with water and dissolved in the minimum quantity of warm dimethylformamide. The solution was filtered, diluted with ethanol and cooled to 0° C. The resulting solid was filtered to give 8-aza-9-benzyl-2-phenylpurin-6-one (0.15 g.), m.p. 274°–276° C. (with decomposition).

The 5benzamido-4-benzoylcarbamoyl-1-benzyl-1,2,3-triazole, used as a starting material in the above preparation, was prepared as follows:

Concentrated sulphuric acid (1.5 ml.) was added dropwise, under anhydrous conditions, to an ice-cooled, stirred suspension of 5-amino-1benzyl-4-carbamoyl-1,2,3-triazole (2.17 g.; prepared as described by J. R. E. Hoover and A. R. Day, J.Amer.Chem.Soc., 1956, 78, 5832) in benzoyl chloride (24 ml.). Stirring was continued at room temperature overnight. The clear solution which formed was then poured into icewater, the precipitated solid was filtered off, washed well with water and diethyl ether to give 5-benzamido-4-benzoylcarbamoyl-1-benzyl-1,2,3-triazole (1.8 g.), m.p. 171°–173° C., suitable for use in the next stage of the preparation. An aliquot was recrystallised from ethanol to give pure 5-benzamido-4-benzoylcarbamoyl-1-benzyl-1,2,3-triazole, m.p. 182°–186° C.

c. Benzoyl chloride (34.8 ml.) was added dropwise, under anhydrous conditions, to an ice-cooled, stirred suspension of 5-amino-1-benzyl-4-carbamoyl-1,2,3-triazole (32.55 g.; prepared by the method of J. R. E. Hoover and A. R. Day, J.Amer.Chem.Soc., 1956, 78, 5832) in anhydrous pyridine (225 ml.). The mixture was then stirred at room temperature for 40 hours, filtered, and poured into a large volume of cold water. The gummy precipitate solidified on standing, and was filtered off, and washed well with water, giving a mixture of mono- and di-benzoyl derivatives of 5-amino-1-benzyl-4-carbamoyl-1,2,3-triazole (56 g.).

A portion of this mixture (0.8 g.) was mixed with 10% sodium hydroxide solution (10 ml.) and ethanol (10 ml.) and heated under reflux for 20 hours. The solution was decanted from a small amount of insoluble material, cooled in ice, and acidified with 2N hydrochloric acid. The pecipitated solid was filtered off, washed with water, and then stirred at room temperature for 2.5 hours with dilute aqueous sodium bicarbonate solution. The undissolved solid was filtered off, and stirred with 2N hydrochloric acid. Filtration then gave 8-aza-9-benzyl-2-phenylpurin-6-one (0.12 g.), m.p. 261°–264° C.

An aliquot of the mixture of mono- and di-benzoyl derivatives of 5-amino-1-benzyl-4-carbamoyl-1,2,3-triazole, prepared as an intermediate in the above preparation, was separated by chromatography to give 5-amino-4-benzoylcarbamoyl-1benzyl-1,2,3-triazole (melting at ca. 160°–170° C. and again at 233°–235° C.), 5-benzamido-4-benzoylcarbamoyl-1-benzyl-1,2,3-triazole (m.p. 187°–189° C.), and 5-amino-4-(N,N-dibenzoylcarbamoyl)-1-benzyl-1,2,3-triazole (m.p. 196°–203° C., with decomposition).

d. 5-Amino-1-benzyl-4-methylcarbamoyl-1,2,3-triazole (2.5 g.), benzamidine hydrochloride (2.5 g.) and anhydrous sodium acetate (3.2 g.) were heated together at 200° C. for 3 hours. The mixture was cooled and extracted four times with warm 15% aqueous ammonia solution (25 ml. portions). The combined extracts were cooled, and the solid which separated was filtered off, boiled with ethanol, and filtered hot to give 8aza-9-benzyl-2-phenylpurin-6-one (0.17 g.), m.p. 269°–271° C. (with decomposition).

The 5-amino-1-benzyl-4-methylcarbamoyl-1,2,3-triazole, used as a starting material in the above preparation, was prepared either by the method of A. Albert, J.Chem.Soc. (C), 1969, 2379, or as follows:

Ethyl cyanoacetate (214 ml.) was added to a solution of sodium (46 g.) in anhydrous methanol (1,600 ml.) at room temperature. The solution was then cooled to 4° C. in an ice-bath, and a 33% w/w solution of methylamine in anhydrous ethanol (300 ml.) was added. The temperature rose to 15° C. The solution was stirred, cooling in an ice-bath, for 3 hours and was then removed from the ice-bath and treated with benzyl azide (248 ml.; prepared by the method of T. Curtius and G. Ehrhart, Ber., 1922, 55, 1559). The solution was heated under reflux for 90 minutes and left to stand at 0° C. overnight. The solid was filtered off, washed with ethanol and diethyl ether, and dried to give 5-amino-1-benzyl-4-methylcarbamoyl-1,2,3-triazole (371.5 g.), m.p. 151°–153° C.

EXAMPLE 26

8Aza-9-benzyl-2-isobutylpurin-6-one (1.7 g.) was added to stirred redistilled liquid ammonia (40 ml.) under reflux. Sodium (0.28 g.) was added in portions with stirring, and the mixture was stirred under reflux for 30 minutes. The condenser was removed, an excess of ammonium chloride was added cautiously, and the ammonia was allowed to evaporate. The residue was extracted with cold water and the insoluble material filtered off. The filtrate was brought to pH 5 by means of hydrochloric acid and continuously extracted with ethyl acetate overnight. The extract was evaporated to dryness and the residual solid was recrystallised from a mixture of acetone and light petroleum (b.p. 60°–80° C.) to give 8-aza-2-isobutylpurin-6-one (0.58 g.), m.p. 223°–224° C. (with decomposition).

The 8-aza-9-benzyl-2-isobutylpurin-6-one, used as a starting material in the above preparation, was prepared by either of the following methods:

a. 1-Benzyl-5-isovaleramido-4-isovalerylcarbamoyl-1,2,3-triazole (8 g.), 2N sodium carbonate solution (50 ml.) and ethanol (20 ml.) were heated together at reflux for 20 hours. The mixture was cooled in ice and acidified with 2N hydrochloric acid. The resulting suspension was stirred at 0° C. for 20 minutes. The solid was filtered off, washed with water and recrystallised from ethyl acetate to give 8-aza-9-benzyl-2-isobutylpurin-6-one (3.45 g.), m.p. 164°–166° C.

The 1-benzyl-5-isovaleramido-4-isovalerylcarbamoyl-1,2,3-triazole, used as a starting material in the above preparation, was prepared as follows:

Concentrated sulphuric acid (7.5 ml.) was added dropwise, under anhydrous conditions, to an ice-cooled, stirred suspension of 5-amino-1-benzyl-4-carbamoyl-1,2,3-triazole (10.85 g.; prepared as described by J. R. E. Hoover and A. R. Day, J.Amer.Chem.Soc., 1956, 78, 5832) in isovaleryl chloride (50 ml.), and the mixture was then stirred at room temperature overnight. The resulting solution was poured into ice-water, and the precipitated solid filtered off, stirred well with water, again filtered off, and dried, to give 1-benzyl-5-isovaleramido-isovalerylcarbamoyl-1,2,3-triazole (16.4 g.), m.p. 125°–128° C. An aliquot was recrystallised from di-isopropyl ether to give pure 1benzyl-5-isovaleramido-4-isovalerylcarbamoyl-1,2,3-triazole, m.p. 130°–131° C.

b. Isovaleryl chloride (10 ml.) was added dropwise, under anhydrous conditions, to an ice-cooled, stirred suspension of 5-amino-1-benzyl-4-carbamoyl-1,2,3-triazole (8.68 g.; prepared as described by J. R. E. Hoover and A. R. Day, J.Amer.Chem.Soc., 1956, 78, 5832) in ahydrous pyridine (80 ml.). The reaction mixture was stirred at room temperature for 2 days, and then poured into ice-water. The brown, gummy solid formed was filtered off, and dried to give a mixture of mono- and di-isovaleryl derivatives of 5-amino-1-benzyl-4-carbamoyl-1,2,3-triazole (8.41 g.).

A portion of the mixture (3 g.) was heated together with 2N aqueous sodium carbonate solution (20 ml.) and ethanol (7 ml.) under reflux for 22 hours. The mixture was cooled to 0° C., acidified with 2N hydrochloric acid, and stirred at 0° C. for 30 minutes. The solid was filtered off, washed with water and recrystallised from ethyl acetate to give 8-aza-9-benzyl-2-isobutylpurin-6-one (0.87 g.), m.p. 166°–168° C.

An aliquot of the mixture of mono- and di-isovaleryl derivatives of 5-amino-1-benzyl-4-carbamoyl-1,2,3-triazole, prepared as an intermediate in the above preparation, was separated by chromatography giving 1-benzyl-4-carbamoyl-5-isovaleramido-1,2,3-triazole (hemihydrate, m.p. 181°–182° C.), 5-amino-1-benzyl-4-isovalerylcarbamoyl-1,2,3-triazole (hemihydrate, m.p. 138°–150° C.), and a mixture of approximately equal parts of 5-amino-1-benzyl-4-(N,N-di-isovalerylcarbamoyl)-1,2,3-triazole and 1-benzyl-4-carbamoyl-5-(N,N-di-isovalerylamino)-1,2,3-triazole, m.p. 142°–146° C.

EXAMPLE 27

Crude sodium salt of 4-amino-2-(2-decyloxyphenyl)-5-nitrosopyrimid-6-one (2 g.) was suspended in water (100 ml.), and sufficient sodium hydroxide was added to give a clear solution at 65° C. Sodium dithionite (1.8 g.) was added in portions at 65° C., and the mixture was cooled to 10° C. Concentrated hydrochloric acid was added with vigorous stirring. The mixture was cooled to 0° C., and and sodium nitrite (2 g.) was added. The mixture was triturated, and after 4 hours the supernatant liquid was removed by decantation. The tarry residue was dissolved in 2N aqueous ammonia solution, treated with charcoal and filtered. The filtrate was acidified with 2N hydrochloric acid, and the waxy precipitate was extracted with ethyl acetate. The extract was dried over magnesium sulphate and evaporated to dryness and the residue was triturated with light petroleum (b.p. 40°–60° C.). The solid obtained was extracted with anhydrous diethyl ether (40 ml.) and the extract was filtered into a solution of ethylenediamine (1 ml.) in anhydrous diethyl ether (10 ml.). The solid obtained was filtered off, washed thoroughly with anhydrous diethyl ether and recrystallised from a mixture of anhydrous ethanol and anhydrous diethyl ether to give the ethylenediamine salt of 8-aza-2-(2-decyloxyphenyl)purin-6-one (0.15 g.), m.p. 115°–118° C. This salt was triturated with 2N acetic acid, and the solid was filtered off, washed with water and dried at 56° C./0.3 mm.Hg over phosphoric oxide for 5.5 hours to give 8-aza-2-(2-decyloxyphenyl)purin-6-one (0.11 g.), m.p. 113°–115° C.

The crude sodium salt of 4-amino-2-(2-decyloxyphenyl)-5-nitrosopyrimid-6-one, used as a starting material in the above preparation, was prepared as follows:

Sodium (7.35 g.) was dissolved in anhydrous methanol (130 ml.), treated with ethyl α-oximinocyanoacetate (11.4 g.) and 2-decyloxybenzamidine hydrochloride (25 g.) and heated to reflux, with stirring, for 4 hours. The mixture was allowed to stand at room temperature overnight and the solid which separated was filtered off, washed with water and dried at 75° C. to give the crude sodium salt of 4-amino-2-(2-decyloxyphenyl)-5-nitrosopyrimid-6-one, pure enough for use in the next stage of the preparation. An aliquot was treated with dilute acetic acid and the solid obtained recrystallised from dilute acetic acid and then from methanol to give pure 4-amino-2-(2-decyloxyphenyl)-5-nitrosopyrimid-6-one, m.p. 144°–146° C.

The 2-decyloxybenzamidine hydrochloride, used as a starting material in the above preparation, was prepared as follows:

Ethyl 2-decyloxybenzimidate borofluoride was mixed with saturated ethanolic ammonia (80 ml.) and left to stand in a closed vessel for 3 days at room temperature. The solvent was then evaporated in vacuo and the residue was treated with 5N sodium hydroxide (15 ml.) and extracted with chloroform. The extract was dried over potassium carbonate and evaporated to dryness. The residual waxy solid (2-decyloxybenzamidine, m.p. 38°–41° C.) was dissolved in anhydrous diethyl ether and treated with an excess of an anhydrous solution of hydrogen chloride in diethyl ether. The solid obtained was filtered off to give 2-decyloxybenzamidine hydrochloride (28 g.), m.p. 124°–127° C. An aliquot was recrystallised from a mixture of anhydrous ethanol and anhydrous diethyl ether to give 2-decyloxybenzamidine hydrochloride, m.p. 127.5°–129° C.

The ethyl 2-decyloxybenzimidate borofluoride, used as a starting material in the above preparation, was prepared as follows:

2-Decyloxybenzamide (38.4 g.) was added to a solution of triethyloxonium borofluoride (30 g.) in anhydrous methylene chloride (90 ml.), and the mixture allowed to stand at room temperature overnight. The solution was concentrated to about 30 ml., diluted with anhydrous diethyl ether (150 ml.), and filtered to give ethyl 2-decyloxybenzimidate borofluoride (45.5 g.), m.p. 93°–96° C., pure enough for use in the next stage. An aliquot was recrystallised from a mixture of anhydrous methylene chloride and anhydrous diethyl ether to give pure ethyl 2-decyloxybenzimidate borofluoride, m.p. 96.5°–98.5° C.

The 2-decyloxybenzamide, used as a starting material in the above preparation, was prepared as follows:

Salicylamide (27.4 g.) and decyl bromide (48.3 ml.) were added to a solution of sodium (4.6 g.) in ethanol (175 ml.) and the mixture was heated to reflux with stirring for 2.25 hours. Most of the ethanol was removed by evaporation in vacuo and the residue was poured into water (350 ml.). The oil which separated solidified, and was filtered off and triturated with 2N sodium hydroxide (150 ml.). The solid was filtered off, washed with water (100 ml.), dried over phosphoric oxide, and recrystallised from light petroleum (b.p. 40°–60° C.) to give 2-decyloxybenzamide (40.5 g.), m.p. 58°–59° C.

EXAMPLE 28

Sodium nitrite (4 g.) was dissolved in a solution of concentrated hydrochloric acid (120 ml.) in water (120 ml.) at 0° C. Crude 4,5-diamino-2-(3,5-dichloro-2-methyoxyphenyl)pyrimid-6-one (6.0 g.) was added in portions during 30 minutes with stirring at 0° C. A further quantity (4 g.) of sodium nitrite was added, and stirring at 0° C. was continued for 30 minutes, followed by stirring at room temperature overnight. The solid obtained was filtered off and dissolved in 2N aqueous ammonia solution. The solution was boiled with charcoal and filtered, and the filtrate acidified with glacial acetic acid. The precipitated solid was filtered off and recrystallised from aqueous dimethylformamide to give 8-aza-2-(3,5-dichloro-2-methoxyphenyl)purin-6-one (3.58 g), m.p. 211°–213° C. (with decomposition).

By proceeding in a similar manner, but substituting crude 4,5-diamino-2-cyclohexylmethylpyrimid-6-one for the crude 4,5-diamino-2-(3,5-dichloro-2-methoxyphenyl)pyrimid-6-one used as a starting material in the above preparation, there was prepared 8-aza-2-cyclohexylmethylpurin-6-one acetate, m.p. 198°–199° C. (after recrystallisation from glacial acetic acid).

The crude 4,5-diamino-2-(3,5-dichloro-2-methoxyphenyl)pyrimid-6-one, used as a starting material in the above preparation, was prepared as follows:

4-Amino-2-(3,5-dichloro-2-methoxyphenyl)-5-nitrosopyrimid-6-one (6.8 g.) was suspended in a solution of triethylamine (10 ml.) in water (100 ml.). Sodium dithionite (7.5 g.) was added, in portions, to the mixture with stirring, and stirring was continued for a further 30 minutes. A further quantity (2 g.) of sodium dithionite was added, and stirring was continued for a further 30 minutes, after which the mixture was allowed to stand overnight. The solid was filtered off and washed with water to give crude 4,5-diamino-2-(3,5-dichloro-2-methoxyphenyl)pyrimid-6-one (6 g.), m.p. 145°–150° C. (with decomposition), pure enough for use in the next stage of the preparation.

By proceeding in a similar manner, but substituting 4-amino-2-cyclohexylmethyl-5-nitrosopyrimid-6-one for the 4-amino-2-(3,5-dichloro-2-methoxyphenyl)-5-nitrosopyrimid-6-one used as a starting material in the above preparation, there was prepared crude 4,5-diamino-2-cyclohexylmethylpyrimid-6-one, m.p. 205°–207° C.

The 4-amino-2-(3,5-dichloro-2-methoxyphenyl)-5-nitrosopyrimid-6-one, used as a starting material in the above preparation, was prepared as follows:

Ethyl α-oximinocyanoacetate (21 g.) was added to a solution of sodium (11.3 g.) in anhydrous methanol (300 ml.). Crude 3,5-dichloro-2-methoxybenzamidine (24 g.) dissolved in a little anhydrous methanol was added, and the mixture was heated to reflux with stirring for 8 hours. The mixture was poured into water (2000 ml.) and acidified with glacial acetic acid. The solid obtained was filtered off, washed with water and recrystallised from glacial acetic acid to give 4-amino-2-(3,5-dichloro-2-methoxyphenyl)-5-nitrosopyrimid-6-one (6.8 g.), m.p. 265° C. (with decomposition).

By proceeding in a similar manner, but substituting crude cyclohexylacetamidine for the 3,5-dichloro-2-methoxybenzamidine used as a starting material in the above preparation, there was prepared 4-amino-2-cyclohexylmethyl-5-nitrosopyrimid-6-one, m.p. 214°–215° C. (with decomposition).

The crude 3,5-dichloro-2-methoxybenzamidine, used as a starting material in the above preparation, was prepared as follows:

A mixture of 3,5-dichloro-2-methoxybenzamide (27 g; prepared as described by N. W. Hirwe, K. N. Rana and K. D. Gavankar, Proc. Indian Acad. Sci., 1938, 8A, 208), triethyloxonium borofluoride (25 g.) and anhydrous methylene chloride (300 ml.) was stirred at room temperature for 8 hours and allowed to stand for a further 40 hours. The solvent was evaporated, and the residue was mixed with saturated anhydrous ethanolic ammonia (250 ml.). The mixture was stirred for 8 hours and allowed to stand at room temperature for a further 60 hours. The solvent was evaporated in vacuo to give crude 3,5-dichloro-2-methoxybenzamidine.

By proceeding in a similar manner, but substituting cyclohexylacetamide (prepared as described by J. Gutt, Ber., 1907, 40, 2061) for the 3,5-dichloro-2-methoxybenzamide used as a starting material in the above preparation, there was prepared crude cyclohexylacetamidine.

EXAMPLE 29

8-Aza-2-(2,5-dibenzyloxyphenyl)purin-6-one (5 g; prepared as described in Example 1) was heated at 100° C. with a 55% w/w solution of hydrogen bromide in glacial acetic acid (100 ml.) for 20 minutes. A further quantity (25 ml.) of the solution of hydrogen bromide in acetic acid was added, and heating was continued for a further 40 minutes. Water (300 ml.) was added and the mixture was allowed to cool to room temperature. The solid obtained was filtered off, washed well with water and recrystallised several times from aqueous dimethylformamide to give 8-aza-2-(2,5-dihydroxyphenyl)purin-6-one (1.8 g.), which decomposed slowly at 300°–310° C.

EXAMPLE 30

8-Aza-2-(2-methoxyphenyl)purin-6-one (1.2 g; prepared as described in Example 1) was added to a hot solution of 2-amino-2-(hydroxymethyl)propane-1,3-diol (0.7 g.) in anhydrous ethanol (20 ml.), and the solution was refluxed for 5 minutes. After cooling, anhydrous diethyl ether (60 ml.) was added and the solid obtained was filtered off, washed with a mixture of acetone and diethyl ether, and recrystallised from a mixture of methanol and diethyl ether to give the 2-amino-2-(hydroxymethyl)propane-1,3-diol salt of 8-aza-2-(2-methoxyphenyl)purin-6-one monohydrate (1.1 g.), m.p. 148°–152° C. (with decomposition, after softening at 135° C.).

EXAMPLE 31

Sodium nitrite (1.1 g.) was added to a stirred mixture of concentrated hydrochloric acid (15 ml.) and water (15 ml.) at 0° C. 4,5-Diamino-2-(5-methyl-2-propoxyphenyl)pyrimid-6-one (2.1 g.) was added with stirring during 10 minutes at 0° C, and stirring at 0° C, was continued for a further 30 minutes. A further quantity (1.1 g.) of sodium nitrite was then added, the cooling bath was removed, and stirring was continued for a further 4 hours. The solid obtained was filtered off, washed with water and dissolved in a 2N aqueous ammonia solution. The solution was filtered and acidified with glacial acetic acid. The solid obtained was filtered off, washed with water and recrystallised from aqueous ethanol to give 8-aza-2-(5-methyl-2-propoxyphenyl)-purin-6-one (0.95 g.), m.p. 235°–236°C. (with decomposition).

The 4,5-diamino-2-(5-methyl-2-propoxyphenyl)-pyramid-6-one, used as a starting material in the above preparation, was prepared as follows:

Sodium dithionite (10.8 g.) was added during 5 minutes to a stirred suspension of the crude sodium salt of 4-amino-2-(5-methyl-2-propoxyphenyl)-5-nitrosopyrimid-6-one (9.3 g.) in water (180 ml.). Stirring was continued for a further 105 minutes, and solid obtained was filtered off, washed with water, and recrystallised from aqueous ethanol to give 4,5-diamino-2-(5-methyl-2-propoxyphenyl)pyrimid-6-one (4.9 g.), m.p. 184°–188° C. (with decomposition).

The crude sodium salt of 4-amino-2-(5-methyl-2-propoxyphenyl)-5-nitrosopyrimid-6-one, used as a starting material in the above preparation, was prepared as follows:

Crude 5-methyl-2-propoxybenzamidine hydrochloride (28.2 g.) and ethyl α-oximinocyanoacetate (17.6 g.) were added to a solution of sodium (11.3 g.) in anhydrous methanol (200 ml.), and the mixture was stirred and heated at reflux for 5 hours. The solid obtained from the cooled mixture was filtered off and washed with methanol and with diethyl ether to give the crude sodium salt of 4-amino-2-(5-methyl-2-propoxyphenyl)-5-nitrosopyrimid-6-one (44.2 g.), m.p. 312°–315° C. (with decomposition).

The crude 5-methyl-2-propoxybenzamidine hydrochloride, used as a starting material in the above preparation, was prepared as follows:

Crude ethyl 5-methyl-2-propoxybenzimidate borofluoride (46.5 g.) was kept at 0° C. with an anhydrous solution (saturated at 0° C.) of ammonia in ethanol (90 ml.) for 4 days in a closed vessel. The solution was evaporated in vacuo, and the residue was treated with water (40 ml.) and 5N sodium hydroxide (80 ml.). The mixture was saturated with sodium chloride and extracted with diethyl ether (400 ml.). The extract was dried over potassium hydroxide, filtered, and evaporated. The residual solid (36 g.), m.p. 78°–81° C, was dissolved in anhydrous ethanol (150 ml.) and treated with a saturated anhydrous solution of hydrogen chloride in diethyl ether (150 ml.) and anhydrous diethyl ether (150 ml.). The precipitated solid was filtered off and washed with anhydrous diethyl ether to give crude 5-methyl-2-propoxybenzamidine hydrochloride (31.3 g.), m.p. 183°–185° C.

An aliquot was recrystallised from a mixture of anhydrous ethanol and anhydrous diethyl ether to give pure 5-methyl-2-propoxybenzamidine hydrochloride, m.p. 184°–185° C.

The crude ethyl 5-methyl-2-propoxybenzimidate borofluoride, used as a starting material in the above preparation, was perpared as follows:

A solution of triethyloxonium borofluoride (34 g.) in anhydrous methylene chloride (90 ml.) was added during 5 minutes to a solution of crude 5-methyl-2-propoxybenzamide (34.5 g.) in anhydrous methylene chloride (300 ml.), and the solution was left to stand at room temperature overnight. The solution was concentrated to about 150 ml. and then diluted with anhydrous diethyl ether (500 ml.). The precipitated solid was filtered off and washed with anhydrous diethyl ether to give crude ethyl 5-methyl-2-propoxybenzimidate borofluoride (47 g.), m.p. 148°–150° C.

An aliquot was recrystallised from a mixture of anhydrous methylene chloride and anhydrous diethyl ether to give pure ethyl 5-methyl-2-propoxybenzimidate borofluoride, m.p. 151-152° C.

The crude 5-methyl-2-propoxybenzamide, used as a starting material in the above preparation, was prepared as follows:

5-Methylsalicylamide (30.2 g; prepared as described in French Pat. No. M21) was dissolved in a solution of sodium (4.6 g.) in ethanol (200 ml.). Propyl iodide (37.4 g.) was added with stirring, and the mixture was stirred for 1 hour at room temperature and then under reflux for a further 19 hours. The mixture was concentrated to about 75 ml. and poured into water (300 ml.). The precipitated solid was filtered off and stirred with 2N sodium hydroxide solution (100 ml.). The insoluble solid was filtered off and washed with water to give crude 5-methyl-2-propoxybenzamide (37.5 g.), m.p. 112°–115° C.

An aliquot was recrystallised from cyclohexane to give pure 5-methyl-2-propoxybenzamide, m.p. 116°–118° C.

EXAMPLE 32

A solution of 8-aza-9-benzyl-2-phenylpurin-6-one (0.5 g; prepared as described in Example 25) in 48% w/w aqueous hydrobromic acid (20 ml.) was heated at 120° C. in a sealed tube for 17 hours. The cooled reaction mixture was then poured into water and filtered. The filtrate was continuously extracted for 20 hours with ethyl acetate, and the organic extract evaporated to dryness. The residue was triturated with isopropanol and the mixture filtered. The filtrate was evaporated to dryness, and the residue recrystallised from water to give 8-aza-2-phenylpurin-6-one (0.01 g.), m.p. 260°–262° C. (with decomposition), whose infra-red spectrum was identical with that of the 8-aza-2-phenylpurin-6-one prepared as hereinbefore described in Example 25.

EXAMPLE 33

A solution of 8-aza-9-benzyl-2-phenylpurin-6-one (0.51 g.) in trifluoromethanesulphonic acid (50 ml.) was shaken for 6.5 hours at room temperature with a 5% palladium on charcoal catalyst (0.51 g.) under hydrogen (4.9 kg/cm$^2$). The reaction mixture was then carefully poured into ice-water (500 ml.) and the catalyst filtered off and extracted with ethanol in a Soxhlet apparatus. The ethanolic solution was filtered from a small amount of solid impurity, and the filtrate evaporated to give a viscous residue, which was triturated with water. The aqueous suspension was adjusted to pH 6 with sodium hydroxide solution, and the solid filtered off and washed with water. The solid was then extracted with a small volume of boiling isopropanol, the mixture allowed to cool, and the solid filtered off. Evaporation of the filtrate gave 8-aza-2-phenylpurin-6-one (0.021 g.), m.p. 257° C. (with decomposition), whose infra-red spectrum was identical with that of the 8-aza-2-phenylpurin-6-one prepared as hereinbefore described in Example 25.

The 8-aza-9-benzyl-2-phenylpurin-6-one, used as a starting material in the above preparation, was prepared by any of the following methods:

a. Toluene-p-sulphonic acid monohydrate (0.26 g.) was heated in refluxing xylene (25 ml.) for about 1 hour, using a Dean and Stark apparatus containing molecular sieve (Linde type 13 X) in the collecting arm, in order to remove water. 5-Amino-1-benzyl-4-carbamoyl-1,2,3-triazole (0.65 g.) was then added, followed after 8 minutes by a solution of triethyl trithioorthobenzoate (0.75 ml.) in anhydrous xylene (5 ml.). Heating at reflux was continued for a further 6 hours. The cooled reaction mixture was then diluted with light petroleum (b.p. 60°–80° C.) (120 ml.) and the precipitated dark brown solid filtered off. The solid was stirred for 2 hours at room temperature in dilute aqueous sodium hydroxide solution, during which time a buff-coloured suspension was formed. The suspension was acidified with hydrochloric acid and stirred well and then the solid was filtered off and washed successively with water, isopropanol and diethyl ether, to give 8-aza-9-benzyl-2-phenylpurin-6-one (0.68 g.), m.p. 266°–268° C.

b. A mixture of 5-amino-1-benzyl-4-carbamoyl-1,2,3-triazole (1.36 g.), benzamidine hydrochloride (1.01 g.) and fused sodium acetate (1.2 g.) was heated at 200° C. until no more ammonia gas was given off.

The residual solid (A) was cooled and extracted with a hot 15% aqueous ammonia solution, the extract was filtered hot and then cooled and filtered again to give a crude product (0.12 g.). The solid (A) was then extracted again with a hot 15% aqueous ammonia solution (60 ml.), the extract was filtered hot, adjusted to pH 7.5 by means of hydrochloric acid and filtered to give a further quantity of crude product (0.15 g.). The combined crude products were recrystallised from ethanol to give 9-benzyl-2-phenyl-8-azapurin-6-one (0.02 g.), m.p. 269°–271° C. (with decomposition). c.

c. A mixture of 5-amino-1-benzyl-4-carbamoyl-1,2,3-triazole (1.0 g.), potassium tert-butoxide (1.7 g.) and dry tert-butanol (20 ml.) was treated with benzotrichloride (0.95 g.) and heated at reflux for 14 hours. The mixture was then evaporated to dryness and the residue extracted successively, with stirring, with a 2N aqueous sodium hydroxide solution (10 ml.), N aqueous sodium hydroxide solution (50 ml. for 4 hours) and water (50 ml. for 2 hours). The extracts were acidified with concentrated hydrochloric acid and filtered to give crude 8-aza-9-benzyl-2-phenylpurin-6-one (0.05 g, 0.12 g. and 0.2 g. respectively). The crude products were combined and recrystallised from ethanol to give 8-aza-9-benzyl-2-phenylpurin-6-one (0.12 g.), m.p. 261°–264° C. (with decomposition). d.

5-Benzamido-1-benzyl-4-carbamoyl-1,2,3-triazole (0.51 g.) was heated at reflux for 3 hours with anhydrous trichlorobenzene (20 ml.) and toluene-p-sulphonic acid (0.027 g.). Addition of light petroleum (b.p. 60°–80° C.) to the cooled solution led to the precipitation of a pale brown solid, which was filtered off and triturated with isopropanol. The remaining solid was filtered off and dissolved in dilute sodium hydroxide solution. The solution was filtered and acidified with concentrated hydrochloric acid. The precipitated solid was filtered off and recrystallised from ethanol (with the use of charcoal) to give 8-aza-9-benzyl-2-phenylpurin-6-one (0.013 g.), m.p 266°–268° C.

EXAMPLE 34

5-Benzamido-4-carbamoyl-1H-1,2,3-triazole (0.5 g.) was stirred for 15.5 hours in refluxing 1N aqueous sodium carbonate solution (15 ml.). The cooled reaction mixture was acidified with hydrochloric acid, giving a solid (0.08 g.) which was filtered off. Upon standing, a further quantity of solid (0.15 g.) separated from the filtrate, and was filtered off. Purification of the combined solids by chromatography gave 8-aza-2-phenylpurin-6-one (0.045 g.), m.p. 258° C. (with decomposition).

The 5-benzamido-4-carbamoyl-1H-1,2,3-triazole, used as a starting material in the above preparation, was prepared by any of the following methods:

a. Benzoyl chloride (3.26 ml.) and 4N aqueous sodium hydroxide solution (8 ml.) were added alternately, in portions over 25 minutes, to a vigorously shaken, ice-cooled solution of 5-amino-4-carbamoyl-1H-1,2,3-triazole (1.27 g; prepared by the method of J. R. E. Hoover and A. R. Day, J. Amer. Chem. Soc., 1956, 78, 5832) in 4N aqueous sodium hydroxide solution (15 ml.). The reaction mixture was extracted with diethyl ether, the aqueous layer cooled and acidified with concentrated hydrochloric acid, and the white precipitate filtered off and washed well with water. The crude solid was stirred in diethyl ether and then purified by dissolving in dilute aqueous sodium hydroxide solution, and reprecipitation by the addition of concentrated hydrochloric acid. The solid was filtered off, washed with water, and dried to give 5-benzamido-4-carbamoyl-1H-1,2,3-triazole (0.085 g.), m.p. 299° C. (with decomposition).

b. Benzoyl chloride (28 ml.) was added dropwise, under anhydrous conditions, to an ice-cooled, stirred suspension of 5-amino-4-carbamoyl-1H-1,2,3-triazole (15.24 g.) in anhydrous pyridine (240 ml.), and the reaction mixture was then stirred at room temperature for 40 hours. The mixture was poured into cold water (1,200 ml.), and the solid filtered off and washed well with water. The crude solid was heated in a large volume of boiling ethanol, and the insoluble material filtered off while still hot, to give 5-benzamido-4-carbamoyl-1H-1,2,3-triazole (20.4 g.), m.p. 301° C. (with decomposition).

c. Concentrated sulphuric acid (1.5 ml.) was added dropwise, under anhydrous conditions, to an ice-cooled, stirred suspension of 5-amino-4-carbamoyl-1H-1,2,3-triazole (1.27 g.) in benzoyl chloride (15 ml.), and the reaction mixture then stirred at room temperature overnight. The mixture was poured into ice-water, whereupon a gummy precipitate was formed. The aqueous solution was decanted off, and the gum triturated thoroughly with diethyl ether. The remaining solid was then filtered off, and washed well with diethyl ether, to give crude 5-benzamido-4-carbamoyl-1H-1,2,3-triazole (2.26 g.), m.p. 280° C. (with decomposition). An aliquot was heated in boiling ethanol, and the solid filtered off, while still hot, to give pure 5-benzamido-4-carbamoyl-1H-1,2,3-triazole, m.p. 306° C. (with decomposition).

EXAMPLE 35

A solution of toluene-p-sulphonic acid monohydrate (0.87 g.) in xylene (150 ml.) was stirred and heated under reflux for 5 minutes, and water then removed azeotropically by distilling off some of the xylene (ca 25 ml.). 5-Amino-4-carbamoyl-1H-1,2,3-triazole (1.27 g; prepared as described by J. R. E. Hoover and A. R. Day, J. Amer. Chem. Soc., 1956, 78, 5832) was added and, after a further 5 minutes under reflux, a further portion of xylene (ca 25 ml.) was distilled off. Triethyl 2-methoxytrithioorthobenzoate (3.02 g.) was then added, and the stirred reaction mixture heated under reflux for 5 hours, and then left to stand overnight at room temperature. The solid was filtered off, and the filtrate cooled and diluted with light petroleum (b.p. 60°–80° C.), whereupon a second crop of solid was obtained. The combined solids were extracted with boiling ethanol (3 × 25 ml.), and the ethanolic extracts combined and evaporated to dryness. The solid so obtained was twice treated with charcoal in boiling ethanol. The solution was filtered, and the filtrate evaporated to dryness. The solid was then dissolved in dilute aqueous sodium hydroxide solution, and the solution acidified with hydrochloric acid. The precipitated solid was recrystallised from isopropanol to give 8-aza-2-(2-methoxyphenyl)-purin-6-one (0.065 g.), m.p. 241° C. (with decomposition), whose infrared spectrum was identical with that of the 8-aza-2-(2-methoxyphenyl)-purin-6-one prepared as hereinbefore described in Example 1.

The triethyl 2-methoxytrithioorthobenzoate used in the above preparation was prepared as follows:

Ethyl mercaptan (93.1 ml.) was added dropwise, under anhydrous conditions, and with stirring, to anhydrous powdered zinc chloride (87.5 g.). The mixture was stirred and heated under reflux for 30 minutes, the heating bath was removed, and 2-methoxybenzoyl chloride (35.7 g; prepared by the method of J. R. Crowdle, E. R. Osgood and J. G. Gaylard, Rec. Trav. Chim., 1954, 73, 559) was added dropwise over 35 minutes. The reaction mixture was then stirred at 60° C. for 5 hours, cooled, and poured into an excess of 4N aqueous sodium hydroxide solution. The mixture was stirred vigorously for 15 minutes, diluted with water, and extracted with diethyl ether (2 × 400 ml.). The combined ethereal extracts were dried over magnesium sulphate and evaporated to dryness. The residual oil was then distilled under reduced pressure, in an atmosphere of dry nitrogen, in a distillation apparatus which had been rinsed with 2H sodium hydroxide solution and then dried without removal of the adhering alkali, to give triethyl 2-methoxytrithioorthobenzoate (8.3 g.), b.p. 143°–148° C./0.3 mm.Hg.

The present invention includes within its scope pharmaceutical compositions which comprise one or more compounds of formula I together with a pharmaceutical carrier or coating. In clinical practice the compounds of the present invention will normally be administered orally, sub-lingually, nasally, rectally or parenterally.

Solid compositions for oral administration include compressed tablets, pills, dispersible powders, and granules. In such solid compositions the active compound or compounds is or are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

The compound(s) may also be administered sublingually by administration of relatively slowly dissolving tablets which, besides including inert diluents as commonly used in the art, may contain sweetening, flavouring, perfuming and preserving agents.

Solid compositions for rectal administration include suppositories formulated in manner known per se and containing the active compound or compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally the compositions should contain 0.1 to 50% by weight of azapurinone compound, especially when in tablet form. When in aerosol form as hereinafter described the compositions should contain 0.2 to 5%, preferably 2 to 5%, by weight of azapurinone compound.

The active compound or compounds may also be administered by methods known for the inhalation of drugs which are not themselves gaseous under normal conditions of administration. Thus, a solution of the compound or compounds in a suitable pharmaceutically acceptable solvent, for example water, can be nebulized by a mechanical nebulizer, for example a Wright Nebulizer, to give an aerosol of finely-divided liquid particles suitable for administration for inhalation orally or nasally. The solutions may contain stabilizing agents and buffering agents to give it an isotonic character, e.g. sodium chloride, sodium citrate and citric acid.

The compound or compounds may also be administered orally or nasally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active compound or compounds in pharmaceutically acceptable solvents, e.g. ethanol, which are co-solvents assisting in dissolving the compound or compounds in the volatile liquid propellant hereinafter described, or pharmaceutically acceptable suspending or dispersing agents, for example aliphatic alcohols such as oleyl alcohol, Span/85 and isopropyl myristate, and incorporating the solutions or suspensions obtained with pharmaceutically acceptable volatile liquid propellants, in conventional pressurized packs which may be made of any suitable material, e.g. metal, plastics or glass, adequate to withstand the pressures generated by the volatile propellants in the pack. Pressurized pharmaceutically acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 to 65 pounds, and are more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of the two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of the compound or compounds in the co-solvent or combining the required quantity of the compound with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting without allowing the temperature to rise above the boiling temperature of the propellant. The temperature of the sealed container is then allowed to rise to ambient temperature with shaking to ensure complete homogeneity of the contents to give a pressurized pack suitable for generating aerosols for inhalation. Alternatively, the co-solvent solution of the compound or compounds or combination of compound or compounds and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

The compound or compounds may also be administered orally by inhalation in the form of a dry micronised powder, which may be diluted with one or more suitable pharmaceutically acceptable inert solid diluents selected from, for example, lycopodium, boric acid, starch, bismuth subcarbonate and heavy magnesium carbonate.

The pharmaceutical compositions of the present invention may contain, in addition to the compound or compounds of formula I, one or more substances known per se to have bronchodilating actions in man, for example, isoprenaline, salbutamol and prostaglandin $E_1$ ($PGE_1$).

By the term "pharmaceutically-acceptable" as applied in this specification to solvent, suspending or dispersing agents, propellants, gases and solid diluents is meant solvents, suspending or dispersing agents, propellants, gases and solid diluents which are nontoxic when used in aerosols suitable for the inhalation therapy.

It is highly desirable that the aerosols or micronised powders should have a particle size less than about 10 microns and preferably less than 5 microns, for example, between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The dose of the compounds of general formula I employed depends upon the desired therapeutic effect, the route of administration and the duration of the treatment. In the adult, the doses are generally between 0.02 and 0.4 mg./kg. body weight per day by administration by inhalation in divided doses.

The following Examples illustrate pharmaceutical compositions according to the present invention:

EXAMPLE 36

Micromilled sodium salt of 8-aza-2-n-butylpurin-6-one (100mg.) and oleyl alcohol (200mg.) were placed in a polyvinyl chloride-coated glass bottle (20ml. capacity) and filled with a mixture of dichlorodifluoromethane and dichlorotetrafluoroethane to give a total volume of 6.2ml. The bottle was sealed with a metered valve (with dip tube) delivering 0.1ml doses. Each puff (generated from 0.1ml of solution) of aerosol released from the pressurized pack thus obtained contained 1mg of 8-aza-2-n-butylpurin-6-one (in terms of the free 8-aza-2-n-butylpurin-6-one).

EXAMPLE 37

The choline salte of 2-(2-methoxyphenyl)-8-azapurin-6-one hemihydrate (73mg) was dissolved in absolute ethanol (0.95ml) and the resulting solution was placed in a polyvinyl chloride-coated glass bottle (20ml volume). The bottle and contents were then cooled to −60°C. and dichlorodifluoromethane (1.72 ml, 2.88 g.) and dichlorotetrafluoroethane (2.28ml, 3.37g.), each at −60°C, were added to give a self-propelling composition(5ml) containing 10mg of 2-(2-methoxyphenyl)-8-azapurin-6-one [in terms of the free 2-(2-methoxyphenyl)-8-azapurin-6-one] per ml of solution.

The bottle was sealed with a metered valve (with dip tube) delivering 0.1ml doses and the contents were rendered homogenous by shaking while allowing the temperature of the bottle and its contents to return to the ambient temperature. Each puff (generated from 0.1ml of solution) of aerosol released from the pressurized pack thus obtained contained 1mg of 2-(2-methoxyphenyl)-8-azapurin-6-one [in terms of the free 2-(2-methoxyphenyl)-8-azapurin-6-one].

EXAMPLE 38

Micromilled triethanolamine salt of 2-(2-methoxyphenyl)-8-azapurin-6-one (100mg) and oleyl alcohol (200mg) were placed in a polyvinyl chloride-coated glass bottle (20ml capacity) and filled with a mixture of dichlorodifluoromethane and dichlorotetrafluoroethane to give a total volume of 6.2ml. The bottle was sealed with a metered valve (with dip tube) delivering 0.1ml doses. Each puff (generated from 0.1ml of solution) of aerosol released from the pressurized pack thus obtained contained 1mg of 2-(2-methoxyphenyl)-8-azapurin-6-one [in terms of the free 2-(2-methoxyphenyl)-8-azapurin-6-one].

In a similar way there was prepared a pressurized pack containing 2-(2-propoxyphenyl)-8-azapurin-6-one by substituting the triethanolamine salt of 2-(2-propoxyphenyl)-8-azapurin-6-one (m.p. 138°–140° C, prepared by application of the procedure of Example 7) for the triethanolamine salt of 2-(2-methoxyphenyl)-8-azapurin-6-one.

We claim:

1. A pharmaceutical composition useful for the treatment of allergic respiratory disorders manifested by the interaction of tissue-fixed antibodies with specific antigens in human subjects which comprises at least one 8-azapurin-6-one derivative of the formula:

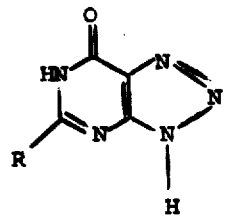

wherein R is phenyl, or phenyl with one to three substituents selected from the group consisting of hydroxy, alkyl, alkoxy, alkenyloxy, phenoxy, phenylalkoxy, and alkylthio, said alkyl and alkyl portion of said alkylthio and phenylalkoxy containing 1 to 6 carbon atoms each, said alkoxy containing 1 to 10 carbon atoms each, and said alkenyloxy containing 2 to 10 carbon atoms each, or a pharmaceutically acceptable salt thereof, in association with a pharmaceutical carrier, the composition containing 0.1 to 50% by weight of said azapurinone compound.

2. The pharmaceutical composition of claim 1 comprising an 8-azapurin-6-one derivative of the formula:

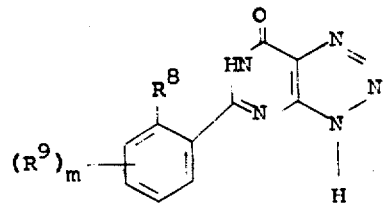

wherein $R^8$ is hydroxy, alkoxy of 1 through 6 carbon atoms, alkenyloxy of 2 through 6 carbon atoms, or phenylalkoxy in which the alkoxy portion is of 1 through 6 carbon atoms, $R^9$ is hydroxy, alkyl or alkoxy of 1 through 6 carbon atoms, or phenylalkoxy in which the alkoxy portion is of 1 through 6 carbon atoms, and $m$ is 0, 1 or 2, the atoms or groups represented by the symbol $R^9$ being the same or different when $m$ is 2, or a pharmaceutically acceptable salt thereof.

3. The pharmaceutical composition of claim 1 comprising an 8-azapurin-6-one derivative of the formula:

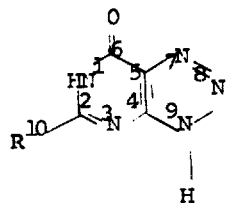

wherein R¹⁰ is phenyl or a group of the formula:

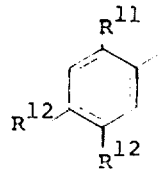

wherein R¹¹ is hydroxy, straight- or branched-chain alkoxy of 1 to 10 carbon atoms, straight- or branched-chain alkenyloxy of 2 to 10 carbon atoms, phenoxy, phenylalkoxy in which the alkoxy moiety is straight- or branched-chain of 1 to 6 carbon atoms, or straight- or branched-chain alkylthio of 1 to 6 carbon atoms, and the symbols R¹² are the same or different and each is hydrogen, hydroxy, straight- or branched-chain alkyl or alkoxy of 1 to 6 carbon atoms, or phenylalkoxy in which the alkoxy moiety is straight- or branched-chain of 1 to 6 carbon atoms, or a pharmaceutically acceptable salt thereof.

4. The pharmaceutical composition of claim 1 in which R is selected from the group consisting of 2-hydroxyphenyl, 2-ethoxyphenyl, 2-isopropoxyphenyl, 2-n-butoxyphenyl, 2-sec-butoxyphenyl, 2-isobutoxyphenyl, 2-n-pentyloxyphenyl, 2-isopentyloxyphenyl, 5-tert-butyl-2-methoxyphenyl, 2-n-hexyloxyphenyl, 2-benzyloxyphenyl, 5-hydroxy-2-methoxyphenyl, 2,4-dimethoxyphenyl, 2,5-dimethoxyphenyl, 2,5-dibenzyloxyphenyl, 5-benzyloxy-2-methoxyphenyl, 2,5-dihydroxyphenyl, 2-methoxy-5-methylphenyl, 2-allyloxyphenyl, phenyl, and 3-n-hexyloxyphenyl.

5. The pharmaceutical composition of claim 1 comprising 8-aza-2-(2-methoxyphenyl)purin-6-one, or a pharmaceutically acceptable salt thereof.

6. The pharmaceutical composition of claim 1 comprising 8-aza-2-(2-propoxyphenyl)purin-6-one, or a pharmaceutically acceptable salt thereof.

7. The composition of claim 1 in liquid form capable of producing an aerosol for administration to human subjects suffering from a respiratory disorder comprising, in a pressurized pack, a solution or suspension of an effective amount of at least one 8-azapurin-6-one as defined in claim 15, or a pharmaceutically acceptable salt thereof, in a pharmaceutically acceptable liquid medium and a volatile liquid propellant in amount sufficient to produce an aerosol.

8. The composition of claim 7 in which the amount of said azapurinone present is 0.2 to 5% by weight of the liquid composition.

9. A pressurized pack provided with a valve permitting emission of an aerosol containing a solution or suspension of at least one 8-azapurin-6-one as defined in claim 1, or a pharmaceutically acceptable salt thereof, in a pharmaceutically acceptable liquid medium under a gaseous pressure capable of converting the 8-azapurin-6-one solution or suspension in the container into an aerosol on release through the valve.

10. The composition of claim 1 in the form of relatively slowly dissolving tablets suitable for sub-lingual administration.

11. A method of treatment of allergic respiratory disorders manifested by the interaction of tissue-fixed antibodies with specific antigens in human subjects which comprises administering orally, sub-lingually, nasally, rectally, or parenterally to the human subject an 8-azapurin-6-one as defined in claim 1, or a pharmaceutically acceptable salt thereof, in an amount sufficient to alleviate the respiratory disorder.

12. The method of claim 11 in which the respiratory disorder is allergic bronchial asthma.

13. The method of claim 11 wherein the 8-azapurin-6-one is a compound of the formula:

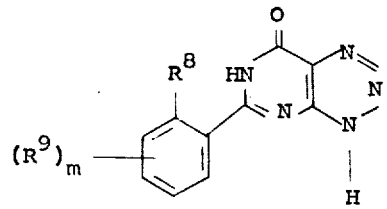

wherein R⁸ is hydroxy, alkoxy of 1 through 6 carbon atoms, alkenyloxy of 2 through 6 carbon atoms, or phenylalkoxy in which the alkoxy portion is of 1 through 6 carbon atoms, R⁹ is hydroxy, alkyl or alkoxy of 1 through 6 carbon atoms, or phenylalkoxy in which the alkoxy portion is of 1 through 6 carbon atoms, and m is 0, 1 or 2, the atoms or groups represented by the symbol R⁹ being the same or different when m is 2, or a pharmaceutically acceptable salt thereof.

14. The method of claim 11 in which the 8-azapurin-6-one is a compound of the formula:

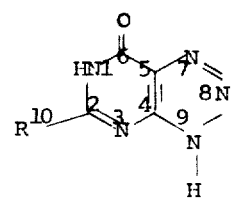

wherein R¹⁰ is phenyl or a group of the formula:

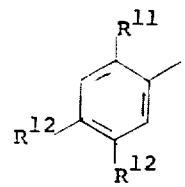

wherein R¹¹ is hydroxy, straight- or branched-chain alkoxy of 1 to 10 carbon atoms, straight- or branched-chain alkenyloxy of 2 to 10 carbon atoms, phenoxy, phenylalkoxy in which the alkoxy moiety is straight- or branched-chain of 1 to 6 carbon atoms, or straight- or branched-chain alkylthio of 1 to 6 carbon atoms, and the symbols R¹² are the same or different and each is hydrogen, hydroxy, straight- or branched-chain alkyl or alkoxy of 1 to 6 carbon atoms, or phenylalkoxy in which the alkoxy moiety is straight- or branched-chain of 1 to 6 carbon atoms, or a pharmaceutically acceptable salt thereof.

15. The method of claim 11 in which the 8-azapurin-6-one is a compound in which R is selected from the group consisting of 2-hydroxyphenyl, 2-ethoxyphenyl, 2-isopropoxyphenyl, 2-n-butoxyphenyl, 2-sec-butoxyphenyl, 2-isobutoxphenyl, 2-n-pentyloxyphenyl, 2- isopentyloxyphenyl, 5-tert-butyl-2-methoxyphenyl, 2-n-hexyloxyphenyl, 2-benzyloxyphenyl, 5-hydroxy-2-methoxyphenyl, 2,4-dimethoxyphenyl, 2,5-dimethoxyphenyl, 2,5-dibenzyloxyphenyl, 5-benzyloxy-2-methoxyphenyl, 2,5-dihydroxyphenyl, 2-methoxy-5-methylphenyl, 2-allyloxyphenyl, phenyl, and 3-n-hexyloxyphenyl.

16. The method of claim 11 in which the 8-azapurin-6-one is 8-aza-2-(2-methoxyphenyl)purin-6-one, or a pharmaceutically acceptable salt thereof.

17. The method of claim 11 in which the 8-azapurin-6-one is 8-aza-2-(2-propoxyphenyl)purin-6-one, or a pharmaceutically acceptable salt thereof.

* * * * *